United States Patent
Hashimoto et al.

(10) Patent No.: US 11,008,388 B2
(45) Date of Patent: *May 18, 2021

(54) RGMA BINDING PROTEIN AND USE THEREOF

(71) Applicants: MITSUBISHI TANABE PHARMA CORPORATION, Osaka (JP); OSAKA UNIVERSITY, Suita (JP); NATIONAL UNIVERSITY CORPORATION CHIBA UNIVERSITY, Chiba (JP)

(72) Inventors: Motonori Hashimoto, Osaka (JP); Toshihide Yamashita, Suita (JP)

(73) Assignees: MITSUBISHI TANABE PHARMA CORPORATION, Osaka (JP); OSAKA UNIVERSITY, Suita (JP); NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/358,657

(22) Filed: Mar. 19, 2019

(65) Prior Publication Data

US 2019/0270799 A1 Sep. 5, 2019

Related U.S. Application Data

(63) Continuation of application No. 15/569,382, filed as application No. PCT/JP2016/063166 on Apr. 27, 2016, now Pat. No. 10,287,346.

(30) Foreign Application Priority Data

Apr. 28, 2015 (JP) .............................. JP2015-091095

(51) Int. Cl.
| | |
|---|---|
| *A61K 39/395* | (2006.01) |
| *C07K 16/28* | (2006.01) |
| *C12N 5/10* | (2006.01) |
| *C12N 15/09* | (2006.01) |
| *A61P 37/00* | (2006.01) |
| *A61P 25/28* | (2006.01) |
| *A61P 25/02* | (2006.01) |
| *A61P 25/00* | (2006.01) |
| *C07K 16/22* | (2006.01) |

(Continued)

(52) U.S. Cl.
CPC ............ *C07K 16/22* (2013.01); *A61K 39/395* (2013.01); *A61P 1/00* (2018.01); *A61P 7/04* (2018.01); *A61P 11/06* (2018.01); *A61P 17/00* (2018.01); *A61P 17/06* (2018.01); *A61P 19/02* (2018.01); *A61P 25/00* (2018.01); *A61P 25/02* (2018.01); *A61P 25/14* (2018.01); *A61P 25/16* (2018.01); *A61P 25/18* (2018.01); *A61P 25/28* (2018.01); *A61P 27/02* (2018.01); *A61P 27/06* (2018.01); *A61P 37/00* (2018.01); *C07K 16/28* (2013.01); *C07K 16/46* (2013.01); *C12N 5/10* (2013.01); *C12N 15/09* (2013.01); *A61K 2039/505* (2013.01); *C07K 2317/21* (2013.01); *C07K 2317/24* (2013.01); *C07K 2317/34* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
CPC ........ C07K 16/18; C07K 16/22; C07K 16/28; C07K 16/46; C07K 2317/21; C07K 2317/24; C07K 2317/56; C07K 2317/565; C07K 2317/76; C07K 2317/92; C07K 2317/94; A61K 39/395; A61K 2039/505; A61P 1/00; A61P 7/04; A61P 11/06; A61P 17/00; A61P 17/06; A61P 19/02; A61P 25/00; A61P 25/02; A61P 25/14; A61P 25/16; A61P 25/18; A61P 25/28; A61P 27/02; A61P 37/00
See application file for complete search history.

(56) References Cited

U.S. PATENT DOCUMENTS

| 6,087,326 A | 7/2000 | Hinck et al. |
|---|---|---|
| 7,166,573 B1 | 1/2007 | Obata |

(Continued)

FOREIGN PATENT DOCUMENTS

| CA | 2724199 A1 | 12/2009 |
|---|---|---|
| CN | 101306193 A | 11/2008 |

(Continued)

OTHER PUBLICATIONS

Edwards et al. J. Mol. Biol. 2003, 334:103-118. (Year: 2003).*
Lloyd et al. Protein Eng. Design & Select, 2009, 22(3):159-168. (Year: 2009).*
U.S. Appl. No. 15/569,382, filed Oct. 25, 2017.
Bell et al., "Structure of the Repulsive Guidance Molecule (RGM)—Neogenin Signaling Hub," *Science*, 341(6141): 77-80 (2013).

(Continued)

*Primary Examiner* — Kimberly Ballard
(74) *Attorney, Agent, or Firm* — Leydig, Voit & Mayer, Ltd.

(57) ABSTRACT

The present invention aims to obtain an anti-repulsive guidance molecule a (RGMa) antibody having a high binding activity and few side effects which can be used as a medicine for preventing, treating, or preventing the relapse of neurological or immunological diseases. The problem is solved by providing an isolated RGMa binding protein which does not inhibit binding between RGMa and neogenin but neutralizes the neurite outgrowth inhibiting activity of RGMa, preferably by providing an anti-RGMa antibody which has complementarity determining regions having amino acid sequences of SEQ ID NOS: 30-35 or SEQ ID NOS: 36-40 in Sequence Listing, and SFG.

17 Claims, 6 Drawing Sheets

Specification includes a Sequence Listing.

(51) Int. Cl.

| | | |
|---|---|---|
| C07K 16/46 | (2006.01) | |
| A61P 25/14 | (2006.01) | |
| A61P 27/02 | (2006.01) | |
| A61P 17/06 | (2006.01) | |
| A61P 27/06 | (2006.01) | |
| A61P 7/04 | (2006.01) | |
| A61P 11/06 | (2006.01) | |
| A61P 17/00 | (2006.01) | |
| A61P 19/02 | (2006.01) | |
| A61P 25/18 | (2006.01) | |
| A61P 1/00 | (2006.01) | |
| A61P 25/16 | (2006.01) | |
| A61K 39/00 | (2006.01) | |

(56) References Cited

U.S. PATENT DOCUMENTS

| | | | |
|---|---|---|---|
| 8,097,253 B2 | 1/2012 | Li et al. | |
| 8,142,782 B2 | 3/2012 | He et al. | |
| 9,102,722 B2 | 8/2015 | Mueller et al. | |
| 9,982,055 B2 * | 5/2018 | Haegel | A61P 19/02 |
| 10,273,307 B2 * | 4/2019 | Simons | A61P 35/00 |
| 2003/0103945 A1 | 6/2003 | Chen et al. | |
| 2004/0102376 A1 | 5/2004 | Mueller et al. | |
| 2004/0199186 A1 | 10/2004 | Kuffler et al. | |
| 2007/0231863 A1 | 10/2007 | Woolf et al. | |
| 2007/0253946 A1 | 11/2007 | Yamashita et al. | |
| 2008/0051319 A1 | 2/2008 | He et al. | |
| 2009/0297527 A1 | 12/2009 | Muller et al. | |
| 2010/0028340 A1 | 2/2010 | Mueller et al. | |
| 2010/0322948 A1 | 12/2010 | Mueller et al. | |
| 2012/0020968 A1 | 1/2012 | Woolf et al. | |
| 2012/0328633 A1 | 12/2012 | Yamashita et al. | |
| 2013/0101605 A1 | 4/2013 | Strittmatter et al. | |
| 2013/0330347 A1 | 12/2013 | Mueller et al. | |
| 2014/0242043 A1 | 8/2014 | Steed et al. | |

FOREIGN PATENT DOCUMENTS

| | | |
|---|---|---|
| CN | 105925578 A | 9/2016 |
| DE | 102008014880 A1 | 9/2009 |
| DE | 102008014880 A8 | 12/2009 |
| EP | 1906185 A1 | 4/2008 |
| JP | 2004-525875 A | 8/2004 |
| JP | 2009-510002 A | 3/2009 |
| JP | 2010-537655 A | 12/2010 |
| JP | 2011-512806 A | 4/2011 |
| JP | 2015-508061 A | 3/2015 |
| JP | 2015-508091 A | 3/2015 |
| WO | WO 1995/013367 A1 | 5/1995 |
| WO | WO 1997/040064 A1 | 10/1997 |
| WO | WO 1998/037085 A1 | 8/1998 |
| WO | WO 1999/008533 A1 | 2/1999 |
| WO | WO 2000/032746 A2 | 6/2000 |
| WO | WO 2004/003150 A2 | 1/2004 |
| WO | WO 2005/087268 A1 | 9/2005 |
| WO | WO 2008/038599 A1 | 4/2008 |
| WO | WO 2011/070045 A1 | 6/2011 |
| WO | WO 2011/071059 A1 | 6/2011 |
| WO | WO 2013/112922 A1 | 8/2013 |
| WO | WO 2013/113107 A1 | 8/2013 |
| WO | WO 2015/039212 A1 | 3/2015 |
| WO | WO 2015/120138 A2 | 8/2015 |
| WO | WO 2015/120138 A3 | 11/2015 |

OTHER PUBLICATIONS

De Hann et al., "Neogenin-1: A New Receptor Critical for Hematopoietic Stem Cell Function," *Experimental Hematology*, 53(Supplement): S47, Abstract 2023 (2017).

Grondona et al., "The Subcommissural Organ and the Development of the Posterior Commissure," *International Review of Cell and Molecular Biology*, 296: 63-137 (2012).

Healey et al., "Repulsive Guidance Molecule is a structural bridge between Neogenin and Bone Morphogenetic Protein," *Nat. Struct. Mol. Biol.*, 22(6): 458-465 (2015).

Key et al., "Repulsive guidance molecule A (RGMa)—A molecule for all seasons," *Cell Adh. Migr.*, 6(2): 85-90 (2012).

Korecka et al., "Repulsive Guidance Molecule a (RGMa) Induces Neuropathological and Behavioral Changes That Closely Resemble Parkinson's Disease," *J. Neurosci.*, 37(39): 9361-9379 (2017).

Lee et al., "Neogenin recruitment of the WAVE regulatory complex maintains adherens junction stability and tension," *Nat. Commun.*, 7: 11082 (2016).

Matsunaga et al., "Repulsive guidance molecule/neogenin: a novel ligand-receptor system playing multiple roles in neural development," *Develop. Growth Differ.*, 46(6): 481-486 (2004).

Qu et al., "Neogenin-1 Promotes Cell Proliferation, Motility, and Adhesion by Up-Regulation of Zinc Finger E-Box Binding Homeobox 1 Via Activating the Rac1/PI3K/AKT Pathway in Gastric Cancer Cells," *Cell Physiol. Biochem.*, 48(4): 1457-1467 (2018).

Sun et al., "Neogenin, a regulator of adult hippocampal neurogenesis, prevents depressive-like behavior," *Cell Death and Disease*, 9: 8 (2018).

Vukicevic et al. (editor), "Introduction" to *Bone Morphogenetic Proteins: Systems Biology Regulators* (2017) [obtained at: link.springer.com/book/10.1007/978-3-319-47507-3].

Yamashita et al., "Neogenin and repulsive guidance molecule signaling in the central nervous system," *Curr. Opin. Neurbiol.*, 17(1): 29-34 (2007).

Iranian Patent Office, Notification of Application Rejection in Iranian Patent Application No. 139650140003008996 (dated May 20, 2019).

Ara et al., "Bone Morphogenetic Proteins 4, 6, and 7 Are Up-Regulated in Mouse Spinal Cord during Experimental Autoimmune Encephalomyelitis," *J. Neurosci. Res.*, 86(1): 125-135 (2008).

Babitt et al., "Repulsive Guidance Molecule (RGMa), a DRAGON Homologue, Is a Bone Morphogenetic Protein Co-receptor," *J. Biol. Chem.*, 280(33): 29820-29827 (2005).

Demicheva et al., "Targeting Repulsive Guidance Molecule A to Promote Regeneration and Neuroprotection in Multiple Sclerosis," *Cell Rep.*, 10(11): 1887-1898 and Graphical Abstract (2015).

Ea et al., "Structure of an Antibody-Antigen Complex: Crystal structure of the HyHEL-10 FAB-Lysozyme complex," *Proc. Natl. Acad. Sci. USA*, 86: 5938-5942 (1989).

Hata et al., "RGMa inhibition promotes axonal growth and recovery after spinal cord injury," *J. Cell Biol.*, 173(1): 47-58 (2006).

Itokazu et al., "Identification of the Neogenin-Binding Site on the Repulsive Guidance Molecule A," *PLoS One*, 7(3): e32791 (2012).

Matsuura et al., "BMP inhibits neurite growth by a mechanism dependent on LIM-kinase," *Biochem. Biophys. Res. Comm.*, 360(4): 868-873 (2007).

Rudikoff et al., "Single amino acid substitution altering antigen-binding specificity," *Proc. Natl. Acad. Sci. USA*, 79: 1979-1983 (1982).

Stahl et al., "Biochemical Characterization of a Putative Axonal Guidance Molecule of the Chick Visual System," *Neuron*, 5(5): 735-743 (1990).

Tian et al., "Repulsive Guidance Molecules (RGMs) and Neogenin in Bone Morphogenetic Protein (BMP) signaling," *Mol Reprod. Dev.*, 80(9): 700-717 (2013).

Paul, William E. (editor), *Fundamental Immunology*, Third Edition, Raven Press, New York, Chapter 9: Structure and Function of Immunoglobulins, pp. 292-295 (1993).

Wilson et al., "Neogenin: One receptor, many functions," *The International Journal of Biochemistry & Cell Biology*, 39(5): 874-878 (2007).

European Patent Office, Extended European Search Report in European Patent Application No. 16786512.0 (dated Sep. 14, 2018).

Japanese Patent Office, International Search Report in International Patent Application No. PCT/JP2016/063166 (dated Jul. 26, 2016).

Russian Patent Office, Office Action in Russian Patent Application No. 2017135353 (dated Apr. 25, 2018).

* cited by examiner

RGMA BINDING PROTEIN AND USE THEREOF

CROSS-REFERENCE TO RELATED APPLICATIONS

This patent application is a continuation of copending U.S. patent application Ser. No. 15/569,382, filed on Oct. 25, 2017, which is the U.S. national phase of International Patent Application No. PCT/JP2016/063166, filed Apr. 27, 2016, which claims the benefit of Japanese Patent Application No. 2015-091095, filed on Apr. 28, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 91,818 bytes ASCII (Text) file named "742239Sequence-Listing.txt," created Mar. 12, 2019.

TECHNICAL FIELD

The present invention relates to an RGMa-binding protein and a use thereof.

BACKGROUND ART

RGM (repulsive guidance molecule), which is a GPI-anchored membrane protein with a molecular weight of about 33 kDa, has been initially identified as an axon guidance molecule in the visual system (see Non-Patent Document 1). The RGM family includes three members called RGMa, RGMb and RGMc. Among them, RGMa is re-expressed after central nervous system injury in adult humans and rats as well as at developmental stage, and RGMa inhibition in rat accelerates neurite outgrowth after spinal cord injury and promotes functional recovery (see Non-Patent Document 2). Thus, RGMa is thought to be a neurite inhibitor after central nervous system injury.

RGMa also has been reported to have effects in the immune system. RGMa is expressed on dendritic cells and acts on T cells, thereby enhancing adhesion of T cells to ICAM-1 and fibronectin and inducing cytokine production (Patent Document 4). In a mouse model of multiple sclerosis, administration of anti-RGMa antibody suppresses symptoms due to encephalomyelitis and also shows effects of suppressing onset and relapse. It is thought that anti-RGMa antibody binds to RGMa expressed on dendritic cells to inhibit the activation of T cells, thereby exerting effects on multiple sclerosis.

The signal transduction mechanism of RGMa is also being elucidated, and neogenin protein has been reported as an RGMa receptor (Patent Document 3). Neogenin is a single-transmembrane protein expressed on neurons and T cells.

RGMa binds to neogenin on a cell membrane to induce intracellular RhoA activation and Ras inactivation, thereby providing a neurite outgrowth inhibitory effect. Meanwhile, neogenin is known to cause apoptosis in the absence of RGMa binding in a developing chicken brain (Matsunaga et al., Dev. Growth Differ. 46, 481, 2004). Thus, the RGMa/neogenin pathway is thought to have two conflicting effects of promoting neuronal survival, which is a favorable effect for nerve regeneration, and of inhibiting neurite outgrowth, a negative effect.

As a pharmaceutical agent targeting RGM, Patent Document 1 discloses an axon regeneration promoting agent containing an anti-RGM neutralizing antibody as an active ingredient. Patent Documents 2 and 3 disclose a therapeutic agent for mechanical damage to brain and spinal cord, an anti-RGM antibody that regulates the binding of RGM to its receptor neogenin. Patent Document 4 discloses medical uses of anti-RGM antibody such as for multiple sclerosis. Patent Document 5 discloses therapeutic uses of anti-RGM antibody for diseases including multiple sclerosis, mammalian brain injury, spinal cord injury, apoplexy, neurodegenerative disease and schizophrenia. Furthermore, Patent Document 6 discloses therapeutic uses of RGM modulators such as anti-RGM antibody for spinal cord injury and multiple sclerosis, and Non-Patent Document 3 discloses a therapeutic use for progressive multiple sclerosis.

PRIOR ART DOCUMENTS

Patent Documents

Patent Document 1: WO2005/087268
Patent Document 2: Japanese Translated PCT Patent Application Laid-open No. 2010-537655
Patent Document 3: Japanese Translated PCT Patent Application Laid-open No. 2009-510002
Patent Document 4: WO2011/071059
Patent Document 5: Japanese Translated PCT Patent Application Laid-open No. 2011-512806
Patent Document 6: Japanese Translated PCT Patent Application Laid-open No. 2004-525875

Non-Patent Documents

Non-Patent Document 1: Neuron 5, 735-743 (1990)
Non-Patent Document 2: J. Cell Biol. 173, 47-58 (2006)
Non-Patent Document 3: Cell Reports 10, 1-12 (2015)

SUMMARY OF THE INVENTION

Technical Problem

Therapeutic uses of anti-RGMa antibody against neurological and immunological diseases are disclosed as described above, but conventional antibodies have problems such as insufficient activity, possibility of impairing intrinsic functions of RGMa, and side effects. In particular, conventional antibodies may inhibit binding between RGMa and neogenin, thereby also inhibiting favorable effects such as apoptosis suppression exerted by neogenin bound to RGMa.

Thus, an object of the present invention is to provide an RGMa-binding protein which does not inhibit RGMa/neogenin interaction but neutralizes the neurite outgrowth inhibiting activity of RGMa.

Solution to Problem

The inventors of the present invention intensively studied in order to solve the above problems. As a result, the present inventors have succeeded in obtaining an RGMa-binding protein which does not inhibit binding between RGMa and neogenin but neutralizes the neurite outgrowth inhibiting activity of RGMa, and have found that the RGMa-binding protein can be used as a medicine for neurological or immunological diseases, thereby completing the present invention.

The present invention is as follows.

[1] An isolated RGMa-binding protein, which does not inhibit binding between RGMa and neogenin but neutralizes the neurite outgrowth inhibiting activity of RGMa.

[2] The RGMa-binding protein described in [1], which binds to human, rat and/or mouse RGMa.

[3] The RGMa-binding protein described in [1] or [2], which binds to peptides of EEVVNAVEDWDSQG (SEQ ID NO: 26 in Sequence Listing), NQQIDFQAFHTNAE (SEQ ID NO: 27 in Sequence Listing), PTAPETFPYET (SEQ ID NO: 28 in Sequence Listing), and/or KLPVEDLYYQA (SEQ ID NO: 29 in Sequence Listing).

[4] The RGMa-binding protein described in any one of [1] to [3], which binds to peptides of SEQ ID NOS: 26 and 27 in Sequence Listing.

[5] The RGMa-binding protein described in any one of [1] to [4], which binds to peptides of SEQ ID NOS: 26, 27 and 28 in Sequence Listing.

[6] The RGMa-binding protein described in any one of [1] to [4], which binds to peptides of SEQ ID NOS: 26, 27 and 29 in Sequence Listing.

[7] The RGMa-binding protein described in any one of [1] to [6], wherein the RGMa-binding protein is a human antibody, a humanized antibody or a chimeric antibody, or an antigen-binding fragment thereof.

[8] A nucleic acid molecule coding for the protein portion of the RGMa-binding protein described in any one of [1] to [7].

[9] A recombinant vector comprising the nucleic acid molecule described in [8].

[10] A host cell containing the recombinant vector described in [9].

[11] A method for producing the RGMa-binding protein described in [1] to [7], the method comprising a step of culturing the host cell described in [10].

[12] A pharmaceutical composition comprising the RGMa-binding protein described in any one of [1] to [7].

[13] The pharmaceutical composition described in [12] for use in preventing, treating, or preventing the relapse of neurological or immunological diseases.

[14] The pharmaceutical composition described in [13], wherein the neurological diseases are selected from the group consisting of amyotrophic lateral sclerosis, brachial plexus injury, brain damage (including traumatic brain injury), cerebral palsy, Guillain-Barre syndrome, cerebral leukodystrophy, multiple sclerosis (including relapsing-remitting multiple sclerosis, primary progressive multiple sclerosis, secondary progressive multiple sclerosis), neuromyelitis optica, post-polio syndrome, spina bifida, spinal cord injury, spinal muscular atrophy, spinal neoplasm, transverse myelitis, dementia (including senile dementia, mild cognitive impairment, Alzheimer's disease, dementia associated with Alzheimer's disease), Huntington's disease, tardive dyskinesia, mania, Parkinson's disease, Steele-Richardson syndrome, Down's syndrome, myasthenia gravis, neurotrauma (including optic nerve trauma), vascular amyloidosis, cerebral hemorrhage associated with amyloidosis, brain infarction, cerebritis, acute confusional state, glaucoma, schizophrenia and retinal nerve fiber layer degeneration (including diabetic retinopathy, ischemic optic neuropathy, X-linked retinoschisis, drug-induced optic neuropathy, retinal dystrophy, age-related macular degeneration, eye diseases characterized by optic disc drusen, eye diseases characterized by genetic determinant for photoreceptor degeneration, autosomal recessive cone-rod dystrophy, mitochondrial disorder associated with optic neuropathy).

[15] The pharmaceutical composition described in [13], wherein the immunological diseases are selected from the group consisting of multiple sclerosis (including relapsing-remitting multiple sclerosis, primary progressive multiple sclerosis, secondary progressive multiple sclerosis), neuromyelitis optica, psoriasis, arthritis (including rheumatoid arthritis, osteoarthritis, psoriatic arthritis), Guillain-Barre syndrome, neuro-Behcet disease, pernicious anemia, type I (insulin-dependent) diabetes mellitus, systemic lupus erythematosus (SLE), inflammatory bowel disease (IBD), Sjogren's syndrome, Goodpasture's syndrome, Graves' disease, autoimmune hemolytic anemia, autoimmune thrombocytopenic purpura, asthma, pollinosis, atopic dermatitis, glomerulonephritis, myasthenia gravis, Hashimoto's disease, and sarcoidosis.

[16] The pharmaceutical composition described in [13], wherein the neurological or immunological diseases are selected from the group consisting of spinal cord injury, neurotrauma (including optic nerve trauma) and multiple sclerosis (including relapsing-remitting multiple sclerosis, primary progressive multiple sclerosis, secondary progressive multiple sclerosis).

[17] An isolated anti-RGMa antibody, or an antigen-binding fragment thereof, wherein the amino acid sequence of each of the light chain complementarity determining region 1 (LCDR1), the light chain complementarity determining region 2 (LCDR2), the light chain complementarity determining region 3 (LCDR3), the heavy chain complementarity determining region 1 (HCDR1), the heavy chain complementarity determining region 2 (HCDR2) and the heavy chain complementarity determining region 3 (HCDR3) comprises the following:

LCDR1: RASQDISSYLN (SEQ ID NO: 30 in Sequence Listing)
LCDR2: YTSRLHS (SEQ ID NO: 31 in Sequence Listing)
LCDR3: QQLNTLP (SEQ ID NO: 32 in Sequence Listing)
HCDR1: DAWMD (SEQ ID NO: 33 in Sequence Listing)
HCDR2: EIRSKANNHATYYAESVKG (SEQ ID NO: 34 in Sequence Listing) and
HCDR3: RDGAY (SEQ ID NO: 35 in Sequence Listing);
or
LCDR1: RSSQSLVHSNGNTYLH (SEQ ID NO: 36 in Sequence Listing)
LCDR2: KVSNRFS (SEQ ID NO: 37 in Sequence Listing)
LCDR3: SQSTHVP (SEQ ID NO: 38 in Sequence Listing)
HCDR1: TSYYWN (SEQ ID NO: 39 in Sequence Listing)
HCDR2: YISYDGTNNYNPSLKN (SEQ ID NO: 40 in Sequence Listing) and
HCDR3: SFG, and wherein in each of the CDR sequences one or several amino acids may be substituted, deleted, and/or added.

[18] The anti-RGMa antibody or an antigen-binding fragment thereof described in [17], wherein the heavy chain variable region (VH) comprises the following:
VH: EVQLVESGGGLVQPGRSLRLSCTASGFTFSDAWMDWVRQAPGKGLEWVAEIRSKANNHATYYAES VKGRFTISRDDSKSIVYLQMNSLRTEDTALYYCTRRD GAYWGKGTTVTVSS (SEQ ID NO: 41 in Sequence Listing) or an amino acid sequence having an identity of at least 90% with said amino acid sequence; and wherein the light chainvariable region (VL) comprises the following:
VL:DIQMTQSPSSVSASVGDRVTITCRASQDISSYLNW YQQKPGKAPKLLIYYTSRLHSGVPSRFSGSGSGTDF TLTISSLQPEDFASYFCQQLNTLPWTFGGGTKVEME (SEQ ID NO: 42 in Sequence Listing) or an amino acid sequence having an identity of at least 90% with said amino acid sequence.

[19] The anti-RGMa antibody or an antigen-binding fragment thereof described in [17] or [18], wherein the anti-RGMa antibody is a humanized antibody.

[20] The anti-RGMa antibody or an antigen-binding fragment thereof described in any one of [17] to [19], wherein the anti-RGMa antibody comprises a constant region of human IgG.

[21] An RGMa-binding protein, which competes with the anti-RGMa antibody described in [17] or [18] for binding to RGMa.

[22] A nucleic acid molecule coding for the protein portion of the anti-RGMa antibody or an antigen-binding fragment thereof described in any one of [17] to [20].

[23] The nucleic acid molecule described in [22], wherein the nucleotide sequences coding for the VH and VL amino acid sequences each is a nucleotide sequence comprising:

```
VH:
gaagtgcagctggtggaatctggcggcggactggtgcagcctggcagatc cctgagactgtcctgtaccgcctccggcttcaccttctccgacgcctgga tggattgggtgcgacaggtcctggcaagggcctggaatgggtggccgag atccggtccaaggccaacaaccacgccacctactacgccgagtctgtgaa gggccggttcaccatctcccgggacgactccaagtccatcgtgtacctgc agatgaactccctgcggaccgaggacaccgccctgtactactgcaccaga agggacggcgcctactggggcaagggcaccacagtgacagtgtcctcc
(SEQ ID NO: 43 in Sequence Listing),
and VL:
gacatccagatgacccagtcccctcctccgtgtctgcttccgtgggcga cagagtgaccatcacctgtcgggcctcccaggacatctcctcctacctga actggtatcagcagaagcccggcaaggcccccaagctgctgatctactac acctcccggctgcactccggcgtgccctctagattttccggctctggctc cggcaccgactttaccctgaccatctccagcctgcagcccgaggacttcg cctcctacttctgtcagcagctgaacaccctgccctggacattggcggag gcaccaaggtggaaatggaa
(SEQ ID NO: 44 in Sequence Listing).
```

[24] A recombinant vector comprising the nucleic acid molecule described in [22] or [23].

[25] A host cell containing the recombinant vector described in [24].

[26] A method for producing the anti-RGMa antibody or an antigen-binding fragment thereof described in any one of [17] to [20], the method comprising a step of culturing the host cell described in [25].

[27] A pharmaceutical composition comprising the anti-RGMa antibody or an antigen-binding fragment thereof described in any one of [17] to [20].

[28] The pharmaceutical composition described in [27] for use in preventing, treating, or preventing the relapse of neurological or immunological diseases.

[29] The pharmaceutical composition described in [28], wherein the neurological diseases are selected from the group consisting of amyotrophic lateral sclerosis, brachial plexus injury, brain damage (including traumatic brain injury), cerebral palsy, Guillain-Barre syndrome, cerebral leukodystrophy, multiple sclerosis (including relapsing-remitting multiple sclerosis, primary progressive multiple sclerosis, secondary progressive multiple sclerosis), neuromyelitis optica, post-polio syndrome, spina bifida, spinal cord injury, spinal muscular atrophy, spinal neoplasm, transverse myelitis, dementia (including senile dementia, mild cognitive impairment, Alzheimer's disease, dementia associated with Alzheimer's disease), Huntington's disease, tardive dyskinesia, mania, Parkinson's disease, Steele-Richardson syndrome, Down's syndrome, myasthenia gravis, neurotrauma (including optic nerve trauma), vascular amyloidosis, cerebral hemorrhage associated with amyloidosis, brain infarction, cerebritis, acute confusional state, glaucoma, schizophrenia and retinal nerve fiber layer degeneration (including diabetic retinopathy, ischemic optic neuropathy, X-linked retinoschisis, drug-induced optic neuropathy, retinal dystrophy, age-related macular degeneration, eye diseases characterized by optic disc drusen, eye diseases characterized by genetic determinant for photoreceptor degeneration, autosomal recessive cone-rod dystrophy, mitochondrial disorder associated with optic neuropathy).

[30] The pharmaceutical composition described in [28], wherein the immunological diseases are selected from the group consisting of multiple sclerosis (including relapsing-remitting multiple sclerosis, primary progressive multiple sclerosis, secondary progressive multiple sclerosis), neuromyelitis optica, psoriasis, arthritis (including rheumatoid arthritis, osteoarthritis, psoriatic arthritis), Guillain-Barre syndrome, neuro-Behcet disease, pernicious anemia, type I (insulin-dependent) diabetes mellitus, systemic lupus erythematosus (SLE), inflammatory bowel disease (IBD), Sjogren's syndrome, Goodpasture's syndrome, Graves' disease, autoimmune hemolytic anemia, autoimmune thrombocytopenic purpura, asthma, pollinosis, atopic dermatitis, glomerulonephritis, myasthenia gravis, Hashimoto's disease, and sarcoidosis.

[31] The pharmaceutical composition described in [28], wherein the neurological or immunological diseases are selected from the group consisting of spinal cord injury, neurotrauma (including optic nerve trauma) and multiple sclerosis (including relapsing-remitting multiple sclerosis, primary progressive multiple sclerosis, secondary progressive multiple sclerosis).

[32] A method for preventing, treating, or preventing the relapse of neurological or immunological diseases, the method comprising a step of administrating a effective dose of the RGMa-binding protein described in any one of [1] to [7] to a subject in need thereof.

[33] A method for preventing, treating, or preventing the relapse of neurological or immunological diseases, the method comprising a step of administrating an effective dose of the anti-RGMa antibody or an antigen-binding fragment thereof described in any one of [17] to [20] to a subject in need thereof.

Advantageous Effect of the Invention

The RGMa-binding protein of the present invention does not inhibit the interaction between RGMa and neogenin, thereby being able to maintain effects such as apoptosis inhibition on neurons and the like exerted by neogenin bound to RGMa, thus having a strong protective effect on neurons and little concern for side effects associated with neuron depletion. In addition, the humanized anti-RGMa antibody of the present invention is superior to conventional antibodies in properties such as binding to human RGMa and thermal stability. Therefore, the antibody can be used as a medicine for neurological or immunological diseases which has an excellent efficacy and few side effects.

DESCRIPTION OF THE EMBODIMENTS

Figure 1:
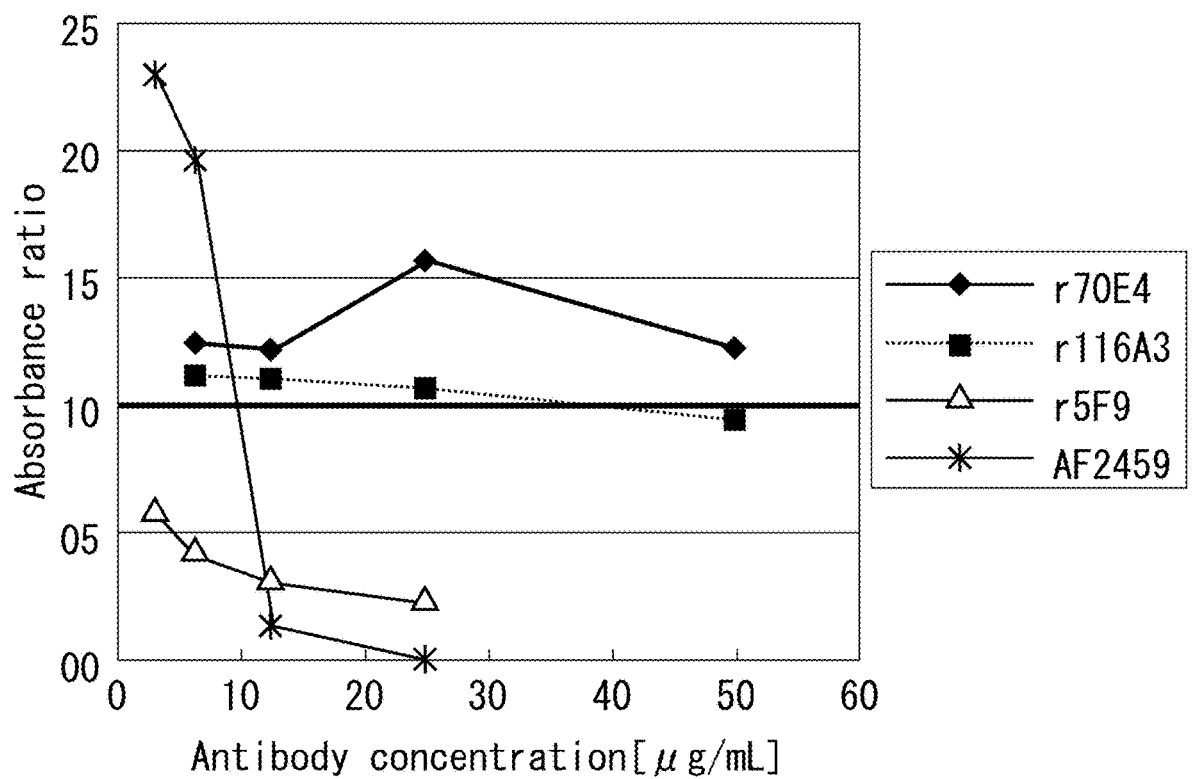
FIG. 1 shows a result of an RGMa-neogenin binding inhibition assay using an anti-RGMa polyclonal antibody (AF2459), an antibody of comparative example (r5F9), and antibodies of the present invention (r70E4 and 116A3).

In order to facilitate understanding of the present invention, the terms used in the present invention will be explained below.

RGMa

RGMa is a neurite outgrowth inhibitory protein in the central nervous system and human RGMa protein is biosynthesized as a precursor protein comprising 450 amino acids as shown in SEQ ID NO: 1 in Sequence Listing. The signal peptide Met 1 to Pro 47 present at the N terminus (which refers to the peptide from the first methionine residue to the 47th proline residue from the N-terminal side, similarly described hereafter) is removed, the peptide bond between Asp 168 and Pro 169 is cleaved, and the C-terminal peptide Arg 423 to Cys 450 is removed and simultaneously a GPI anchor is added to the C-terminal carboxyl group of Gly 422 which has become the C-terminus. A human RGMa protein is expressed on a cell membrane via the GPI anchor as a mature protein in which the N-terminal domain (Cys 48 to Asp 168) and the C-terminal domain (Pro 169 to Ala 424) are joined together by a disulfide bond. A precursor protein of mouse RGMa comprises the amino acid sequence shown in SEQ ID NO: 2 in Sequence Listing and a precursor protein of rat RGMa comprises the amino acid sequence shown in SEQ ID NO: 3 in Sequence Listing. Since their C terminal peptides are removed, mature proteins therefrom have the same amino acid sequences. In the present invention, RGMa may refer to either a precursor protein, a mature protein or an active fragment thereof, or may be a derivative or variant thereof, as long as it acts via binding to neogenin as described later. RGMa may be human RGMa or RGMa derived from other organisms, but human RGMa is preferred.

Neogenin

Neogenin is expressed in, for example, central nervous neurons and functions as one of RGMa receptors. As shown in SEQ ID NO: 10 in Sequence Listing, the human neogenin protein comprises 1461 amino acids and is expressed as a mature membrane protein after removal of the signal peptide Met 1 to Ala 33. In the present invention, neogenin may refer to either a precursor protein, a mature protein or an RGMa-binding fragment, or may be a derivative or variant thereof, as long as it binds to RGMa. Neogenin may be human neogenin or neogenin derived from other organisms, but human neogenin is preferred.

Neutralization

The term "neutralization" as used herein refers to an action through which binding to a target of interest and inhibition of any function of the target can occur. In other words, the phrase "neutralizing the neurite outgrowth inhibitory activity of RGMa" means that an RGMa binding protein binds to RGMa, thereby inhibiting the neurite outgrowth inhibitory activity of RGMa. Neurite outgrowth inhibitory activity can be assessed by one or more of several in vitro or in vivo assays known in the art, and can be assessed by, for example, the neurite outgrowth inhibition assay described herein.

Isolated

The term "isolated" such as in isolated RGMa-binding protein means being identified, and separated and/or recovered from components in its natural state. Impurities in the natural state are substances that can interfere with the diagnostic or therapeutic use of the antibody, including enzymes, hormones and other proteinous or nonproteinous solutes. Generally, isolation of RGMa-binding protein or the like can be achieved by at least one purification step. The RGMa binding protein purified by at least one purification step can be referred to as "isolated RGMa-binding protein".

RGMa Binding Protein

As used herein, the term "RGMa-binding protein" refers to a molecule comprising a protein that binds to RGMa. Examples of the RGMa-binding proteins include anti-RGMa antibodies and antigen-binding fragments thereof; RGMa-binding scaffold proteins; soluble RGMa receptor proteins such as extracellular domain of Neogenin; and fusion proteins thereof. The term "RGMa-binding scaffold protein" refers to a protein that realizes the function of binding to RGMa by introduction of mutations into the Kunitz domain of a serine protease inhibitor, the extracellular domain of human fibronectin, ankyrin, lipocalin or the like. The term "fusion protein" refers to RGMa-binding proteins bound chemically or genetically to function molecules other than the RGMa-binding protein of the present application such as nonpeptidic polymers such as polyethylene glycol (PEG), radioactive substances, toxins, low molecular weight compounds, cytokines, growth factors (e.g., TGF-β, NGF, neurotrophin), albumin, enzymes, and other antibodies.

Human Antibody

The term "human antibody" refers to an antibody in which light and heavy chains are both derived from human immunoglobulin. Depending on the difference in constant regions of heavy chains, human antibodies include IgG having γ-heavy chains (including IgG1, IgG2, IgG3 and IgG4), IgM having μ-heavy chains, IgA having α-heavy chains (including IgA1 and IgA2), IgD having δ-heavy chains, or IgE having ε-heavy chains. Light chains, in principle, comprise either κ chains or λ chains.

Humanized Antibody

The term "humanized antibody" refers to an antibody comprising variable regions comprising complementarity determining regions of an antibody derived from a nonhuman animal and framework regions derived from a human antibody, and constant regions derived from a human antibody.

Chimeric Antibody

The term "chimeric antibody" refers to an antibody in which the light chain, the heavy chain, or both comprises a non-human derived variable region and a human derived constant region.

Anti RGMa Antibody

As used herein, the term "anti-RGMa antibody" refers to immunoglobulin molecules which bind to RGMa, or modified molecules thereof. Modified molecules include multispecific antibodies, chimeric antibodies, humanized antibodies, functionally modified antibodies, and conjugated antibodies.

Multispecific Antibody

The term "multispecific antibody" refers to an asymmetric antibody comprising two or more independent antigen recognition sites having two or more different antigen specificities, including bispecific antibody having two antigen specificities and trispecific antibody having three antigen specificities.

Functionally Modified Antibody

As used herein, the term "functionally modified antibody" refers to an antibody in which functions other than the antigen binding function of the antibody, including cell killing function, complement activating function and serum half-life extending function, are modified by mainly modifying the amino acid or sugar chain of the Fc region of the antibody.

Conjugated Antibody

As used herein, the term "conjugated antibody" refer to an antibody bound chemically or genetically to function molecules other than antibody such as nonpeptidic polymers such as polyethylene glycol (PEG), radioactive substances, toxins, low molecular weight compounds, cytokines, growth factors (e.g., TGF-β, NGF, neurotrophin), albumin, and enzymes.

Antigen-Binding Fragment

As used herein, the term "antigen-binding fragment" refers to a protein which comprises a part of an antibody and can bind to an antigen. Examples of the antigen-binding fragment include F(ab')2, Fab', Fab, Fv (variable fragment of antibody), disulfide-linked Fv, single-chain antibody (scFv), and polymers thereof. In addition, the antigen-binding fragment includes conjugated antigen-binding fragments bound chemically or genetically to function molecules other than the anti-RGMa antibody in the present application such as nonpeptidic polymers such as polyethylene glycol (PEG), radioactive substances, toxins, low molecular weight compounds, cytokines, growth factors (e.g., TGF-β, NGF, neurotrophin), albumin, enzymes, and other antibodies.

Complementarity Determining Region

The term "complementarity determining region (CDR)" refers to a region forming an antigen binding site in a variable region of an immunoglobulin molecule, which is also called a hypervariable region, and particularly refers to a portion in which the amino acid sequence changes greatly for each immunoglobulin molecule. As CDR, light and heavy chains each have three CDRs (LCDR1, LCDR2, LCDR3, and HCDR1, HCDR2, HCDR3). In the present application, CDRs of an immunoglobulin molecule are determined according to the Kabat numbering system (Kabat et al., 1987, Sequences of Proteins of Immunological Interest, US Department of Health and Human Services, NIH, USA).

Percent (%) Identity of Amino Acid Sequence

"Percent (%) identity" with respect to the identified reference polypeptide sequence, such as variable region, is defined as the percentage of amino acid residues in a candidate sequence that are identical to the amino acid residues of a particular reference polypeptide sequence, after arranging the sequences and introducing gaps as necessary in order to obtain maximal % identity and assuming that no conservative substitutions are considered part of the sequence identity. Alignment for purposes of determining % identity can be accomplished by using various methods within the skill of the art, for example, using publicly available computer software such as BLAST, BLAST-2, ALIGN, or Megalign (DNASTAR) software. Those skilled in the art can determine appropriate parameters for aligning sequences, including any algorithms necessary to achieve maximal alignment over the full length of the sequences being compared. However, for purposes herein, % identity values are obtained by using the sequence comparison computer program BLAST in pairwise alignments.

In situations where BLAST is used for amino acid sequence comparisons, the % identity of a given amino acid sequence A to a given amino acid sequence B is calculated as follows:

$$100 \text{ times the fraction } X/Y$$

where X is the number of amino acid residues scored as identical matches by the sequence alignment program Blast in that program's alignment of A and B, and where Y is the total number of amino acid residues in B. It will be appreciated that if the length of amino acid sequence A is different from the length of amino acid sequence B, the % identity of A to B will be different from the % identity of B to A. Unless stated otherwise, all % identity values herein are obtained using the BLAST computer program as shown in the immediately preceding paragraph.

Competing

As used herein, the term "competing" with the anti-RGMa antibody of the present invention means that, as measured by the surface plasmon resonance (SPR) described herein, the binding between the anti-RGMa antibody of the present invention and RGMa is decreased with a significant difference due to the presence of said anti-RGMa antibody or an antigen-binding fragment thereof.

The present invention will be described in detail below.

RGMa Binding Protein

The RGMa-binding protein of the present invention is an isolated RGMa-binding protein, which does not inhibit binding between RGMa and neogenin but neutralizes neurite outgrowth inhibiting activity of RGMa.

Preferably, RGMa proteins are RGMa proteins derived from mammals. For example, human RGMa proteins include a protein having the amino acid sequence of SEQ ID NO: 1 in Sequence Listing, mouse RGMa proteins include a protein having the amino acid sequence of SEQ ID NO: 2 in Sequence Listing, and rat RGMa proteins include a protein having the amino acid sequence of SEQ ID NO: 3 in Sequence Listing. A polypeptide comprising an amino acid sequence wherein one or several (preferably 1 to 20, more preferably 1 to 10, still more preferably 1 to 5) amino acids in these sequences are substituted, deleted, inserted and/or added and having substantially the same activity as RGMa protein; or a polypeptide comprising an amino acid sequence having 90% or more (preferably 95% or more) identity to the amino acid sequence may also be preferred.

As used herein, a polypeptide "having substantially the same activity as RGMa protein" includes any polypeptide as long as the polypeptide has neurite outgrowth inhibitory action.

The amino acid substitution is preferably conservative substitution. As used herein, "conservative substitution" means replacing an amino acid residue with another chemically similar amino acid residue so as not to substantially alter the activity of the peptide. For example, substitution of one hydrophobic residue by another hydrophobic residue, substitution of one polar residue by another polar residue having the same electric charge, and the like are included. Examples of functionally similar amino acids with which such substitution is possible include, as nonpolar (hydrophobic) amino acids, alanine, valine, isoleucine, leucine, proline, tryptophan, phenylalanine and methionine. Examples of polar (neutral) amino acids include glycine, serine, threonine, tyrosine, glutamine, asparagine, and cysteine. Examples of positively charged (basic) amino acids include arginine, histidine and lysine. Examples of negatively charged (acidic) amino acids include aspartic acid and glutamic acid.

Binding of the RGMa binding protein of the present invention to RGMa means RGMa specific binding. More preferred is a RGMa-binding protein having a low dissociation constant (Kd) for human RGMa, for example, of $10^{-8}$M or less, more preferably $10^{-9}$M or less, still more preferably $10^{-10}$ M or less as the upper limit value, and for example without limitation, of $10^{-14}$ M or more, more preferably $10^{-13}$ or more as the lower limit value.

The RGMa protein comprises an N-terminal domain and a C-terminal domain as a mature protein, but has neurite outgrowth inhibitory activity with the C-terminal domain alone. The RGMa-binding protein of the present invention preferably binds only to the C-terminal domain of RGMa to neutralize neurite outgrowth inhibitory activity. More preferred is a RGMa-binding protein having a low dissociation constant (Kd) for the C-terminal domain of human RGMa, for example, of $10^{-8}$M or less, more preferably $10^{-9}$M or less, still more preferably $10^{-10}$ M or less as the upper limit value, and for example without limitation, of $10^{-14}$ M or more, more preferably $10^{-13}$ or more as the lower limit value.

The RGMa-binding protein of the present invention does not inhibit binding between RGMa and neogenin. Here, the phrase "does not inhibit binding between RGMa and neogenin" means that, in the binding system of RGMa and neogenin shown in Examples described later, even when the concentration of RGMa-binding protein is increased, the binding between RGMa and neogenin is not substantially decreased. For example, in the case where RGMa-binding protein is added to the binding system of RGMa and neogenin and its concentration is increased, if the concentration of the RGMa-binding protein showing IC50 is not less than 10 μg/mL, more preferably not less than 50 μg/mL, most preferably not less than 100 μg/mL, it can be said that the RGMa-binding protein does not inhibit the binding between RGMa and neogenin.

Neogenin used for the binding assay with RGMa is preferably neogenin of the same type as RGMa. In other words, it is preferred that mouse or human neogenin is used for mouse or human RGMa, respectively. An example of human neogenin includes a protein having the amino acid sequence of SEQ ID NO: 10 in Sequence Listing. However, as long as it is capable of binding to RGMa, a protein having an amino acid sequence with 90% or more (preferably 95% or more) identity with SEQ ID NO: 10 in Sequence Listing may be preferred.

The RGMa-binding protein of the present invention neutralizes the neurite outgrowth inhibiting activity of RGMa. The neurite outgrowth inhibitory activity can be evaluated by a neurite outgrowth assay shown in Examples described later. Addition of RGMa inhibits neurite outgrowth, but addition of RGMa-binding protein prevents neurite outgrowth inhibition by RGMa. The RGMa-binding protein of the present invention can neutralize the neurite outgrowth inhibition by addition of RGMa by 50% or more, more preferably by 80% or more, and most preferably by 90% or more.

Since amino acid sequences of RGMa proteins vary depending on the animal species, there are also differences in amino acid sequence between the human RGMa represented by SEQ ID NO: 1 in Sequence Listing, the mouse RGMa represented by SEQ ID NO: 2 in Sequence Listing, and the rat RGMa represented by SEQ ID NO: 3 in Sequence Listing. Since rodents such as mice and rats are generally used as experimental materials in pharmacological and safety tests of protein preparations such as antibody preparations, the RGMa-binding protein of the present invention preferably binds to mouse and/or rat RGMa, and more preferred are those having a low Kd for mouse and/or rat RGMa. RGMa-binding proteins whose Kd has the upper limit of, for example, $5\times10^{-7}$M or less, more preferably $10^{-8}$ M or less, still more preferably $10^{-9}$M or less, and the lower limit value of, for example without limitation, $10^{-12}$M or more, more preferably $10^{-11}$ or more are included.

The RGMa binding protein of the present invention is preferably excellent in thermal stability. The thermal stability can be evaluated by a decrease in the binding with RGMa by heat treatment, and the RGMa binding protein of the present invention is preferably stable even by heat treatment at 60° C. or higher, more preferably even by heat treatment at 65° C. or higher, most preferably even by heat treatment at 70° C. or higher.

The binding site when the RGMa binding protein of the present invention binds to RGMa is not particularly limited. For example, in human RGMa, binding to one or more of the following peptides is preferred: EEVVNAVEDWDSQG (SEQ ID NO: 26 in Sequence Listing) (amino acid numbers 298-311 of SEQ ID NO: 1 in Sequence Listing), NQQIDFQAFHTNAE (SEQ ID NO: 27 in Sequence Listing) (amino acid numbers 322-335 of SEQ ID NO: 1 in Sequence Listing), PTAPETFPYET (SEQ ID NO: 28 in Sequence Listing) (amino acid numbers 349-359 of SEQ ID NO: 1 in Sequence Listing), KLPVEDLYYQA (SEQ ID NO: 29 in Sequence Listing) (amino acid numbers 367-377 of SEQ ID NO: 1 in Sequence Listing). The RGMa binding protein of the present invention binds more preferably to SEQ ID NOS: 26 and 27 of the sequence listing, more preferably to SEQ ID NOS: 26 and 27 of the sequence listing and to SEQ ID NO: 28 or 29 of the sequence listing.

Specific examples of RGMa-binding protein include anti-RGMa antibody, RGMa-binding scaffold protein, and fusion proteins thereof.

Anti RGMa Antibody

The anti-RGMa antibody of the present invention includes polyclonal or monoclonal antibodies obtained by using the RGMa protein or a partial fragment thereof (for example, a fragment containing one or more of SEQ ID NOS: 26 to 29 in the above sequence listing) as an antigen and immunizing mammals such as mice with the antigens;

chimeric antibodies and humanized antibodies produced using gene recombination technology; human antibodies produced using, for example, human antibody-producing transgenic animals; and the like. When the antibody of the present invention is administered as a pharmaceutical to humans, a humanized antibody or a human antibody is preferable from the viewpoint of side effects.

Antigens may be directly used for immunization or may be used as a complex with a carrier protein. For preparing a complex of an antigen and a carrier protein, condensing agents such as glutaraldehyde, carbodiimide and maleimide active ester can be used. Examples of the carrier protein include bovine serum albumin, thyroglobulin, hemocyanin, and KLH.

Examples of mammals to be immunized include mice, rats, hamsters, guinea pigs, rabbits, cats, dogs, pigs, goats, horses and cattle, and inoculation methods include subcutaneous, intramuscular or intraperitoneal administration. Upon administration, antigens may be administered in admixture with complete Freund's adjuvant or incomplete Freund's adjuvant, and administration is usually carried out once every 2 to 5 weeks. Antibody-producing cells obtained from the spleen or lymph nodes of the immunized animals are fused with myeloma cells and isolated as hybridomas. As the myeloma cells, those derived from a mammal such as mouse, rat, or human are used.

Polyclonal Antibody

Polyclonal antibodies can be obtained by existing common production methods. That is, polyclonal antibodies can be obtained from serum obtained from animals subjected to immunization, for example, by immunizing a mammal as described above with an antigen as described above together with Freund's adjuvant as necessary.

Monoclonal Antibody

Specifically, monoclonal antibodies can be obtained as follows. That is, an antigen as described above is used as an immunogen, and the immunogen is injected or transplanted one or several times in combination with Freund's adjuvant, if necessary, to a mammal as described above subcutaneously, intramuscularly, intravenously, into a footpad or intraperitoneally for immunization. Generally, immunization is performed 1 to 4 times every 1 to 14 days from the initial immunization, and antibody-producing cells are obtained from the mammal immunized from about 1 to 5 days after the final immunization.

Monoclonal antibodies can be obtained using methods well known to those skilled in the art (for example, "Current Protocols in Molecular Biology" (John Wiley & Sons (1987)), Antibodies: A Laboratory Manual, Ed. Harlow and David Lane, Cold Spring Harbor Laboratory (1988))).

Preparation of "hybridomas" secreting monoclonal antibodies can be carried out according to the method of Köhler and Milstein et al. (Nature, 256, 495, 1975) and methods similar thereto. That is, Hybridomas are prepared by fusing an antibody-producing cell contained in a spleen or the like obtained from an immunized mammal with a myeloma cell having no autoantibody producing ability derived from a mammal, preferably mouse, rat or human.

Examples of myeloma cells which can be used for cell fusion include mouse-derived myeloma P3/X63-AG8.653 (653), P3/NSI/1-Ag4-1 (NS-1), P3/X63-Ag8.U1 (P3U1), SP2/0-Ag14 (Sp2/O, Sp2), PAI, FO and BW5147, rat-derived myeloma 210RCY3-Ag.2.3, and human-derived myeloma U-266AR1, GM1500-6TG-A1-2, UC729-6, CEM-AGR, D1R11 and CEM-T15.

Examples of fusion accelerators include polyethylene glycol and the like. In general, antibody-producing cells and myeloma cells at a number ratio of usually about 1:1 to 10:1 are allowed to react, using polyethylene glycol (average molecular weight: 1000 to 4000) at a concentration of about 20 to 50%, at a temperature of 20 to 40° C., preferably 30 to 37° C. for about 1 to 10 minutes, whereby cell fusion can be carried out.

Screening of hybridoma clones producing monoclonal antibodies can be carried out by culturing the hybridomas, for example, in microtiter plates and measuring the reactivity of the culture supernatants in the wells to the immunogen by immunochemical methods such as ELISA.

In the screening of the antibody-producing hybridomas, in addition to the binding assay with RGMa protein, whether the antibody does not inhibit the binding between RGMa protein and neogenin and whether the antibody neutralizes the function of RGMa protein (neurite outgrowth inhibitory activity) are also evaluated. These screening methods allow selection of the anti-RGMa antibody of the present invention.

Clones can be further obtained from the wells containing hybridomas producing the desired antibodies by cloning using limiting dilution. Selection and breeding of hybridomas are usually carried out in an animal cell culture medium containing 10 to 20% fetal bovine serum supplemented with HAT (hypoxanthine, aminopterin and thymidine).

Monoclonal antibodies from hybridomas can be produced by culturing the hybridomas in vitro or growing them in vivo, for example, in ascitic fluid of mammals such as mice and rats and isolating monoclonal antibodies from the resulting culture supernatant or the ascitic fluid of the mammal.

When cultured in vitro, hybridomas are grown, maintained, and stored in accordance with various conditions such as the characteristics of and the culture method for the cells species to be cultured, and a nutrient medium suitable for producing monoclonal antibodies in the culture supernatant can be used.

Examples of basic media include a low-calcium medium such as Ham's F12 medium, MCDB 153 medium or low-calcium MEM medium and a high-calcium medium such as MCDB 104 medium, MEM medium, D-MEM medium, RPMI 1640 medium, ASF 104 medium or RD medium. The basic media can contain, for example, serum, hormones, cytokines and/or various inorganic or organic substances according to the purpose.

Monoclonal antibodies can be isolated and purified by, for example, subjecting the above-mentioned culture supernatant or ascitic fluid to saturated ammonium sulfate, euglobulin precipitation method, caproic acid method, caprylic acid method, ion exchange chromatography (such as DEAE or DE52) or affinity column chromatography such as anti-immunoglobulin column or protein A column chromatography. Specifically, purification of the monoclonal antibody can be carried out by any methods known as immunoglobulin purification method, and can be easily achieved by means such as ammonium sulfate fractionation, PEG fractionation, ethanol fractionation, and affinity chromatography utilizing an anion exchanger and further using RGMa proteins.

Monoclonal antibodies can also be obtained by a phage display method. In the phage display method, phages selected from an optional phage antibody library are screened using the desired immunogen and phages having desired binding capacity to the immunogen are selected. Next, the antibody-corresponding sequence contained in the phage is isolated or sequenced and an expression vector comprising a nucleic acid molecule encoding an antibody or an antigen binding domain is constructed based on the isolated sequence or the determined sequence information.

Finally, monoclonal antibodies can be produced by culturing cell lines transfected with such expression vectors. A human antibody library can be used as a phage antibody library to generate human antibodies having desired binding properties.

As a scaffold protein, for example, a Kunitz domain of human serine protease inhibitor and an extracellular domain of human fibronectin are utilized, and the sequence of a target binding site on the scaffold can be modified to generate a scaffold protein which binds to RGMa (Clifford Mintz et. al BioProcess International, 2013, Vol. 11(2), pp 40-48).

Fusion proteins include RGMa-binding proteins bound chemically or genetically to function molecules other than the RGMa-binding protein of the present application such as nonpeptidic polymers such as polyethylene glycol (PEG), radioactive substances, toxins, low molecular weight compounds, cytokines, growth factors (e.g., TGF-β, NGF, neurotrophin), albumin, enzymes, and other antibodies.

When PEG is bound as a functional molecule, PEG can be used having a molecular weight of, without limitation, 2,000 to 100,000 Da, more preferably 10,000 to 50,000 Da, which may be linear or branched. By using, for example, an NHS active group, PEG can be bound, for example, to N-terminal amino groups of amino acids of the RGMa-binding protein.

In the case of using a radioactive substance as a functional molecule, for example, $^{131}$I, $^{125}$I $^{90}$Y, $^{64}$Cu, $^{99}$Tc, $^{77}$Lu or $^{211}$At is used. Radioactive substances can be directly bound to the RGMa-binding protein by, for example, chloramine-T method.

When using a toxin as a functional molecule, for example, bacterial toxins (e.g., diphtheria toxin), phytotoxins (e.g., ricin), small toxins (e.g., geldanamycin), maytansinoids and calicheamicin are used.

When using a low molecular weight compound as a functional molecule, for example, daunomycin, doxorubicin, methotrexate, mitomycin, neocarzinostatin, vindesine and fluorescent dyes such as FITC are used.

When using an enzyme as a functional molecule, for example, luciferase (e.g., firefly luciferase and bacterial luciferase; U.S. Pat. No. 4,737,456), malate dehydrogenase, urease, peroxidase (e.g., horseradish peroxidase (HRPO)), alkaline phosphatase, β-galactosidase, glucoamylase, lysozyme, saccharide oxidase (e.g., glucose oxidase, galactose oxidase and glucose-6-phosphate dehydrogenase), heterocyclic oxidase (e.g., uricase and xanthine oxidase), lactoperoxidase, and microperoxidase are used.

Examples of linkers used for chemically bonding a toxin, a low molecular weight compound or an enzyme include divalent radicals (e.g., alkylene, arylene, heteroarylene), a repeating unit of a linker or alkoxy represented by —$(CR_2)_n$ $O(CR_2)_n$— (wherein R is an optional substituent, and n is a positive integer) (e.g., polyethyleneoxy, PEG and polymethyleneoxy) and alkylamino (e.g., polyethyleneamino, Jeffamine™) and a diacid ester and amide (e.g., succinate, succinamide, diglycolate, malonate, and caproamide). Chemical modification methods for binding functional molecules have already been established in this field (D. J. King, Applications and Engineering of Monoclonal antibodies, 1998, T. J. International Ltd, Monoclonal Antibody-Based Therapy of Cancer, 1998, Marcel Dekker Inc; Chari et al., Cancer Res., 1992 Vol 152:127; Liu et al., Proc Natl Acad Sci USA, 1996 Vol 93:8681).

A preferred embodiment of the RGMa-binding protein of the present invention is a chimeric antibody. As the "chimeric antibody", a chimeric antibody in which the variable region is a variable region derived from an immunoglobulin of a non-human animal (such as mouse, rat, hamster or chicken) and the constant region is a constant region of human immunoglobulin is exemplified. A chimeric antibody can be prepared, for example, by immunizing a mouse with an antigen, cutting out a variable region that binds to the antigen from the gene encoding the mouse monoclonal antibody, and combining the variable region with a constant region of an antibody derived from human bone marrow. The constant region derived from human immunoglobulin has a unique amino acid sequence depending on the isotype such as IgG (IgG1, IgG2, IgG3 and IgG4), IgM, IgA (IgA1 and IgA2), IgD and IgE, but the constant region of the recombinant chimeric antibody according to the present invention may be a constant region of human immunoglobulin belonging to any isotype. The constant region is preferably a constant region of human IgG. An expression vector can be prepared using the gene of the chimeric antibody thus prepared. Host cells are transformed with the expression vector to obtain chimeric antibody-producing transformant cells, and then the transformed cells are cultured to obtain the desired chimeric antibody from the culture supernatant.

Another preferred embodiment of the RGMa-binding protein of the present invention is a humanized antibody. The "humanized antibody" in the present invention is an antibody obtained by grafting only the DNA sequence of the antigen binding site (CDR; complementarity determining region) of a nonhuman animal antibody such as mouse to a human antibody gene (CDR grafting). Humanized antibodies can be prepared by referring to the methods described in, for example, Japanese Translated PCT Patent Application Laid-open No. Hei 4-506458 and Japanese Patent No. 2912618. Specifically, a humanized antibody is contemplated characterized in that part or all of the CDRs are CDRs derived from monoclonal antibodies of non-human mammals (such as mouse, rat and hamster), that the framework regions of the variable region are framework regions of variable regions derived from human immunoglobulin, and that the constant regions are constant regions derived from human immunoglobulin.

The humanized antibody of the present invention can be produced, for example, as follows, but it goes without saying that the production method is not limited thereto.

For example, a recombinant humanized antibody derived from a mouse monoclonal antibody can be produced by genetic engineering with reference to Japanese Translated PCT Patent Application Laid-open Nos. Hei 4-506458 and Sho 62-296890. That is, DNA coding for mouse heavy chain CDR portion and DNA coding for mouse light chain CDR portion are isolated from hybridomas producing a mouse monoclonal antibody, and a human heavy chain gene coding for the whole region other than CDR of human heavy chain and a human light chain gene coding for the whole region other than CDR of human light chain are isolated from a human immunoglobulin gene.

The human heavy chain gene to which the isolated DNA coding for mouse heavy chain CDR portion is grafted is introduced into an appropriate expression vector so that expression thereof is possible. Similarly, the human light chain gene to which the DNA coding for mouse light chain CDR portion is grafted is introduced into another appropriate expression vector so that expression thereof is possible. Alternatively, human heavy and light chain genes to which mouse CDR is grafted may be introduced into the same expression vector so that expression thereof is possible. Host cells are transformed with the expression vector thus prepared to obtain humanized antibody-producing transformant cells, and then the transformed cells are cultured to obtain the desired humanized antibody from the culture supernatant.

Another preferred embodiment of the RGMa-binding protein of the present invention is a human antibody. A human antibody refers to an antibody in which all regions including heavy chain variable regions and heavy chain constant regions and light chain variable regions and light chain constant regions constituting the immunoglobulin are derived from genes encoding human immunoglobulin. Human antibodies can be prepared by introducing human antibody genes into mice. Human antibodies can be produced in the same manner as the above-mentioned method for preparing polyclonal antibodies or monoclonal antibodies, specifically, for example, by immunizing a transgenic animal prepared by integrating at least human immunoglobulin genes into a gene locus of a mammal other than a human such as a mouse.

For example, transgenic mice that produce human antibodies can be prepared according to the methods described, for example, in Nature Genetics, Vol. 7, p. 13-21, 1994; Nature Genetics, Vol. 15, p. 146-156, 1997; Japanese Translated PCT Patent Application Laid-open Nos. Hei 4-504365 and Hei 7-509137; WO 94/25585; Nature, Vol. 368, p. 856-859, 1994; and Japanese Translated PCT Patent Application Laid-open No. Hei 6-500233. Specific examples of the transgenic mice include HuMab™ mouse (Medarex, Princeton N.J.), KM™ mouse (Kirin Pharma Company, Japan), and KM (FCγRIIb-KO) mouse.

Specific examples of the monoclonal antibody of the present invention include those in which CDRs in the heavy chain variable region comprise the amino acid sequences of SEQ ID NOS: 33 (HCDR 1), 34 (HCDR 2) and 35 (HCDR 3) in Sequence Listing and in which CDRs in the light chain variable region comprise the amino acid sequences of SEQ ID NOS: 30 (LCDR 1), 31 (LCDR 2) and 32 (LCDR 3) in Sequence Listing. One to several amino acids in one or more of the CDRs may be substituted as long as the properties of the antibody of the present invention of having the ability to bind to RGMa, not inhibiting the binding between RGMa and neogenin, and neutralizing the neurite outgrowth inhibitory activity of RGMa are maintained. One to several means, for example, one or two. The amino acid substitution is preferably conservative substitution in order to maintain the properties of the present invention. Maintaining the properties of the antibody means that these properties are maintained to the same degree, for example, 80% or more, preferably 90% or more, more preferably 95% or more as compared with the properties before the CDR amino acid sequence modifications. Maintenance also includes improvement.

The region other than CDRs is not particularly limited as long as it is a sequence that can maintain the structure as an antibody and exert its function, and may be any of the sequences derived from mouse, human, and other mammals, chimeric sequences thereof, and artificial sequences. In the case of comprising a constant region, the amino acid sequences of the constant regions in heavy chain and light chain are exemplified by those described in Nucleic Acids Research vol. 14, p 1779, 1986, The Journal of Biological Chemistry vol. 257, p 1516, 1982 and Cell vol. 22, p 197, 1980.

Examples of mouse antibodies having these CDRs include antibodies in which the light chain has the amino acid sequence of SEQ ID NO: 4 in Sequence Listing and in which the heavy chain has the amino acid sequence of SEQ ID NO: 5 in Sequence Listing. In these amino acid sequences, there may be substitution, deletion, addition or insertion of one or several (1 to 20, 1 to 10 or 1 to 5) amino acids as long as the properties of the antibody of having the ability to bind to RGMa, not inhibiting the binding between RGMa and neogenin, and neutralizing the neurite outgrowth inhibitory activity of RGMa are maintained. Such substitution, deletion or addition may be introduced into CDRs, but it is preferably introduced into a region other than the CDRs. The amino acid substitution is preferably conservative substitution in order to maintain the properties of the present invention.

Mouse/human chimeric antibodies in which constant regions in the above-mentioned mouse antibody are derived from human are also included. An example of such mouse/human chimeric antibodies is an antibody in which the light chain has the amino acid sequence of SEQ ID NO: 8 in Sequence Listing (the variable region extends from 1 to 107) and in which the heavy chain has the amino acid sequence of SEQ ID NO: 9 in Sequence Listing (the variable region extends from 1 to 116). In these amino acid sequences, there may be substitution, deletion, addition or insertion of one or several (1 to 20, 1 to 10 or 1 to 5) amino acids as long as the properties of the antibody of having the ability to bind to RGMa, not inhibiting the binding between RGMa and neogenin, and neutralizing the neurite outgrowth inhibitory activity of RGMa are maintained. Such substitution, deletion or addition may be introduced into CDRs, but it is preferably introduced into a region other than the CDRs. The amino acid substitution is preferably conservative substitution in order to maintain the properties of the present invention.

Further, humanized antibodies in which the region other than CDRs is derived from human are exemplified. An example of such humanize antibodies is an antibody in which the heavy chain has an amino acid sequence of any one of SEQ ID NOS: 11 to 18 (the variable region is up to the 116th residue on the N terminal side) and in which the light chain has an amino acid sequence of any one of SEQ ID NOS: 19-25 in Sequence Listing (the variable region extends from the 1st to 107th residues on the N-terminal side).

In the amino acid sequences of the humanized antibody (heavy chain: SEQ ID NOS: 11-18 in Sequence Listing, light chain: SEQ ID NOS: 19 to 25 in Sequence Listing), there may be substitution, deletion, addition or insertion of one or several (1 to 20, 1 to 10 or 1 to 5) amino acids as long as the properties of the antibody of having the ability to bind to RGMa, not inhibiting the binding between RGMa and neogenin, and neutralizing the neurite outgrowth inhibitory activity of RGMa are maintained. Such substitution, deletion or addition may be introduced into CDRs, but it is preferably introduced into a region other than the CDRs. The amino acid substitution is preferably conservative substitution in order to maintain the properties of the present invention.

The heavy chain amino acid sequence and the light chain amino acid sequence may be any combination thereof, but particularly preferred is an antibody having heavy chains comprising the amino acid sequence of SEQ ID NO: 15 in Sequence Listing and light chains comprising the amino acid sequence of SEQ ID NO: 19 in Sequence Listing. In the amino acid sequence of SEQ ID NO: 15 in Sequence Listing, the amino acid sequence corresponding to the heavy chain variable region is shown in SEQ ID NO: 41 in Sequence Listing and the amino acid sequence corresponding to the light chain variable region is shown in SEQ ID NO: 42 in Sequence Listing. Thus, the particularly preferred antibody of the present invention is an antibody in which the heavy chain variable region has the amino acid sequence of SEQ ID NO: 41 in Sequence Listing and in which the light chain variable region has the amino acid sequence of SEQ ID NO: 42 in Sequence Listing.

In these amino acid sequences, there may be substitution, deletion, addition or insertion of one or several (1 to 20, 1 to 10 or 1 to 5) amino acids as long as the properties of the antibody of having the ability to bind to RGMa, not inhibiting the binding between RGMa and neogenin, and neutralizing the neurite outgrowth inhibitory activity of RGMa are maintained. Such substitution, deletion or addition may be introduced into CDRs, but it is preferably introduced into a region other than the CDRs. The amino acid substitution is preferably conservative substitution in order to maintain the properties of the present invention.

In the amino acid sequence of the antibody of the present invention comprising substitution, deletion or the like in the amino acid sequence of SEQ ID NO: 41 and/or 42 in Sequence Listing as described above, the heavy chain variable region is an amino acid sequence having 90% or more (more preferably 95%, 96%, 97%, 98%, 99% or more) identity with SEQ ID NO: 41 of the sequence listing, and the light chain variable region is an amino acid sequence having 90% or more (more preferably 95%, 96%, 97%, 98%, 99% or more) identity with SEQ ID NO: 42 of the sequence listing.

Other specific examples of the monoclonal antibody of the present invention include those in which CDRs in the heavy chain variable region comprise the amino acid sequences of SEQ ID NOS: 39 (HCDR 1), 40 (HCDR 2) and SFG (HCDR 3) in Sequence Listing and in which CDRs in the light chain variable region comprise the amino acid sequences of SEQ ID NOS: 36 (LCDR 1), 37 (LCDR 2) and 38 (LCDR 3) in Sequence Listing. One to several amino acids in one or more of the CDRs may be substituted as long as the properties of the antibody of the present invention of having the ability to bind to RGMa, not inhibiting the binding between RGMa and neogenin, and neutralizing the neurite outgrowth inhibitory activity of RGMa are maintained.

One to several means, for example, one or two. The amino acid substitution is preferably conservative substitution in order to maintain the properties of the present invention.

The region other than CDRs is not particularly limited as long as it is a sequence that can maintain the structure as an antibody and exert its function, and may be any of the sequences derived from mouse, human, and other mammals, chimeric sequences thereof, and artificial sequences. In the case of comprising a constant region, the amino acid sequences of the constant regions in heavy chain and light chain are exemplified by those described in Nucleic Acids Research vol. 14, p 1779, 1986, The Journal of Biological Chemistry vol. 257, p 1516, 1982 and Cell vol. 22, p 19'7, 1980.

Examples of mouse antibodies having these CDRs include antibodies in which the light chain has the amino acid sequence of SEQ ID NO: 6 in Sequence Listing and in which the heavy chain has the amino acid sequence of SEQ ID NO: 7 in Sequence Listing. In these amino acid sequences, there may be substitution, deletion, addition or insertion of one or several (1 to 20, 1 to 10 or 1 to 5) amino acids as long as the properties of the antibody of having the ability to bind to RGMa, not inhibiting the binding between RGMa and neogenin, and neutralizing the neurite outgrowth inhibitory activity of RGMa are maintained. Such substitution, deletion or addition may be introduced into CDRs, but it is preferably introduced into a region other than the CDRs.

The amino acid substitution is preferably conservative substitution in order to maintain the properties of the present invention.

As the above-mentioned mouse antibody, chimeric antibodies whose constant regions are derived from human are also included. Humanized antibodies in which the region other than CDRs is derived from human are further included.

The anti-RGMa antibody of the present invention includes multispecific antibodies, functionally modified antibodies, and conjugated antibodies having CDRs comprising specific amino acid sequences (for example, amino acid sequences of SEQ ID NO: 30 in Sequence Listing for LCDR1, SEQ ID NO: 31 in Sequence Listing for LCDR2, SEQ ID NO: 32 in Sequence Listing for LCDR3, SEQ ID NO: 33 in Sequence Listing for HCDR1, SEQ ID NO: 34 in Sequence Listing for HCDR2, and SEQ ID NO: 35 in Sequence Listing for HCDR3), or having variable regions comprising specific amino acid sequences (for example, amino acid sequences of SEQ ID NO: 41 in Sequence Listing for heavy chain variable region, and SEQ ID NO: 42 for light chain variable region).

The anti-RGMa antibody of the present invention itself can be bound to an antibody having another antigen binding specificity other than anti-RGMa specificity by genetic engineering techniques to prepare multispecific antibodies such as bispecific antibodies. The genetic engineering techniques have already been established in this field. For example, by using a technique for DVD-Ig in which variable regions are connected in series (Wu et al., Nature Biotechnology 25(11), 1290 (2007)) or a technique for ART-Ig in which heavy chains of two types of antibodies binding to different antigens are combined by modifying the Fc region of an antibody (Kitazawa et al., Nature Medicine 18(10), 1570(2012), desired bispecific antibodies can be obtained. Other antigens than RGMa include, but not limited to, factors inhibiting neurite outgrowth such as Nogo, MAG, Omgp, CSPG, Sema 3A and Lingo-1, and immune-related molecules such as TNF-α, IL-6 receptor, CD3, CD20, α4 integrin, BLys, Thymic Stromal Lymphopoietin, IgE, IL-1, IL-2, IL-4, IL-5, IL-6, IL-13, IL-17, IL-23 and IL-25.

Functionally modified antibodies are exemplified as modified molecules of the anti-RGMa antibody of the present invention. Functionally modified antibody means an antibody in which functions such as cell killing function, complement activating function and function to extend blood half-life are modified mainly by modifying the Fc region or the like (Shitara, Journal of the Pharmaceutical Society of Japan, 2009, Vol. 129(1), p 3; Ishii et al., Nippon Yakubutsugaku Zasshi (Folia Pharmacologica Japonica), 2010, Vol. 136(5), p 280; Hashiguchi et al., The Journal of Japanese Biochemical Society, 2010, Vol. 82(8), p'710).

Functionally modified antibodies of the anti-RGMa antibody are prepared by the following method. For example, when the anti-RGMa antibody of the present application is produced using, as host cells, CHO cells whose α1,6-fucosyltransferase (FUT 8) gene has been disrupted, antibodies with reduced content of sugar chain fucose and increased cell killing function are obtained, and when the anti-RGMa antibody of the present application is produced using, as a host cell, CHO cells into which FUT8 gene has been introduced, antibodies with low cell killing function are obtained (WO 2005/035586, WO 2002/31140 and WO 00/61739). The complement activation function can be regulated by modifying amino acid residues in the Fc region (U.S. Pat. Nos. 6,737,056, 7,297,775 and 7,317,091). The blood half-life extension can be achieved by using Fc region variants with increased binding to FcRn which is one of Fc receptors (Hashiguchi et al., The Journal of Japanese Biochemical Society, 2010, Vol. 82 (8), p'710). These functionally modified antibodies can be produced by genetic engineering techniques.

Conjugated antibodies are exemplified as modified molecules of the anti-RGMa antibody of the present invention. Examples of the conjugated antibody include conjugated antibodies in which anti-RGMa antibodies are bound chemically or genetically to function molecules other than the anti-RGMa antibody in the present application such as nonpeptidic polymers such as polyethylene glycol (PEG), radioactive substances, toxins, low molecular weight compounds, cytokines, growth factors (e.g., TGF-β, NGF, neurotrophin), albumin, enzymes, and other antibodies.

When PEG is bound as a functional molecule, PEG can be used having a molecular weight of, without limitation, 2,000 to 100,000 Da, more preferably 10,000 to 50,000 Da, which may be linear or branched. By using, for example, an NHS active group, PEG can be bound, for example, to N-terminal amino groups of amino acids of antibodies.

In the case of using a radioactive substance as a functional molecule, for example, $^{131}$I, $^{125}$I, $^{90}$Y, $^{64}$Cu, $^{99}$Tc, $^{77}$Lu or $^{211}$At is used. Radioactive substances can be directly bound to antibodies by, for example, chloramine-T method.

When using a toxin as a functional molecule, for example, bacterial toxins (e.g., diphtheria toxin), phytotoxins (e.g., ricin), small toxins (e.g., geldanamycin), maytansinoids and calicheamicin are used.

When using a low molecular weight compound as a functional molecule, for example, daunomycin, doxorubicin, methotrexate, mitomycin, neocarzinostatin, vindesine and fluorescent dyes such as FITC are used.

When using an enzyme as a functional molecule, for example, luciferase (e.g., firefly luciferase and bacterial luciferase; U.S. Pat. No. 4,737,456), malate dehydrogenase, urease, peroxidase (e.g., horseradish peroxidase (HRPO)), alkaline phosphatase, β-galactosidase, glucoamylase, lysozyme, saccharide oxidase (e.g., glucose oxidase, galactose oxidase and glucose-6-phosphate dehydrogenase), heterocyclic oxidase (e.g., uricase and xanthine oxidase), lactoperoxidase, and microperoxidase are used.

Examples of linkers used for chemically bonding a toxin, a low molecular weight compound or an enzyme include divalent radicals (e.g., alkylene, arylene, heteroarylene), a repeating unit of a linker or alkoxy represented by —(CR$_2$)$_n$O(CR$_2$)n— (wherein R is an optional substituent, and n is a positive integer) (e.g., polyethyleneoxy, PEG and polymethyleneoxy) and alkylamino (e.g., polyethyleneamino, Jeffamine™) and a diacid ester and amide (e.g., succinate, succinamide, diglycolate, malonate, and caproamide). Chemical modification methods for binding functional molecules have already been established in this field (D. J. King, Applications and Engineering of Monoclonal antibodies, 1998 T. J. International Ltd, Monoclonal Antibody-Based Therapy of Cancer, 1998 Marcel Dekker Inc; Chari et al., Cancer Res., 1992 Vol 152:127; Liu et al., Proc Natl Acad Sci USA, 1996 Vol 93:8681).

"Antigen binding fragments" of antibodies in the present invention means a partial region having antigen binding property, of the above-described antibodies, including, in particular, F(ab')$_2$, Fab', Fab, Fv (variable fragment of antibody), disulfide-linked Fv, single-chain antibody (scFv), and polymers thereof. Antigen-binding fragments further include conjugated antigen-binding fragments bound chemically or genetically to function molecules other than the anti-RGMa antibody in the present application such as nonpeptidic polymers such as polyethylene glycol (PEG), radioactive substances, toxins, low molecular weight compounds, cytokines, growth factors (e.g., TGF-β, NGF, neurotrophin), albumin, enzymes, and other antibodies.

As used herein, "F (ab')$_2$" and "Fab" means antibody fragments which are produced by treating immunoglobulins with a protease pepsin or papain and are generated by digestion upstream and downstream of the disulfide bond existing between two heavy chains in the hinge region. For example, papain treatment of IgG can cause cleavage upstream of the disulfide bond existing between two heavy chains in the hinge region to produce of two homologous antibody fragments each comprising a light chain comprising a VL (light chain variable region) and a CL (light chain constant region) and a heavy chain fragment comprising a VH (heavy chain variable region) and a CHγ1 (γ1 region within heavy chain constant region) in which the light chain and the heavy chain fragment are linked to each other via a disulfide bond at C-terminal domain. Each of the two homologous antibody fragments is referred to as Fab. Pepsin treatment of IgG can cause cleavage downstream of the disulfide bond existing between two heavy chains in the hinge region to produce an antibody fragment slightly larger than one in which the two Fabs are linked to each other at the hinge region. This antibody fragment is referred to as F(ab')$_2$.

Conjugated antigen-binding fragments are exemplified as modified molecules of the antigen-binding fragment of the anti-RGMa antibody of the present invention. Examples of the conjugated antigen-binding fragment include those in which a partial region having the antigen-binding property of the anti-RGMa antibody is bound chemically or genetically to a function molecule other than the anti-RGMa antibody in the present application such as nonpeptidic polymers such as polyethylene glycol (PEG), radioactive substances, toxins, low molecular weight compounds, cytokines, growth factors (e.g., TGF-β, NGF, neurotrophin), albumin, enzymes, and other antibodies.

When PEG is bound as a functional molecule, PEG can be used having a molecular weight of, without limitation 2,000 to 100,000 Da, more preferably 10,000 to 50,000 Da, which may be linear or branched. PEG can be bound, for example, to the N-terminal amino group of a partial region having the antigen-binding property of the anti-RGMa antibody by using, for example, an NHS active group.

In the case of using a radioactive substance as a functional molecule, for example, $^{131}$I, $^{125}$I, $^{90}$Y, $^{64}$Cu, $^{99}$Tc, $^{77}$Lu or $^{211}$At is used. Radioactive substances can be directly bound to a partial region having the antigen-binding property of the anti-RGMa antibody by, for example, chloramine-T method.

When using a toxin as a functional molecule, for example, bacterial toxins (e.g., diphtheria toxin), phytotoxins (e.g., ricin), small toxins (e.g., geldanamycin), maytansinoids and calicheamicin are used.

When using a low molecular weight compound as a functional molecule, for example, daunomycin, doxorubicin, methotrexate, mitomycin, neocarzinostatin, vindesine and fluorescent dyes such as FITC are used.

When using an enzyme as a functional molecule, for example, luciferase (e.g., firefly luciferase and bacterial luciferase; U.S. Pat. No. 4,737,456), malate dehydrogenase, urease, peroxidase (e.g., horseradish peroxidase (HRPO)), alkaline phosphatase, β-galactosidase, glucoamylase, lysozyme, saccharide oxidase (e.g., glucose oxidase, galactose oxidase and glucose-6-phosphate dehydrogenase), heterocyclic oxidase (e.g., uricase and xanthine oxidase), lactoperoxidase, and microperoxidase are used.

Examples of linkers used for chemically bonding a toxin, a low molecular weight compound or an enzyme include divalent radicals (e.g., alkylene, arylene, heteroarylene), a repeating unit of a linker or alkoxy represented by —(CR$_2$)$_n$O(CR$_2$)$_n$— (wherein R is an optional substituent, and n is a positive integer) (e.g., polyethyleneoxy, PEG and polymethyleneoxy) and alkylamino (e.g., polyethyleneamino, Jeffamine™) and a diacid ester and amide (e.g., succinate, succinamide, diglycolate, malonate, and caproamide). Chemical modification methods for binding functional molecules have already been established in this field (D. J. King, Applications and Engineering of Monoclonal antibodies, 1998 T. J. International Ltd, Monoclonal Antibody-Based Therapy of Cancer, 1998 Marcel Dekker Inc; Chari et al., Cancer Res., 1992 Vol152:127; Liu et al., Proc Natl Acad Sci USA, 1996 Vol 93:8681).

In the anti-RGMa antibody comprising CDRs or variable regions having the specific amino acid sequences of the present invention, the constant region preferably is a constant region of human IgG (IgG1, IgG2, IgG3 or IgG4) for maintenance with a long half-life in blood.

The present invention also includes an anti-RGMa antibody which competes with the antibody having the amino acid sequences of the specific CDRs as described above for binding to RGMa proteins, and antigen binding fragments thereof. The antibody which competes with the antibody having the amino acid sequences of the specific CDRs as described above for binding to RGMa proteins include epitopes in the regions selected from Glu 298 to Gly 311, Asn 322 to Glu 335, Lys 367 to Ala 377, and Pro 349 to Thr 359.

The antibody can be obtained (screened) or evaluated by allowing the antibody to coexist in the binding system of the antibody having the CDR sequences as described above and RGMa proteins. For example, the antibody can be obtained by screening using the following surface plasmon resonance (SPR) method.

Biotinylated human RGMa protein (4 μg/mL) as a ligand is loaded on an avidin-immobilized sensor chip to immobilize human RGMa proteins equivalent to 1300 to 1600 RU. Next, an optional anti-RGMa antibody (15 μg/mL) is loaded as an analyte and bound to the human RGMa protein immobilized on the sensor chip. By repeating this a plurality of times, a state in which the optional anti-RGMa antibody is bound to all of the human RGMa protein molecules on the sensor chip is created (saturated state) and the amount of binding in the saturated state (saturated binding amount 1) is determined.

A similar experiment is carried out with the anti-RGMa antibody comprising the amino acid sequences of the specific CDRs of the present invention to determine the amount of binding in the saturated state (saturated binding amount 2).

Next, the human RGMa proteins on the sensor chip are saturated with the anti-RGMa antibody comprising the amino acid sequences of the specific CDRs of the present invention, and then an optional anti-RGMa antibody (15 μg/mL) is loaded as an analyte to investigate whether the optional anti-RGMa antibody binds additionally to the human RGMa protein saturated with the anti-RGMa antibody comprising the amino acid sequences of the specific CDRs of the invention.

If the optional anti-RGMa antibody can bind additionally to the human RGMa protein saturated with the anti-RGMa antibody comprising the amino acid sequences of the specific CDRs of the invention while showing the saturated binding amount 1 of an optional anti-RGMa antibody calculated above, then the antibody is judged as "not competing". On the other hand, if the optional anti-RGMa antibody can not bind additionally to the human RGMa protein saturated with the anti-RGMa antibody comprising the amino acid sequences of the specific CDRs of the invention, then the antibody is judged as "competing". Even if the optional anti-RGMa antibody can bind additionally to the human RGMa protein saturated with the anti-RGMa antibody comprising the amino acid sequences of the specific CDRs of the invention, when the added binding amount does not reach the saturated binding amount 1 with a significant difference, then the antibody is judged as "competing". Significant differences are examined by general statistical methods (for example, Student's t-test), and the significance level is set to 5% or less.

The anti-RGMa antibody which competes with an anti-RGMa antibody comprising the specific CDR amino acid sequence as described above for binding with RGMa may be an antibody derived from any animal such as mouse, human, rat, rabbit, goat, or camel antibody, or may be a chimeric or humanized antibody which is a combination of these antibodies, but preferably is a chimeric, humanized, or human antibody.

Nucleic Acid Molecules of the Present Invention

Examples of the nucleic acid molecules of the present invention include polynucleotides in which the region encoding a heavy chain variable region comprises a base sequence encoding the amino acid sequence of SEQ ID NOS: 33, 34, and 35 in Sequence Listing, respectively (in which one or several amino acids may be substituted, deleted, inserted or added) and the region encoding a light chain variable region comprises a base sequence encoding the amino acid sequence of SEQ ID NOS: 30, 31, and 32 in Sequence Listing, respectively (in which one or several amino acids may be substituted, deleted, inserted or added); and polynucleotides in which the region encoding a heavy chain variable region comprises a base sequence encoding the amino acid sequence of SEQ ID NOS: 39, 40, and SFG in Sequence Listing, respectively (in which one or several amino acids may be substituted, deleted, inserted or added) and the region encoding a light chain variable region comprises a base sequence encoding the amino acid sequence of SEQ ID NOS: 36, 37, and 38 in Sequence Listing, respectively (in which one or several amino acids may be substituted, deleted, inserted or added).

Other examples of the nucleic acid molecule of the present invention include polynucleotides in which the region encoding a heavy chain comprises a base sequence encoding the amino acid sequence of SEQ ID NO: 5 in Sequence Listing and the region encoding a light chain comprises a base sequence encoding the amino acid sequence of SEQ ID NO: 4 in Sequence Listing; and polynucleotides in which the region encoding a heavy chain comprises a base sequence encoding the amino acid sequence of SEQ ID NO: 7 in Sequence Listing and the region encoding a light chain comprises a base sequence encoding the amino acid sequence of SEQ ID NO: 6 in Sequence Listing.

Other examples of the nucleic acid molecule of the present invention include polynucleotides in which the region encoding a heavy chain comprises a base sequence encoding the amino acid sequence of SEQ ID NO: 9 in Sequence Listing and the region encoding a light chain comprises a base sequence encoding the amino acid sequence of SEQ ID NO: 8 in Sequence Listing.

Other examples of the nucleic acid molecule of the present invention include polynucleotides in which the region encoding a heavy chain comprises a base sequence encoding the amino acid sequence of any one of SEQ ID NOS: 11 to 18 in Sequence Listing and the region encoding a light chain comprises a base sequence encoding the amino acid sequence of any one of SEQ ID NOS: 19 to 25 in Sequence Listing.

Particularly preferred examples of the nucleic acid molecule of the present invention include polynucleotides in which the region encoding a heavy chain comprises a base sequence encoding the amino acid sequence of SEQ ID NO: 15 in Sequence Listing and the region encoding a light chain comprises a base sequence encoding the amino acid sequence of SEQ ID NO: 19 in Sequence Listing.

Other examples of the nucleic acid molecule of the present invention include polynucleotides in which the region encoding a heavy chain variable region comprises a base sequence encoding the amino acid sequence of SEQ ID NO: 41 in Sequence Listing and the region encoding a light chain variable region comprises a base sequence encoding the amino acid sequence of SEQ ID NO: 42 in Sequence Listing.

Specific examples of the nucleic acid molecule of the present invention include polynucleotides in which the region encoding a heavy chain variable region comprises the base sequence of SEQ ID NO: 43 in Sequence Listing and the region encoding a light chain variable region comprises the base sequence of SEQ ID NO: 44 in Sequence Listing.

The nucleic acid molecule of the present invention may be polynucleotides which hybridizes under stringent conditions to a complementary strand DNA having the base sequence of SEQ ID NO: 43 in Sequence Listing and polynucleotides which hybridizes under stringent conditions to a complementary strand DNA having the base sequence of SEQ ID NO: 44 in Sequence Listing as long as the nucleic acid molecule of the present invention encodes a monoclonal antibody which has ability to bind to RGMa, does not inhibit the binding between RGMa and neogenin, and neutralizes the neurite outgrowth inhibitory activity of RGMa. Examples of the stringent conditions include a condition of conducting southern hybridization and washing at a salt concentration corresponding to 0.1×SSC, 0.1% SDS at 68° C.

The nucleic acid molecule of the present invention may encode all of the constant regions and the variable regions of heavy and light chains, and may encode only the variable regions of heavy and light chains. The base sequence of the constant region of heavy and light chains in the case of encoding all of the constant region and the variable region is preferably those described in Nucleic Acids Research vol. 14, p 1779, 1986, The Journal of Biological Chemistry vol. 257, p 1516, 1982 and Cell vol. 22, p 197, 1980.

The nucleic acid molecule of the present invention can be obtained, for example, by the following method. First, total RNA is prepared from cells such as hybridomas using a commercial RNA extraction kit, and cDNA is synthesized with reverse transcriptase using random primers or the like. Next, cDNAs encoding the antibody are amplified by a PCR method using, for primers, oligonucleotides having sequences conserved in the variable regions of known human antibody heavy and light chain genes, respectively. For the sequence encoding the constant region, it can be obtained by amplifying the known sequence by PCR method. The base sequence of the DNA can be determined by a conventional method, for example by incorporating it into a plasmid for sequencing.

Alternatively, a DNA encoding the monoclonal antibody of the present invention can also be obtained by chemically synthesizing a sequence of the variable region or a part thereof and binding it to a sequence comprising the constant region.

The present invention also provides a recombinant vector comprising the nucleic acid molecule of the present invention and a transformant (host cell) comprising the recombinant vector. The recombinant vector may be vectors which can be expressed in prokaryotic cells such as *E. coli* (*Escherichia coli*) (e.g., pBR322, pUC119 or a derivative thereof), and preferably are vectors which can be expressed in eukaryotic cells, and more preferably are vectors which can be expressed in mammalian-derived cells. Examples of the vectors which can be expressed in mammalian-derived cells include plasmid vectors such as pcDNA 3.1 (Invitrogen), pConPlus, pcDM8, pcDNA I/Amp, pcDNA 3.1, pREP4; and viral vectors such as pDON-AI DNA (Takara Bio). The vector may be one vector comprising a heavy chain coding sequence and a light chain coding sequence or may be two vectors of a vector comprising a heavy chain coding sequence and a vector comprising a light chain coding sequence.

The transformant into which the recombinant vector of the present invention is introduced may be a prokaryotic cell such as *Escherichia coli* or *Bacillus subtilis*, preferably a eukaryotic cell, more preferably a mammalian cell. Examples of the mammalian cell include Chinese hamster ovary cells (CHO cells), COS, myeloma, BHK, HeLa, Vero, 293, NS0, Namalwa and YB2/0.

The anti-RGMa antibody or antigen-binding fragment thereof obtained can be purified to homogeneity. Separation and purification methods used for ordinary proteins may be used for separation and purification of antibodies and the like. Separation and purification of antibodies can be achieved by appropriately selecting and combining, for example, but not limited to, chromatography columns such as affinity chromatography, filters, ultrafiltration, salting out, dialysis, SDS polyacrylamide gel electrophoresis or isoelectric focusing (Antibodies: A Laboratory Manual. Ed Harlow and David Lane, Cold Spring Harbor Laboratory, 1988). Examples of columns used for affinity chromatography include protein A column, protein G column, anti-immunoglobulin antibody-conjugated column and antigen-conjugated column. Examples of the protein A column include Hyper D, POROS and Sepharose F. F. (Amersham Biosciences).

Agents for Preventing or Treating Immunological and Neurological Diseases

The RGMa-binding protein, particularly the anti-RGMa antibody or antigen-binding fragment thereof of the present invention neutralizes the neurite outgrowth inhibitory activity of RGMa to promote the repair of neuronal function and thus can be used as an agent for preventing, treating, or preventing the relapse of neurological diseases.

The RGMa-binding protein, particularly the anti-RGMa antibody or antigen-binding fragment thereof of the present invention also neutralizes T-cell activation by RGMa and thus can be used as an agent for preventing, treating, or preventing the relapse of immunological diseases.

Examples of the neurological disease include amyotrophic lateral sclerosis, brachial plexus injury, brain damage (including traumatic brain injury), cerebral palsy, Guillain-Barre syndrome, cerebral leukodystrophy, multiple sclerosis (including relapsing-remitting multiple sclerosis, primary progressive multiple sclerosis, secondary progressive multiple sclerosis), neuromyelitis optica, post-polio syndrome, spina bifida, spinal cord injury, spinal muscular atrophy, spinal neoplasm, transverse myelitis, dementia (including senile dementia, mild cognitive impairment, Alzheimer's disease, dementia associated with Alzheimer's disease), Huntington's disease, tardive dyskinesia, mania, Parkinson's disease, Steele-Richardson syndrome, Down's syndrome, myasthenia gravis, neurotrauma (including optic nerve trauma), vascular amyloidosis, cerebral hemorrhage associated with amyloidosis, brain infarction, cerebritis, acute confusional state, glaucoma, schizophrenia and retinal nerve fiber layer degeneration (including diabetic retinopathy, ischemic optic neuropathy, X-linked retinoschisis, drug-induced optic neuropathy, retinal dystrophy, age-related macular degeneration, eye diseases characterized by optic disc drusen, eye diseases characterized by genetic determinant for photoreceptor degeneration, autosomal recessive cone-rod dystrophy, mitochondrial disorder associated with optic neuropathy). Spinal cord injury and neurotrauma (including optic nerve trauma) are preferred.

Examples of the immunological disease include multiple sclerosis (including relapsing-remitting multiple sclerosis, primary progressive multiple sclerosis, secondary progressive multiple sclerosis), neuromyelitis optica, psoriasis, arthritis (including rheumatoid arthritis, osteoarthritis, psoriatic arthritis), Guillain-Barre syndrome, neuro-Behcet disease, pernicious anemia, type I (insulin-dependent) diabetes mellitus, systemic lupus erythematosus (SLE), inflammatory bowel disease (IBD), Sjogren's syndrome, Goodpasture's syndrome, Graves' disease, autoimmune hemolytic anemia, autoimmune thrombocytopenic purpura, asthma, pollinosis, atopic dermatitis, glomerulonephritis, myasthenia gravis, Hashimoto's disease, and sarcoidosis. Multiple sclerosis is preferred.

The RGMa-binding protein, particularly the anti-RGMa antibody or antigen-binding fragment thereof of the present invention can be used as an agent for preventing, treating, or preventing the relapse of neurological/immunological diseases, which preferably include spinal cord injury, neurotrauma (including optic nerve trauma) and multiple sclerosis (including relapsing-remitting multiple sclerosis, primary progressive multiple sclerosis, secondary progressive multiple sclerosis).

As used herein, the term "treating" includes any treatment of diseases in a mammal, particularly a human, and includes inhibiting disease symptoms, that is, inhibiting their progression or eliminating the diseases or symptoms, and alleviating disease symptoms, that is, causing regression of the diseases or symptoms or a delay in the development of the symptoms.

"Preventing" includes prevention of onset of the above-described diseases in a mammal, particularly a human.

"Preventing the relapse" includes prevention of relapse of the above-described diseases repeating remission and relapse in a mammal, particularly a human.

The RGMa-binding protein (anti-RGMa antibody or antigen-binding fragment thereof) of the present invention can be used as a pharmaceutical composition for preventing or treating neurological or immunological diseases.

The administration form of the RGMa-binding protein (anti-RGMa antibody or antigen-binding fragment thereof) of the present invention is not particularly limited and can be administered to mammals including humans by any route of oral or parenteral administration (e.g., intravenous, intramuscular, subcutaneous, rectal, transcutaneous, intracerebral, intraspinal or other topical administration).

Dosage forms for oral and parenteral administration and preparation methods thereof are well known to those skilled in the art, and a pharmaceutical composition can be prepared by combining the antibody according to the invention with a pharmaceutically acceptable carrier or the like.

Dosage forms for parenteral administration include injectable preparations (e.g., drip injections, intravenous injections, intramuscular injections, subcutaneous injections, intradermal injections, intracerebral administration preparations, and intraspinal administration preparations), external preparations (e.g., ointments, poultices, and lotions), suppository inhalants, eye drops, ophthalmic ointments, nasal drops, ear drops, and liposomes. In particular, when the antibody according to the present invention is to be directly acted on a central nervous tissue, it can be infused continuously using a medical micropump which is an osmotic pump, or mixed with fibrin glue or the like to prepare a sustained-release preparation and then placed in the affected tissue.

For example, injectable preparations are usually prepared by dissolving the antibody in injectable distilled water and, if necessary, a solubilizing agent, a buffer, a pH adjusting agent, an isotonizing agent, a soothing agent, a preservative, and a stabilizing agent may be added. The injectable preparations may also be lyophilized preparations prepared before use.

Dosage forms for oral administration include solid or liquid dosage forms, in particular, tablets, coated tablets, pills, fine granules, granules, powders, capsules, syrups, emulsions, suspensions, injections and troches.

The pharmaceutical composition of the present invention may further contain other therapeutically effective drugs, and if necessary, components such as microbicides, antiphlogistics, vitamins and amino acids may be blended.

Pharmacologically acceptable carriers include, for example, excipients, lubricants, binders and disintegrants for solid preparations; and solvents, solubilizing agents, suspending agents, isotonizing agents, buffers and soothing agents for liquid preparations. If necessary, additives such as usual antiseptics, antioxidants, colorants, sweeteners, adsorbents, and wetting agents may be appropriately used in appropriate amounts.

The dosage of the antibody according to the present invention can be determined based on various factors such as the route of administration, the type of disease, the degree of symptoms, age, sex, body weight, severity of disease of patients, pharmacological findings such as pharmacokinetic and toxicological characteristics, whether or not a drug delivery system is used, and whether or not it is administered as a part of a combination with other drugs. Usually, 1 to 5,000 µg/day, preferably 10 to 2,000 µg/day, more preferably 50 to 2,000 µg/day for oral administration or 1 to 5,000 µg/day, preferably 5 to 2,000 µg/day, more preferably 50 to 2,000 µg/day for injection can be administered per adult (60 kg body weight) in one or several doses. For parenteral administration to the whole body, 10 to 100,000 µg/kg, more preferably 100 to 50,000 µg/kg, and even more preferably 500 to 20,000 µg/kg per body weight can be administered at an interval of once a day, once a week, once a month, or 1 to 7 times a year. For topical administration using an osmotic pump or the like, in usual, continuous infusion at a rate of 10 to 100,000 µg/day, more preferably 100 to 10,000 µg/day, still more preferably 500 to 5,000 µg/day per adult (60 kg body weight) is possible.

EXAMPLES

The present invention will be described in detail below with reference to Examples, but the present invention is not limited to the aspects of the following Examples.

Example 1: Preparation of Human RGMa Protein (C-terminal Domain)

A CHO cell expressing a recombinant human RGMa protein in which a histidine tag was fused to the C terminus of Pro 169 to Gly 422 (which refers to the proline residue at position 169 to the glycine residue at position 422 from the N-terminal side, hereinafter similarly described) of the human RGMa protein (SEQ ID NO: 1 in Sequence Listing) was established.

The C-terminal domain of the human RGMa protein contained in the culture supernatant of CHO cells was adsorbed on a nickel column (GE Healthcare, 17-5247-01), and eluted with a 100 mM imidazole solution. By dialysis, the imidazole elution fraction was replaced with Phosphate buffered Saline (PBS) and used as an immunogen.

Example 2: Preparation of Mouse Anti-human RGMa Monoclonal Antibody

Ten microgram of the recombinant human RGMa protein prepared in Example 1 was mixed with complete Freund's adjuvant (Sigma) to prepare an emulsion, and a BALB/c mouse (Charles River Japan) was immunized therewith at several subcutaneous sites on the back. Thereafter, immunization was carried out similarly at 1 to 2 week intervals with 10 μg of recombinant human RGMa protein prepared into an emulsion with incomplete Freund's adjuvant (Sigma), and blood was collected after several immunizations. Antibody titer was measured by ELISA described below in which human or mouse RGMa proteins were immobilized. Into individuals which showed an increased antibody titer, 10 μg of human RGMa protein was intravenously administered for boosting, and splenocytes were recovered 2 or 3 days later.

For cell fusion, the spleen cells and mouse myeloma cells (SP2/0, Dainippon Sumitomo Pharma) with half the number of the spleen cells were mixed and centrifuged, and polyethylene glycol (Roche Diagnostics) was added to the resulting precipitate fraction to obtain cell fusions. The cells were then centrifuged and washed twice with D-MEM (Invitrogen). The cells were resuspended in GIT medium (Nippon Pharmaceutical) containing 10% fetal bovine serum (Invitrogen), 1% BM condimed (Roche Diagnostics) and HAT (Sigma-Aldrich) and seeded in each well of a 96-well plate at $5\times10^4$ myeloma cells/well. The culture supernatant was recovered and screened for antibody-producing cells by the human RGMa protein-immobilized ELISA of Example 3.

Antibody-producing cells obtained by the screening were cloned by the limiting dilution method, and hybridoma cells producing two kinds of monoclonal antibodies (B5.116A3 and B5.70E4) were selected.

Isotypes of both of the monoclonal antibodies determined by using an isotyping kit (Mouse MonoAB ID/SP KIT, ZYMED, 93-6550) were mouse IgG2b for heavy chain and kappa for light chain.

The culture supernatants of the hybridomas were subjected to affinity chromatography using agarose on which anti-mouse IgG antibodies were immobilized (Anti-Mouse IgG-Agarose manufactured by Sigma) to purify the monoclonal antibodies. After the antibody was bound to the column, the column was washed with PBS. Then the antibody was eluted with 10 mM glycine hydrochloride (pH 2.7) and the eluate was neutralized immediately. Thereafter, the neutralized elute was replaced with PBS through an ultrafilter.

Example 3: ELISA on Which Human or Mouse RGMa Proteins are Immobilized

Human RGMa protein (R&D systems, 2459-RM) or mouse RGMa protein (R&D systems, 2458-RG) prepared at 2 μg/mL with PBS was dispensed in a 96-well plate at 50 μL/well each, and the plate was allowed to stand at room temperature for 1 hour. After removal of the solution, AppleBlock (Seikagaku Bio-Business, 200150) diluted 5-fold with PBS was dispensed at 200 μL/well each and the plate was allowed to stand at room temperature for 1 hour to block nonspecific binding. After washing three times with PBST (PBS containing 0.05% Tween 20), samples (e.g., mouse serum, hybridoma culture supernatant, recombinant antibody-expressed culture supernatant described later, or purified antibody) serially diluted with PBS were added at 50 μL/well each, and the plate was allowed to stand at room temperature for 1 hour. Thereafter, the plate was washed three times with PBST, and then peroxidase-labeled sheep anti-mouse IgG antibody (GE Healthcare, NA9310V) diluted with PBS was dispensed at 50 μL/well each, and the plate was allowed to stand at room temperature for 1 hour. After washing three times, a peroxidase-coloring kit (Sumitomo Bakelite, ML-11300) was added and allowed to color develop for a certain period of time, and the absorbance at 492 nm was measured with a plate reader.

Example 4: Antibody Epitope Analysis

Epitopes to which the antibodies bind were determined by the peptide scanning method. A total of 83 kinds of peptides were synthesized by fusing the N-terminal side of the amino acid sequences consisting of 11 consecutive residues shifted by 3 residues contained in Arg 172 to Ala 424 of the human RGMa protein (SEQ ID NO: 1 in Sequence Listing) with a spacer sequence (SGSG) with biotinylated N terminus (SEQ ID NO: 46 in Sequence Listing). After immobilizing the peptides on avidin-coated plates, the test antibodies (B5.116A3 and B5.70E4) were allowed to react. Subsequently, a peroxidase-labeled rabbit anti-mouse Ig antibody (Dako, P026002) was allowed to react. After a substrate solution was added and color developed for a certain time, the absorbance was measured with a plate reader.

As a result, B5.116A3 bound to peptides derived from human RGMa of Glu 298 to Gly 311 (two types of peptides: Glu 298 to Asp 308 and Val 301 to Gly 311), Asn 322 to Glu 335 (two types of peptides: Asn 322 to Thr 332 and Ile 325 to Glu 335), and Lys 367 to Ala 377; and B5.70E4 bound to peptides derived from human RGMa of Glu 298 to Gly 311 (two types of peptides: Glu 298 to Asp 308 and Val 301 to Gly 311), Asn 322 to Glu 335 (two types of peptides: Asn 322 to Thr 332 and Ile 325 to Glu 335), and Pro 349 to Thr 359.

Example 5: Sequence Analysis and Cloning of Mouse Antibody Gene

Total RNA was extracted from hybridoma cells producing a mouse monoclonal antibody (B5.116A3 or B5.70E4). Using the total RNA as a template, cDNA was synthesized by reverse transcription reaction. Using the cDNA as a template, genes of light chain variable and constant regions, and heavy chain variable and constant regions were amplified by PCR and the DNA sequences were determined. Next, based on the determined sequences of the variable and constant regions, full-length antibody genes were amplified by PCR and cloned. The amino acid sequences encoded by these antibody genes were as follows.

(1) B5.116A3 light chain amino acid sequence (SEQ ID NO: 4 in Sequence Listing)
DIQMTQTTSSLSASLGDRVTISCRASQDISSYLNWYQQKPDGTVKLLIYY

TSRLHSGVPSRFSGSGSGTDYSLTISNLEQEDIATYFCQQLNTLPWTFGG

GTKLEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC (2) B5.116A3 heavy chain amino acid sequence (SEQ ID NO: 5 in Sequence Listing)
EVKLEESGGGLVQPGGSMKLSCAASGFTFSDAWMDWVRQSPEKGLEWVAE

IRSKANNHATYYAESVKGRFTISRDDSKRSVYLQMNNLRAEDTGIYYCTR

RDGAYWGQGTLVTVSAAKTTPPSVYPLAPGCGDTTGSSVTLGCLVKGYFP

ESVTVTWNSGSLSSSVHTFPALLQSGLYTMSSSVTVPSSTWPSQTVTCSV

AHPASSTTVDKKLEPSGPISTINPCPPCKECHKCPAPNLEGGPSVFIFPP

NIKDVLMISLTPKVTCVVVDVSEDDPDVQISWFVNNVEVHTAQTQTHRED

YNSTIRVVSTLPIQHQDWMSGKEFKCKVNNKDLPSPIERTISKIKGLVRA

PQVYILPPPAEQLSRKDVSLTCLVVGFNPGDISVEWTSNGHTEENYKDTA

PVLDSDGSYFIYSKLNMKTSKWEKTDSFSCNVRHEGLKNYYLKKTISRSP

GK (3) B5.70E4 light chain amino acid sequence (SEQ ID NO: 6 in Sequence Listing)
DVVMTQTPLSLPVSLGDQASISCRSSQSLVHSNGNTYLHWYLQRPGQSPK

LLIYKVSNRFSGVPDRFSGSGSGTDFTLKISRVEAEDLGLYFCSQSTHVP

YTFGGGTKLEIKRADAAPTVSIFPPSSEQLTSGGASVVCFLNNFYPKDIN

VKWKIDGSERQNGVLNSWTDQDSKDSTYSMSSTLTLTKDEYERHNSYTCE

ATHKTSTSPIVKSFNRNEC (4) B5.70E4 heavy chain amino acid sequence (SEQ ID NO: 7 in Sequence Listing)
DVKLQESGPGLVKPSQSLSLTCSVTGYSITTSYYWNWIRQFPGNKLEWMG

YISYDGTNNYNPSLKNRISITRDTSKNQFFLRLNSVTTEDTATYYCAGSF

GYSQGTLVTVSAAKTTPPSVYPLAPGCGDTTGSSVTLGCLVKGYFPESVT

VTWNSGSLSSSVHTFPALLQSGLYTMSSSVTVPSSTWPSQTVTCSVAHPA

SSTTVDKKLEPSGPISTINPCPPCKECHKCPAPNLEGGPSVFIFPPNIKD

VLMISLTPKVTCVVVDVSEDDPDVQISWFVNNVEVHTAQTQTHREDYNST

IRVVSTLPIQHQDWMSGKEFKCKVNNKDLPSPIERTISKIKGLVRAPQVY

ILPPPAEQLSRKDVSLTCLVVGFNPGDISVEWTSNGHTEENYKDTAPVLD

SDGSYFIYSKLNMKTSKWEKTDSFSCNVRHEGLKNYYLKKTISRSPGK

Example 6: Preparation of Recombinant Mouse Antibody and Recombinant Rat Mouse Chimeric Antibody Recombinant mouse antibodies of two types of anti-RGMa antibodies B5.116A3 and B5.70E4 derived from hybridomas were prepared (hereinafter referred to as "r116A3" and "r70E4", respectively).

In addition, as a comparative example, recombinant rat mouse chimeric antibody (hereinafter referred to as "r5F9") was prepared by fusing the variable regions of rat antibody 5F9 with the constant regions of mouse antibody (IgG2bκ) (the light chain constant region is Arg 108 to Cys 214 of SEQ ID NO: 4 in Sequence Listing, and the heavy chain constant region is Ala 117 to Lys 452 of SEQ ID NO: 5 of the sequence listing) according to Patent Document 1 (WO2009/106356).

DNA encoding the light and heavy chains of each of the antibodies was inserted into pCDNA 3.3 (Life Technologies) to prepare an expression vector. The expression vector was introduced into HEK293F cells (Life Technologies) using Neofection 293 (ASTEC). The cells were cultured at 37° C. under 8% carbon dioxide gas atmosphere for 6 days, and then culture supernatant was recovered. For the purification of the recombinant antibody, the culture supernatant was applied to an affinity column on which Protein A or Protein G was immobilized (GE Healthcare), and antibodies bound to the column were eluted with 10 mM glycine hydrochloride (pH2.8). The eluate was neutralized immediately, and then replaced with PBS.

In the case where refined purity needs to be increased according to purpose of use, the antibodies purified with the Protein A column were purified with a Ceramic Hydroxyapatite Type 1 (CHT) column (BIORAD). Antibodies bound to the CHT column were washed with 10 mM $KH_2PO_4$ (pH6.5) and then eluted with 20 mM $KH_2PO_4$ (pH6.5), 0.5 M NaCl. Eluted fractions were collected and then replaced with PBS.

Example 7: Binding Assay on RGMa Protein Expressing Cells

A vector expressing full-length human RGMa protein (Met 1 to Cys 450 of SEQ ID NO: 1 in Sequence Listing), human RGMa protein C-terminal domain (Pro 169 to Cys 450 of SEQ ID NO: 1 in Sequence Listing), full-length mouse RGMa protein (Met 1 to Trp 454 of SEQ ID NO: 2 in Sequence Listing), or rat RGMa protein C-terminal domain (Pro 170 to Trp 449 of SEQ ID NO: 3 in Sequence Listing) was introduced into CHO or HEK 293 cells to prepare antigen-expressing cells.

In RGMa proteins, the C-terminal peptide is processed during GPI anchor addition reaction. Mouse and rat RGMa proteins are both cleaved at Ala 427 and the C-terminal peptide is removed. Therefore, the amino acid sequences of the full-length protein and the C-terminal domain expressed on a cell via a GPI anchor are the same in mouse and rat.

Test antibodies (r116A3 and r70E4) and r5F9 (Comparative Example) with a final concentration of 10 μg/mL were reacted with the above-described antigen-expressing cells and then the cells were washed with PBS containing 0.1% bovine serum albumin and 0.05% $NaN_3$. FITC-labeled anti-mouse immunoglobulin antibody (DAKO) was allowed to react and the cells were washed. Fluorescence was measured with flow cytometry (FACSCalibur manufactured by Beckton Dickinson), and the binding properties of the test antibodies to the antigen-expressing cells were evaluated (Table 1).

As a result, r116A3 and r70E4 were found to bind to the C-terminal domain of human and rat RGMa proteins, unlike r5F9. RGMa protein has neurite outgrowth inhibitory effect even in the C-terminal domain alone, and r116A3 and r70E4 inhibit both the full-length RGMa protein and the C-terminal domain.

TABLE 1

Evaluation of binding of various recombinant anti-RGMa antibodies to antigen-expressing cells*

| | Full-length human RGMa | Human RGMa C-terminal domain | Full-length mouse RGMa | Rat RGMa C-terminal domain |
|---|---|---|---|---|
| r116A3 | ++ | ++ | ++ | ++ |
| r70E4 | ++ | ++ | + | ++ |
| r5F9 | ++ | − | ++ | − |

*++ Strongly bind
+ Weakly bind
− Not bind

Example 8: Determination of Dissociation Constant for RGMa Protein

The affinity of the test antibodies (r116A3 and r70E4) and r5F9 (Comparative Example) for RGMa protein were measured by the surface plasmon resonance (SPR) method using Proteon XPR36 (Bio-Rad).

Human RGMa protein (R&D Systems, 2459-RM), the C-terminal domain of human RGMa protein (prepared in Example 1) or mouse RGMa protein (R&D Systems, 2458-RG) diluted to 10 µg/mL with 10 mM acetate buffer (pH4.5) was immobilized on a GLC sensor chip by amine coupling method. The serially diluted test antibodies were applied as analytes at a flow rate of 100 µL/min for 60 seconds to determine the dissociation constant (Kd value).

As shown in Table 2, r116A3 and r70E4 also bound to the C-terminal domain of human RGMa protein, but r5F9 did not. R116A3 bound to human RGMa protein 32 times stronger than r5F9 and to mouse RGMa protein 44 times stronger than r5F9.

TABLE 2

Affinity of anti-RGMa monoclonal antibody

| | Dissociation Constant (Kd value, nM) | | |
|---|---|---|---|
| Antibody | Human RGMa | Human RGMa C-terminal domain | Mouse RGMa |
| r116A3 | 0.0487 | 0.0568 | 0.201 |
| r70E4 | 2.43 | 1.12 | 174 |
| r5F9 (Comparative Example) | 1.59 | not bind | 8.98 |

Example 9: RGMa-Neogenin Binding Inhibition Assay

The extracellular domain (Ala 34 to Leu 1105) of the recombinant human neogenin protein (SEQ ID NO: 10 in Sequence Listing) was purified. A CHO cell line expressing human Neogenin protein extracellular domain was established. A histidine tag was fused to the C-terminus. From the culture supernatant of CHO cells, the extracellular domain was adsorbed on a nickel column (GE Healthcare, 17-5247-01), and then eluted with a 100 mM imidazole solution. By dialysis, the imidazole elution fraction was replaced with PBS.

Human RGMa protein (R&D systems, 2459-RM) was labeled with biotin using ChromaLink Biotin Labeling Kit (Solulink). Equal amounts of the biotin-labeled human RGMa protein adjusted to 2 µg/mL and the test antibodies (r116A3 and r70E4) subjected to 2-fold serial dilution were mixed and allowed to react at room temperature for 2 hours to prepare a mixed solution.

At the same time, 50 µL/well of the human neogenin protein extracellular domain adjusted to 2 µg/mL with PBS was added to a 96-well plate, and the plate was allowed to stand at room temperature for 1 hour to prepare a neogenin-immobilized plate. After removal of the solution, 2.5% bovine serum albumin solution was added and the plate was left to stand for 1 hour to block nonspecific binding. To the neogenin-immobilized plate, the above-described mixed solution was added at 50 µL/well, and the plate was allowed to stand at room temperature for 1 hour. Then, a washing operation was performed, and peridoxidase-labeled Avidin (VECTASTAIN ABC system, manufactured by Vector Laboratories) was added, and the plate was allowed to stand at room temperature for 1 hour. A washing operation was then performed, a substrate solution was added, color development was carried out for a certain period of time, and the absorbance was measured with a plate reader. The absorbance ratio in the absence of the antibody was plotted as 1, and the concentration-dependent RGMa-neogenin binding inhibition by the antibody was evaluated (FIG. 1).

As a result, unlike anti-human RGMa polyclonal antibody (R&D Systems, AF2459) and r5F9, r116A3 and r70E4 did not inhibit RGMa-neogenin binding.

Example 10: RGMa-BMP2 Binding Inhibition Assay

Human RGMa protein (R&D systems, 2459-RM) adjusted to 2 µg/mL with PBS was added to a 96-well plate at 50 µL/well each, and the plate was allowed to stand at room temperature for 1 hour. A 2.5% bovine serum albumin solution was added and the mixture was allowed to stand for 1 hour to block nonspecific binding, thereby preparing RGMa protein-immobilized plate. The test antibodies (B5.116A3 and B5.70E4) serially diluted to 0.01 to 10 µg/mL were added to the RGMa protein-immobilized plate and the plate was allowed to stand at room temperature for 1 hour. Then, a washing operation was performed, and human BMP2 protein (R&D systems, 355-BM) diluted to 0.5 µg/mL was added and the plate was left to stand at room temperature for 1 hour.

Figure 2:
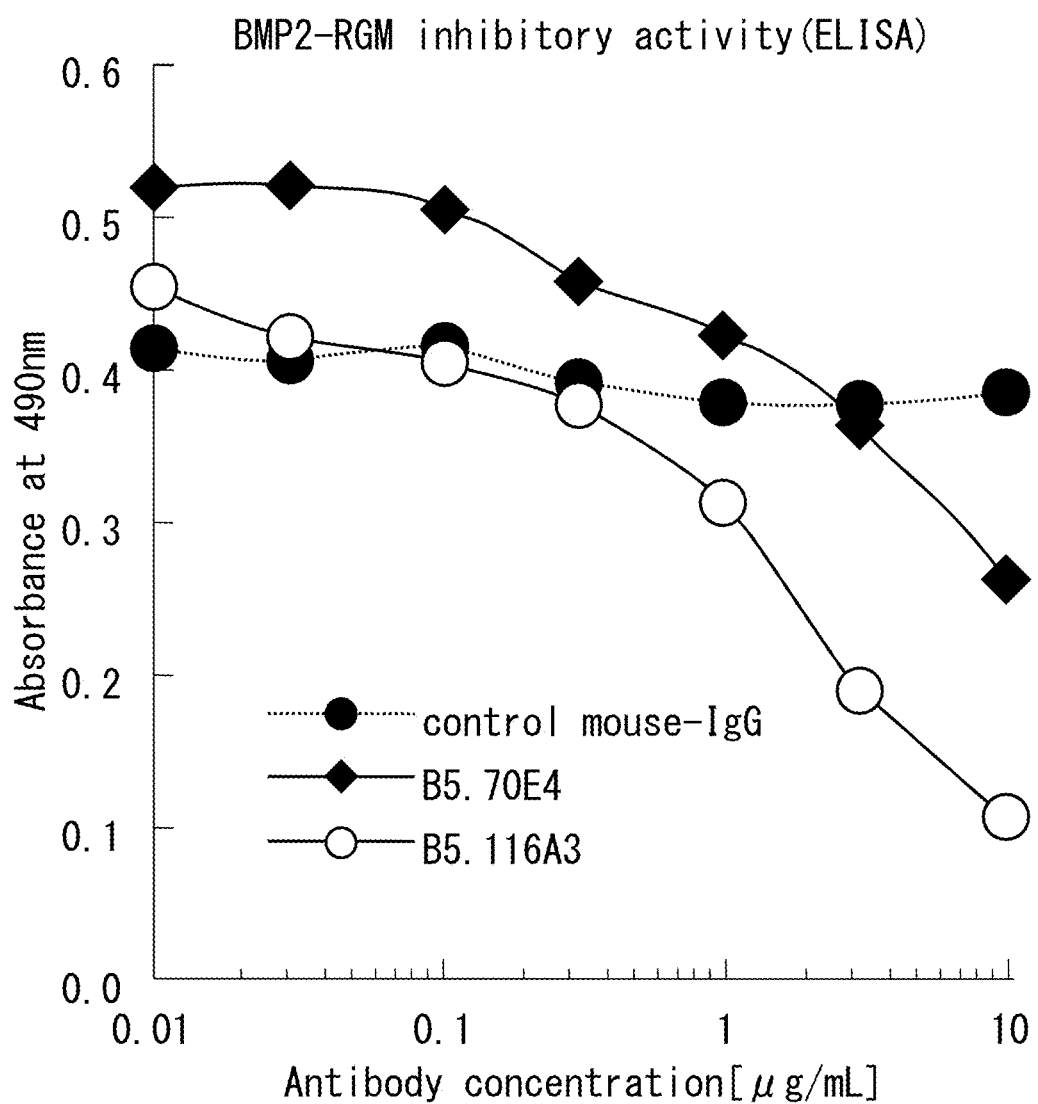
FIG. 2 shows a result of an RGMa-BMP2 binding inhibition assay using a control mouse-IgG and antibodies of the present invention (B5.70E4 and B5.116A3).

A biotin-labeled anti-BMP2 antibody was allowed to react, and further added with peroxidase-labeled Avidin (VECTASTAIN ABC system, manufactured by Vector Laboratories) and a substrate solution were added, color development was carried out for a certain period of time, and the absorbance was measured with a plate reader (FIG. 2).

As a result, in particular, the anti-RGMa antibody (B5.116A3) weakly inhibited the binding of RGMa-BMP2 in a concentration-dependent manner (Absorbance: 0.45 at 0.01 µg/mL, 0.4 at 0.1 µg/mL, 0.32 at 1 µg/mL, and 0.1 at 10 µg/mL).

Example 11: Design of Humanized Antibody

Humanization of the mouse monoclonal antibody B5.116A3 was carried out by complementarity determining region (CDR) grafting according to the method by Winter et al. described in U.S. Pat. No. 2,912,618.

First, 3D homology models of the light and heavy chain variable regions of the mouse monoclonal antibody B5.116A3 were prepared and amino acid residues within the framework (FW) region, located near CDR were identified. FWs of human antibodies in which these amino acids are maintained as many as possible were selected, CDRs of the mouse antibody were grafted thereto, and thus designing a humanized antibody. In the designed humanized antibody sequence, the heavy chain is described as HA (SEQ ID NO: 11 in Sequence Listing) and the light chain is described as KA (SEQ ID NO: 19 in Sequence Listing). In addition, a plurality of humanized antibody sequences were designed by introducing additional mutations into amino acids within FWs involved in structural stability of the variable region (A total of 8 heavy chains ranging from HB to HH including HA and a total of 7 light chains ranging from KB to KG including KA).

TABLE 3

Designed humanized antibody sequences

| | | SEQ ID NO in the sequence listing |
|---|---|---|
| Heavy Chain | | |
| HA | Sequence in which CDRs of mouse antibody B5.116A3 are grafted to FWs of human antibody | 11 |
| HB | HA sequence with substitution of Ala 81 by Val and Lys 89 by Arg | 12 |
| HC | HA sequence with substitution of Ala 81 by Val | 13 |
| HD | HA sequence with substitution of Lys 89 by Arg | 14 |
| HE | HA sequence with substitution of Ala 81 by Val, Lys 89 by Arg, and Phe 37 by Val | 15 |
| HF | HA sequence with substitution of Leu 95 by Val | 16 |
| HG | HA sequence with substitution of Phe 37 by Val | 17 |
| HH | HA sequence with substitution of Phe 37 by Val, and Leu 95 by Val | 18 |
| Light Chain | | |
| KA | Sequence in which CDRs of mouse antibody B5.116A3 are grafted to FWs of human antibody | 19 |
| KB | KA sequence with substitution of Phe 71 by Tyr | 20 |
| KC | KA sequence with substitution of Phe 71 by Tyr, and Phe 44 by Val | 21 |
| KD | KA sequence with substitution of Ser 85 by Thr | 22 |
| KE | KA sequence with substitution of Pro 44 by Val | 23 |
| KF | KA sequence with substitution of Pro 44 by Val, and Ser 85 by Thr | 24 |
| KG | KA sequence with substitution of Phe 71 by Tyr, Pro 44 by Val, and Ser 85 by Thr | 25 |

Example 12: Preparation of Recombinant Mouse Human Chimeric Antibody and Recombinant Humanized Antibody (1) Recombinant mouse human chimeric anti-RGMa antibody 116A3 (r116A3C) having the following amino acid sequences was prepared according to Example 6.

```
Light chain (SEQ ID NO: 8 in Sequence Listing)
DIQMTQTTSSLSASLGDRVTISCRASQDISSYLNWYQQKPDGTVKLLIYY

TSRLHSGVPSRFSGSGSGTDYSLTISNLEQEDIATYFCQQLNTLPWTFGG

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Heavy chain (SEQ ID NO: 9 in Sequence Listing)
EVKLEESGGGLVQPGGSMKLSCAASGFTFSDAWMDWVRQSPEKGLEWVAE

IRSKANNHATYYAESVKGRFTISRDDSKRSVYLQMNNLRAEDTGIYYCTR

RDGAYWGQGTLVTVSAASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK
```

(2) A total of 20 humanized anti-RGMa antibodies comprising the following combinations of heavy and light chains were prepared according to Example 6.

Heavy chain/light chain combinations;
HA/KA, HA/KB, HA/KC, HA/KG, HB/KC, HC/KA, HC/KB, HD/KA, HD/KB, HD/KC, HD/KD, HE/KA, HF/KA, HF/KF, HF/KG, HG/KD, HG/KH, HH/KA, HH/KD, HH/KF (3) A recombinant humanized anti-RGMa antibody (hereinafter referred to as rH5F9) was prepared according to Example 6 (Comparative Example).

The variable region of the humanized anti-RGMa monoclonal antibody h5F9 described in Patent Document 1 (WO2009/106356) (the light chain is seq ID_53 of Patent Document 1, and the heavy chain is seq ID_50 of Patent Document 1) was ligated with the human antibody constant region (the light chain is Arg 108 to Cys 214 of SEQ ID NO: 26 in Sequence Listing, and heavy chain is Ala 117 to Lys 446 of SEQ ID NO: 27 in Sequence Listing).

Example 13: Thermal Stability Test for Antibody

Figure 3:
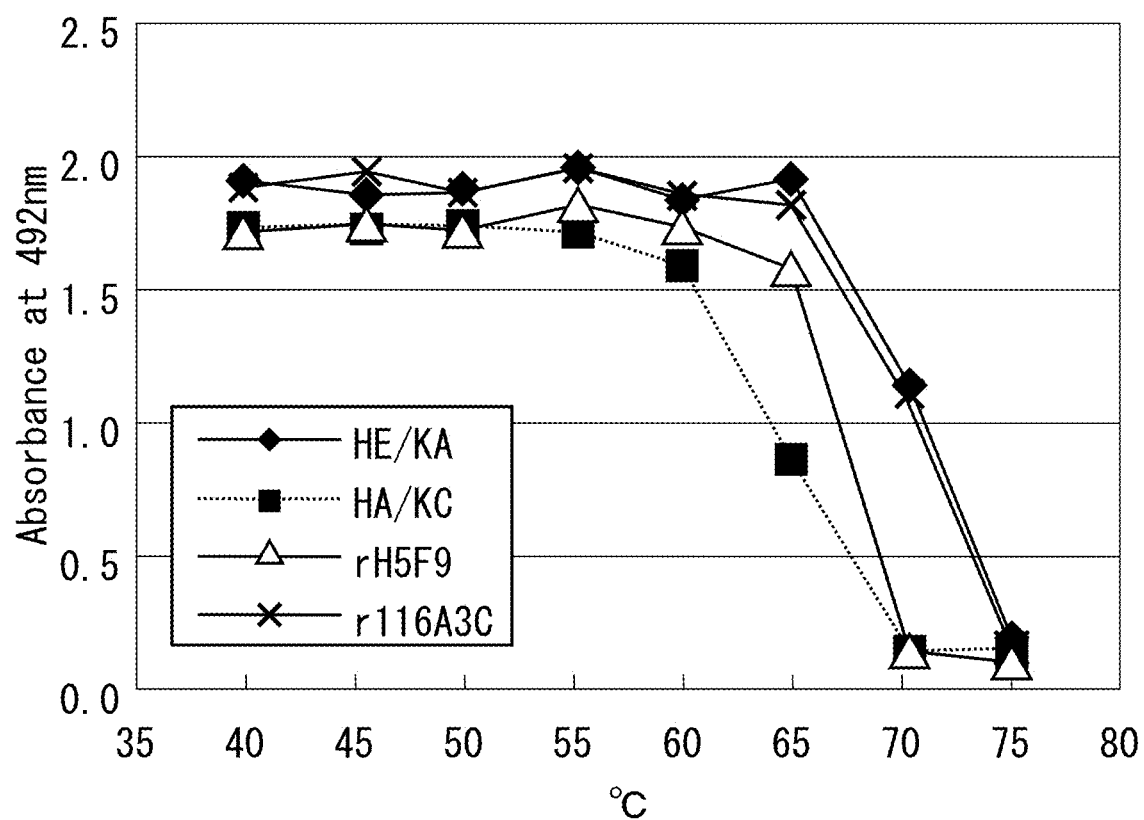
FIG. 3 shows a result of a thermal stability test for antibodies using an antibody of comparative example (rH5F9), a chimeric antibody of the present invention (r116A3C) and humanized antibodies of the present invention (HE/KA and HA/KC).

Twenty μL aliquots of the culture supernatant in which the recombinant antibody described in Example 12 was expressed were collected and heat-treated for 10 minutes at 8 temperature points of 40, 45, 50, 55, 60, 65, 70 and 75° C., respectively, using a thermal cycler (Takara bio, TP 600). The culture supernatant was diluted with PBS so that the final concentration of the antibody was 125 ng/mL. Thereafter, the culture supernatant was subjected to ELISA on which human RGMa proteins are immobilized described in Example 3 to evaluate the antigen binding property of the antibody (FIG. 3).

As a result, a humanized antibody comprising a combination of heavy chain HE and light chain KA (hereinafter referred to as "rH116A3"), and a mouse human chimeric antibody (r116A3C) showed better thermal stability than the humanized antibody (rH5F9). Hereinafter, the humanized antibody comprising this combination of HE/KA is described as rH116A3.

When the heat treatment was not performed, the mouse human chimeric antibody (r116A3C) and the humanized antibody (rH116A3) showed equivalent antigen binding properties, and there was no decrease in antigen binding property associated with humanization.

Example 14: Establishment of a CHO Stable Cell Line Producing Humanized Anti-RGMa Antibody (rH116A3)

A CHO stable cell line producing humanized anti-RGMa antibody (rH116A3) was established using Lonza GS Xceed system (Lonza). A pXC double gene vector comprising the light chain coding sequence (SEQ ID NO: 44 in Sequence Listing) and the heavy chain coding sequence (SEQ ID NO:

43 in Sequence Listing) of the humanized anti-RGMa antibody (rH116A3) was introduced into a CHOK1SV GS knock out parent cell line, and a pool of transformed cells was obtained under methionine sulphoximine (MSX) selection. After separating into single cells by flow cytometry, antibody production amount in culture supernatant, cell proliferation and the like were evaluated, and a CHO stable cell line was obtained.

Example 15: Neurite Outgrowth Assay

A cerebellum was excised from a neonatal rat (P7), suspended in a trypsin solution (0.25% trypsin solution in PBS containing 0.2% DNase) and digested at 37° C. for 10 to 15 minutes. Next, DMEM medium containing 10% fetal bovine serum was added and the mixture was centrifuged. The cells were resuspended in the same medium and centrifuged, and the same procedure was repeated twice to wash the cells. Further, this cell suspension was filtered through a 70 μm cell strainer and centrifuged, and the precipitated fraction was resuspended in the same medium. B27 supplement (GIBCO) was added to the cell suspension to prepare neonatal rat cerebellar granule cells.

Figure 4:
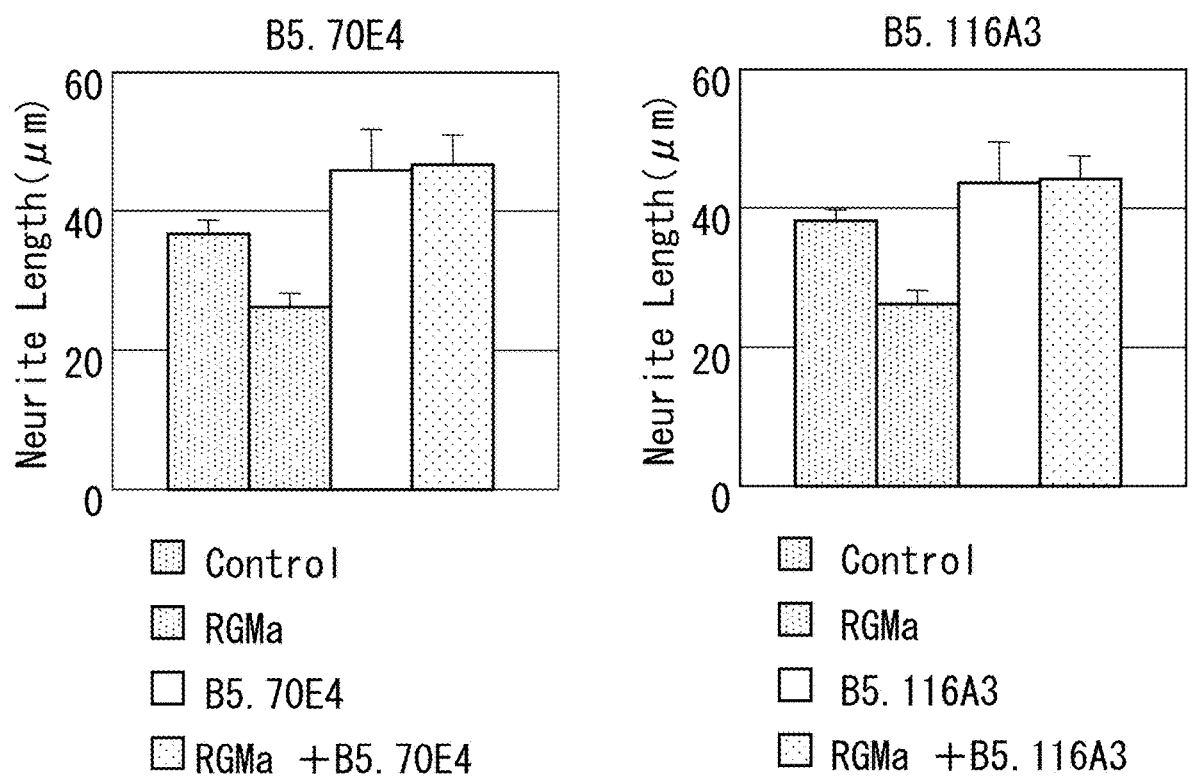
FIG. 4 shows a result of a neurite outgrowth assay using the antibodies of the present invention (B5.70E4 (left) and B5.116A3 (right)).

Next, the neonatal rat cerebellar granule cells were seeded on a cell culture plate and cultured at 37° C. for 1 day. Recombinant RGMa protein (R&D systems, 2459-RM) with a final concentration of 2 μg/mL was added and the cells were cultured at 37° C. for 2 days. The neurite length was measured by microscopy. As shown in FIG. 4, the addition of RGMa resulted in neurite length changes from 37 μm to 26 μm in the experiment on the left figure and from 38 μm to 27 μm in the right figure, thus inhibiting neurite outgrowth. Although addition of only the test antibody (B5.116A3 or B5.70E4) at a final concentration of 10 μg/mL did not change the neurite length, simultaneous addition of recombinant RGMa protein and the test antibody induced neurite outgrowth to the same extent as a control (no RGMa added), which indicate neutralizing effect of the antibody against RGMa protein.

Example 16: Efficacy Test Using a Rat Spinal Cord Injury Model

A Wistar rat (female, 8 weeks old, weighing about 200 g) anesthetized by aspiration of halothane (Takeda Pharmaceutical) was subjected to a laminectomy of the anterior and posterior vertebrae around the spinal level T9 (T8 to T10), and the spinal cord was exposed. In the case of evaluation using spinal cord crush model, pressure of 200 kdyn was applied to the exposed spinal cord using IH impactor (Precision System).

Immediately after damaging the spinal cord as described above, an osmotic minipump filled with 400 μg/mL of the test antibody (r116A3 or r70E4) or a control mouse antibody (mo-IgG2bκ) (200 μL volume, 0.5 μL/hour, 14 Day delivery) (Alzet, model 2002) was placed under the skin of the back of the rat. The tip of a silicon tube connected to the outlet of the osmotic mini pump was placed under the dura at the site of spinal cord injury. The tube was sewn and fixed to the spinous processes on the right lower limb side of the laminectomized site, the muscle and skin layers were sutured, and the rat was raised.

Figure 5:
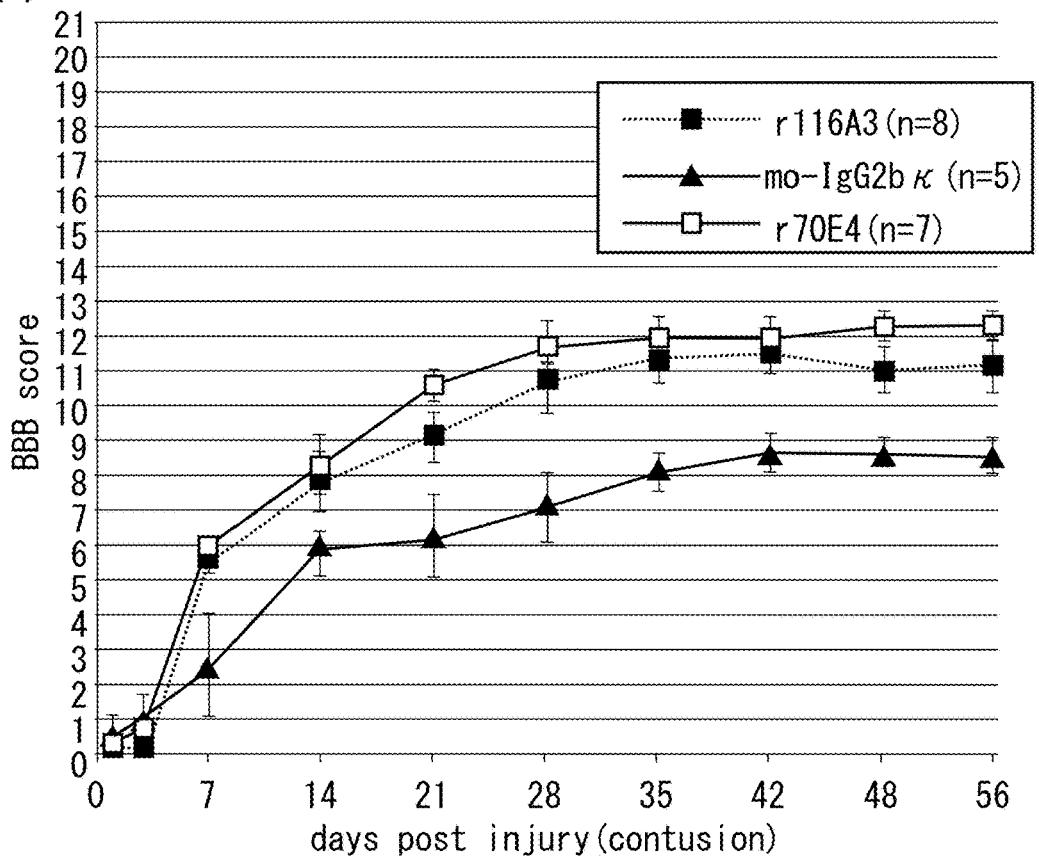
FIG. 5 shows a result of an efficacy test using a control mouse-IgG (mo-IgG2bk), and the antibodies of the present invention (r70E4 and r116A3) and using a rat model of spinal cord injury. Results of efficacy tests in (A) a spinal cord crush model and (B) a spinal cord hemisection model are shown.
Figure 5:
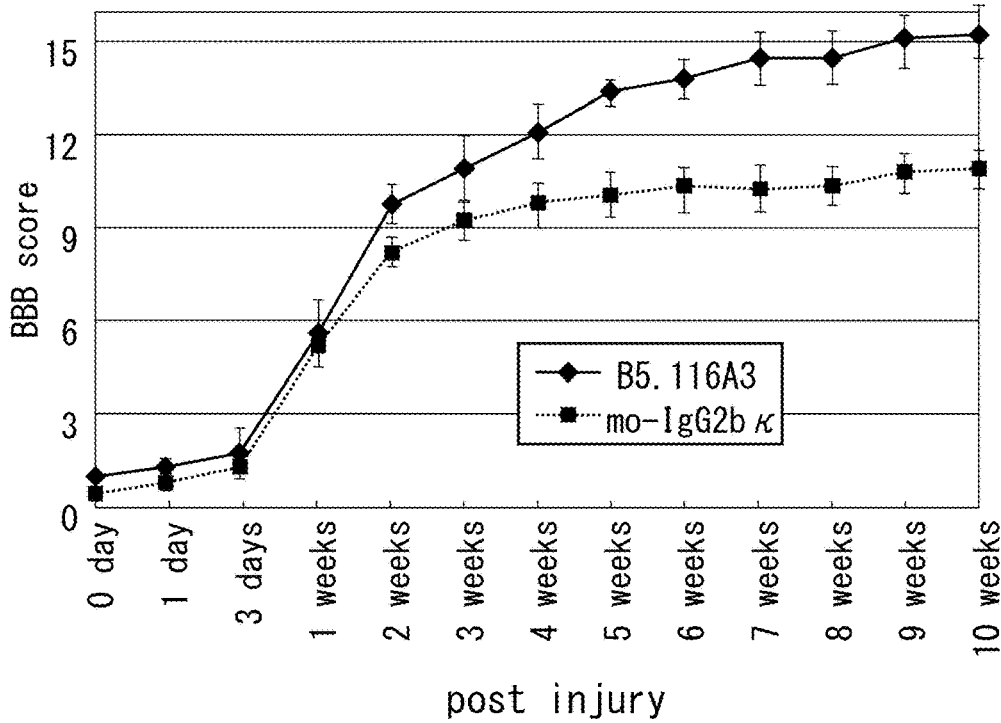

The motor function of spinal cord injury model rat was evaluated using Basso-Beattie-Bresnahan (BBB) score (Basso, D. M., Beattie, M. S., & Bresnahan, J. C., A sensitive and reliable locomotor rating scale for open field testing in rats. J Neurotrauma 12, 1-21 (1995)) at 0, 1, 3 and 7 days after injury, and every week thereafter for up to 8 weeks. As a result, as shown in FIG. 5(A), r116A3 or r70E4 significantly improved the BBB score 4 or 3 weeks after administration, respectively, compared to the control antibody (mo-IgG2bκ) ($p<0.05$, Student's t-test).

In the case of evaluation using a spinal cord hemisection model, the dorsal side of the exposed spinal cord was cut to a depth of 1.8 mm to 2.0 mm. In the same manner as above, the test antibody (B5.116A3) or the control mouse antibody (mo-IgG2bκ) was administered using osmotic minipump and evaluated using BBB score at 0, 1, 3 and 7 days after injury, and every week thereafter for up to 10 weeks. As shown in FIG. 5(B), B5.116A3 significantly improved the BBB score 4 weeks after administration compared to the control antibody (mo-IgG2bκ) ($p<0.01$, Student's t-test).

Example 17: Efficacy Test Using Mouse Model with Multiple Sclerosis $PLP_{139-151}$ peptide (HSLGKWLGHPDKF: SEQ ID NO: 45 in Sequence Listing, Peptide Institute) was dissolved in physiological saline (Otsuka Pharmaceutical Factory) and mixed with incomplete Freund's adjuvant (Sigma) to which dead tubercle *bacillus* H37 Ra (Difco Laboratories) was added to prepare an emulsion. SJL/JorllcoCrj (SJL/J) mouse (Charles River Japan) was immunized subcutaneously in the back with the $PLP_{139-151}$ peptide at 50 μg/head, and EAE score and body weight change were evaluated (H. Kataoka, K Sugahara, K. Shimano, K. Teshima, M. Koyama, A. Fukunari and K. Chiba. FTY720, sphingosine 1-phosphate receptor modulator, ameliorates experimental autoimmune encephalomyelitis by inhibition of T cell infiltration. Cellular & Molecular Immunology 6, 439-448, 2005.) (FIG. 6).

Test antibody (B5.116A3) diluted in physiological saline was intraperitoneally administered at 20 mg/kg each at 7 and 10 days or 18 and 21 days after the immunization with $PLP_{139-151}$ peptide.

Figure 6:
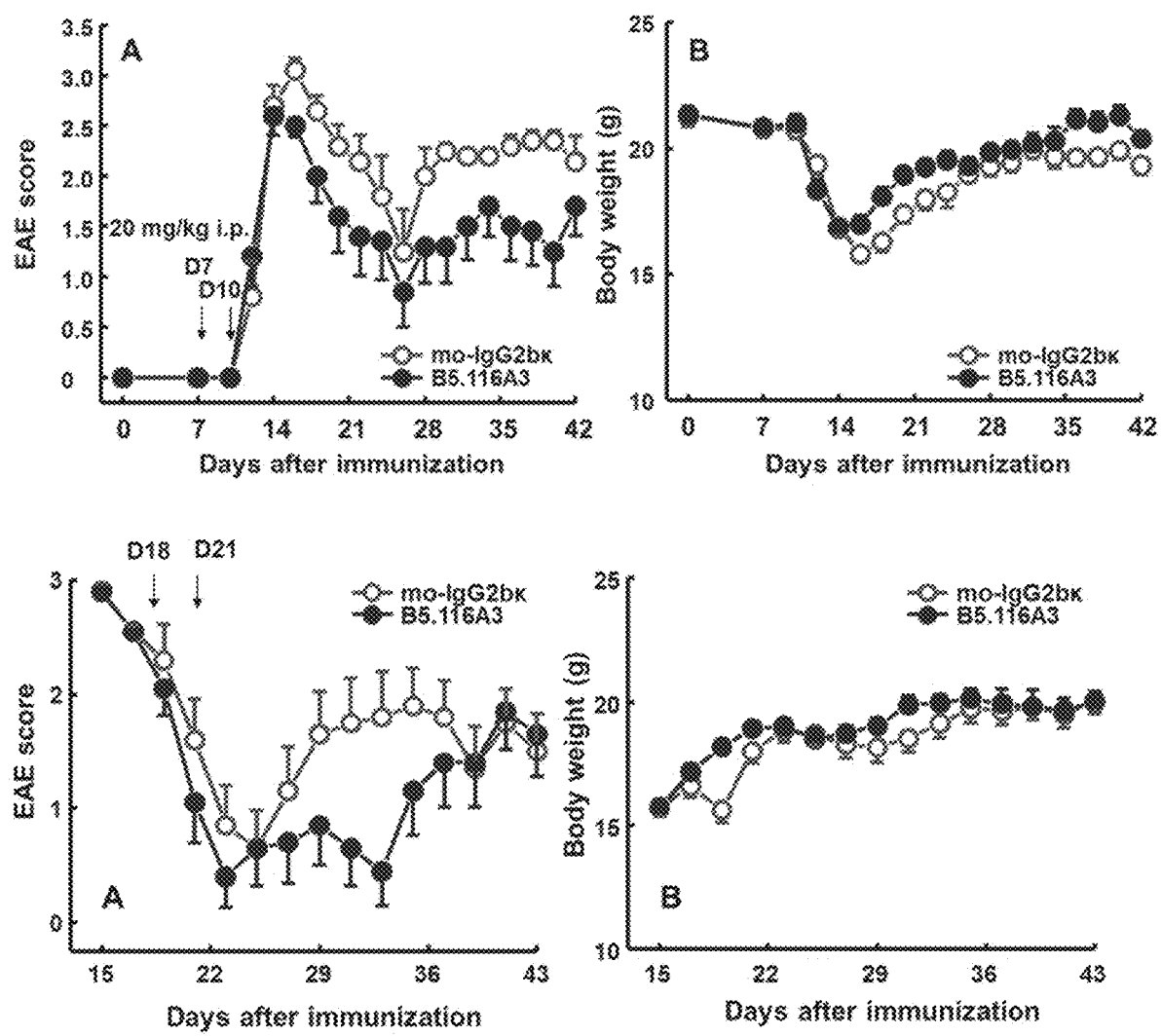
FIG. 6 shows a result of an efficacy test for the antibody of the present invention (B5.116A3) using a mouse model of multiple sclerosis induced by a $PLP_{139-151}$ peptide. The left side shows EAE scores, the right side shows changes in body weight, and the top and bottom parts show results when the test antibodies were administered after 7 and 10 days and after 18 and 21 days, respectively.

As a result, as shown in FIG. 6, compared with the control antibody (mo-IgG2bκ), the anti-RGMa mouse monoclonal antibody (B5.116A3) inhibited the deterioration of EAE score by administration before onset (upper part of FIG. 6) and showed relapse prevention effect by administration after onset (lower part of FIG. 6).

Example 18: Immunogenicity Test of Antibody

Undifferentiated dendritic cells contained in peripheral blood derived from 51 healthy donors were matured by granulocyte-monocyte colony-stimulating factor (GM-CSF) and Interleukin-4 stimulations. The test antibody (rH116A3) at a final concentration of 50 μg/mL was added to the mature dendritic cells and the cells were cultured for 4, 5 days to allow the antibody to be taken up into the dendritic cells. Peripheral blood CD4+ T cells (helper T cells) derived from the same donor were mixed with the dendritic cells, and co-cultured for another week, and then the proliferation of T cells was measured by flow cytometry. Using the T cell proliferation activity of the test antibody as an index, the immunogenicity risk in human was evaluated. As a result, T cell proliferation was observed in 4 (7.8%) out of 51 donors, and thus the immunogenicity risk was low.

The invention claimed is:

1. An isolated anti-repulsive guidance molecule a (anti-RGMa) antibody, or an antigen-binding fragment thereof,
   wherein the amino acid sequence of each of the light chain complementarity determining region 1 (LCDR1), the light chain complementarity determining region 2 (LCDR2), the light chain complementarity determining region 3 (LCDR3), the heavy chain complementarity determining region 1 (HCDR1), the heavy chain complementarity determining region 2 (HCDR2) and the heavy chain complementarity determining region 3 (HCDR3) comprises either
(A) LCDR1: RASQDISSYLN (SEQ ID NO: 30),
   LCDR2: YTSRLHS (SEQ ID NO: 31),
   LCDR3: QQLNTLP (SEQ ID NO: 32),
   HCDR1: DAWMD (SEQ ID NO: 33),
   HCDR2: EIRSKANNHATYYAESVKG (SEQ ID NO: 34), and
   HCDR3: RDGAY (SEQ ID NO: 35),
   or
(B) LCDR1: RSSQSLVHSNGNTYLH (SEQ ID NO: 36)
   LCDR2: KVSNRFS (SEQ ID NO: 37)
   LCDR3: SQSTHVP (SEQ ID NO: 38)
   HCDR1: TSYYWN (SEQ ID NO: 39)
   HCDR2: YISYDGTNNYNPSLKN (SEQ ID NO: 40), and
   HCDR3: SFG, and
   wherein, in either (A) or (B), one amino acid may be substituted, deleted, or added in one or more of the CDR sequences.

2. The anti-RGMa antibody or antigen-binding fragment thereof according to claim 1, wherein, in either (A) or (B), one amino acid is substituted.

3. The anti-RGMa antibody or antigen-binding fragment thereof according to claim 2, wherein the amino acid substitution is conservative substitution.

4. The anti-RGMa antibody or an antigen-binding fragment thereof according to claim 3,
   wherein the anti-RGMa antibody or an antigen-binding fragment thereof binds to RGMa, and
   wherein the anti-RGMa antibody or antigen binding fragment thereof neutralizes the neurite outgrowth inhibitory activity of RGMa.

5. The anti-RGMa antibody or antigen binding fragment thereof according to claim 1,
   wherein the heavy chain variable region (VH) comprises the following:
   VH:
   HA (SEQ ID NO: 11), HB (SEQ ID NO: 12), HC (SEQ ID NO: 13), HD (SEQ ID NO: 14), HE (SEQ ID NO: 15), HF (SEQ ID NO: 16), HG (SEQ ID NO: 17), or HH (SEQ ID NO: 18); and
   wherein the light chain variable region (VL) comprises the following:
   VL:
   KA (SEQ ID NO: 19), KB (SEQ ID NO: 20), KC (SEQ ID NO: 21), KD (SEQ ID NO: 22), KE (SEQ ID NO: 23), KF (SEQ ID NO: 24), or KG (SEQ ID NO: 25).

6. The anti-RGMa antibody or antigen binding fragment thereof according to claim 5, wherein the heavy chain variable region (VH) and the light chain variable region (VL) combinations are selected from the following:
   HA/KA, HA/KB, HA/KC, HA/KG, HB/KC, HC/KA, HC/KB, HD/KA, HD/KB, HD/KC, HD/KD, HE/KA, HF/KA, HF/KF, HF/KG, HG/KD, HG/KH, HH/KA, HH/KD, and HH/KF.

7. The anti-RGMa antibody or antigen-binding fragment thereof according to claim 1, wherein the anti-RGMa antibody is a humanized antibody.

8. The anti-RGMa antibody or antigen-binding fragment thereof according to claim 1, wherein the anti-RGMa antibody comprises constant regions of human IgG.

9. A pharmaceutical composition comprising the anti-RGMa antibody or antigen-binding fragment thereof according to claim 1.

10. A nucleic acid molecule coding for the anti-RGMa antibody or antigen-binding fragment thereof according to claim 1.

11. A recombinant vector comprising the nucleic acid molecule according to claim 10.

12. A host cell containing the recombinant vector according to claim 11.

13. A method for producing the anti-RGMa antibody or antigen-binding fragment thereof according to claim 1, the method comprising a step of culturing a host cell,
   wherein the host cell contains a recombinant vector, and
   wherein the recombinant vector comprises a nucleic acid molecule coding for the anti-RGMa antibody or antigen-binding fragment thereof according to claim 1.

14. A method of treating or reducing relapse of a neurological or immunological disease in a subject, wherein the neurological or immunological disease is selected from the group consisting of spinal cord injury, neurotrauma, and multiple sclerosis.

15. The method according to claim 14, wherein the neurological or immunological disease is spinal cord injury.

16. The method according to claim 14, wherein the neurological or immunological disease is neurotrauma.

17. The method according to claim 14, wherein the neurological or immunological disease is multiple sclerosis.

* * * * *

SEQUENCE LISTING

<160> NUMBER OF SEQ ID NOS: 46

<210> SEQ ID NO 1
<211> LENGTH: 450
<212> TYPE: PRT
<213> ORGANISM: Homo sapiens

<400> SEQUENCE: 1

```
Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Phe Trp Pro
            20                  25                  30

Thr Leu Ala Phe Leu Leu Cys Ser Phe Pro Ala Ala Thr Ser Pro Cys
        35                  40                  45

Lys Ile Leu Lys Cys Asn Ser Glu Phe Trp Ser Ala Thr Ser Gly Ser
    50                  55                  60

His Ala Pro Ala Ser Asp Asp Thr Pro Glu Phe Cys Ala Ala Leu Arg
65                  70                  75                  80

Ser Tyr Ala Leu Cys Thr Arg Arg Thr Ala Arg Thr Cys Arg Gly Asp
                85                  90                  95

Leu Ala Tyr His Ser Ala Val His Gly Ile Glu Asp Leu Met Ser Gln
            100                 105                 110

His Asn Cys Ser Lys Asp Gly Pro Thr Ser Gln Pro Arg Leu Arg Thr
        115                 120                 125

Leu Pro Pro Ala Gly Asp Ser Gln Glu Arg Ser Asp Ser Pro Glu Ile
    130                 135                 140

Cys His Tyr Glu Lys Ser Phe His Lys His Ser Ala Thr Pro Asn Tyr
145                 150                 155                 160

Thr His Cys Gly Leu Phe Gly Asp Pro His Leu Arg Thr Phe Thr Asp
                165                 170                 175

Arg Phe Gln Thr Cys Lys Val Gln Gly Ala Trp Pro Leu Ile Asp Asn
            180                 185                 190

Asn Tyr Leu Asn Val Gln Val Thr Asn Thr Pro Val Leu Pro Gly Ser
        195                 200                 205

Ala Ala Thr Ala Thr Ser Lys Leu Thr Ile Ile Phe Lys Asn Phe Gln
    210                 215                 220

Glu Cys Val Asp Gln Lys Val Tyr Gln Ala Glu Met Asp Glu Leu Pro
225                 230                 235                 240

Ala Ala Phe Val Asp Gly Ser Lys Asn Gly Gly Asp Lys His Gly Ala
                245                 250                 255

Asn Ser Leu Lys Ile Thr Glu Lys Val Ser Gly Gln His Val Glu Ile
            260                 265                 270

Gln Ala Lys Tyr Ile Gly Thr Thr Ile Val Val Arg Gln Val Gly Arg
        275                 280                 285

Tyr Leu Thr Phe Ala Val Arg Met Pro Glu Glu Val Val Asn Ala Val
    290                 295                 300

Glu Asp Trp Asp Ser Gln Gly Leu Tyr Leu Cys Leu Arg Gly Cys Pro
305                 310                 315                 320

Leu Asn Gln Gln Ile Asp Phe Gln Ala Phe His Thr Asn Ala Glu Gly
                325                 330                 335

Thr Gly Ala Arg Arg Leu Ala Ala Ala Ser Pro Ala Pro Thr Ala Pro
            340                 345                 350

Glu Thr Phe Pro Tyr Glu Thr Ala Val Ala Lys Cys Lys Glu Lys Leu
        355                 360                 365
```

```
Pro Val Glu Asp Leu Tyr Tyr Gln Ala Cys Val Phe Asp Leu Leu Thr
    370                 375                 380
Thr Gly Asp Val Asn Phe Thr Leu Ala Ala Tyr Tyr Ala Leu Glu Asp
385                 390                 395                 400
Val Lys Met Leu His Ser Asn Lys Asp Lys Leu His Leu Tyr Asp Arg
                405                 410                 415
Thr Arg Asp Leu Pro Gly Arg Ala Ala Ala Gly Leu Pro Leu Ala Pro
            420                 425                 430
Arg Pro Leu Leu Gly Ala Leu Val Pro Leu Leu Ala Leu Leu Pro Val
        435                 440                 445
Phe Cys
    450

<210> SEQ ID NO 2
<211> LENGTH: 454
<212> TYPE: PRT
<213> ORGANISM: Mus musculus

<400> SEQUENCE: 2

Met Gln Pro Pro Arg Glu Arg Leu Val Val Thr Gly Arg Ala Gly Trp
1               5                   10                  15
Met Gly Met Gly Arg Gly Ala Gly Arg Ser Ala Leu Gly Leu Trp Pro
            20                  25                  30
Thr Leu Ala Phe Leu Leu Cys Ser Phe Pro Ala Ala Ile Ser Pro Cys
        35                  40                  45
Lys Ile Leu Lys Cys Asn Ser Glu Phe Trp Ser Ala Thr Ser Ser Gly
    50                  55                  60
Ser His Ala Pro Ala Ser Asp Asp Val Pro Glu Phe Cys Ala Ala Leu
65                  70                  75                  80
Arg Thr Tyr Ala Leu Cys Thr Arg Arg Thr Ala Arg Thr Cys Arg Gly
                85                  90                  95
Asp Leu Ala Tyr His Ser Ala Val His Gly Ile Glu Asp Leu Met Ser
            100                 105                 110
Gln His Asn Cys Ser Lys Asp Gly Pro Thr Ser Gln Pro Arg Val Arg
        115                 120                 125
Thr Leu Pro Pro Ala Gly Asp Ser Gln Glu Arg Ser Asp Ser Pro Glu
    130                 135                 140
Ile Cys His Tyr Glu Lys Ser Phe His Lys His Ser Ala Ala Pro Asn
145                 150                 155                 160
Tyr Thr His Cys Gly Leu Phe Gly Asp Pro His Leu Arg Thr Phe Thr
                165                 170                 175
Asp His Phe Gln Thr Cys Lys Val Gln Gly Ala Trp Pro Leu Ile Asp
            180                 185                 190
Asn Asn Tyr Leu Asn Val Gln Val Thr Asn Thr Pro Val Leu Pro Gly
        195                 200                 205
Ser Ala Ala Thr Ala Thr Ser Lys Leu Thr Ile Ile Phe Lys Asn Phe
    210                 215                 220
Gln Glu Cys Val Asp Gln Lys Val Tyr Gln Ala Glu Met Asp Glu Leu
225                 230                 235                 240
Pro Ser Ala Phe Ala Asp Gly Ser Lys Asn Gly Gly Asp Lys His Gly
                245                 250                 255
Ala Asn Ser Leu Lys Ile Thr Glu Lys Val Ser Gly Gln His Val Glu
            260                 265                 270
Ile Gln Ala Lys Tyr Ile Gly Thr Thr Ile Val Val Arg Gln Val Gly
        275                 280                 285
```

```
Arg Tyr Leu Thr Phe Ala Val Arg Met Pro Glu Glu Val Val Asn Ala
        290                 295                 300

Val Glu Asp Arg Asp Ser Gln Gly Leu Tyr Leu Cys Leu Arg Gly Cys
305                 310                 315                 320

Pro Leu Asn Gln Gln Ile Asp Phe Gln Ala Phe Arg Ala Asn Ala Glu
                325                 330                 335

Ser Pro Arg Arg Pro Ala Ala Ala Ser Pro Ser Pro Val Val Pro Glu
                340                 345                 350

Thr Phe Pro Tyr Glu Thr Ala Val Ala Lys Cys Lys Glu Lys Leu Pro
        355                 360                 365

Val Glu Asp Leu Tyr Tyr Gln Ala Cys Val Phe Asp Leu Leu Thr Thr
    370                 375                 380

Gly Asp Val Asn Phe Thr Leu Ala Ala Tyr Tyr Ala Leu Glu Asp Gly
385                 390                 395                 400

Lys Met Leu His Ser Asn Lys Asp Lys Leu His Leu Phe Glu Arg Thr
                405                 410                 415

Arg Glu Leu Pro Gly Ala Val Ala Ala Ala Ala Ala Ala Ala Thr Thr
                420                 425                 430

Phe Pro Leu Ala Pro Gln Ile Leu Leu Gly Thr Ile Pro Leu Leu Val
        435                 440                 445

Leu Leu Pro Val Leu Trp
    450

<210> SEQ ID NO 3
<211> LENGTH: 449
<212> TYPE: PRT
<213> ORGANISM: Rattus norvegicus

<400> SEQUENCE: 3

Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Leu Trp Pro
                20                  25                  30

Thr Leu Ala Phe Leu Leu Cys Ser Phe Pro Ala Ala Ile Ser Pro Cys
        35                  40                  45

Lys Ile Leu Lys Cys Asn Ser Glu Phe Trp Ser Ala Thr Ser Ser Gly
50                  55                  60

Ser His Ala Pro Ala Ser Asp Asp Val Pro Glu Phe Cys Ala Ala Leu
65                  70                  75                  80

Arg Thr Tyr Ala Leu Cys Thr Arg Arg Thr Ala Arg Thr Cys Arg Gly
                85                  90                  95

Asp Leu Ala Tyr His Ser Ala Val His Gly Ile Glu Asp Leu Met Ser
                100                 105                 110

Gln His Asn Cys Ser Lys Asp Gly Pro Thr Ser Gln Pro Arg Val Arg
        115                 120                 125

Thr Leu Pro Pro Ala Gly Asp Ser Gln Glu Arg Ser Asp Ser Pro Glu
    130                 135                 140

Ile Cys His Tyr Glu Lys Ser Phe His Lys His Ser Ala Ala Pro Asn
145                 150                 155                 160

Tyr Thr His Cys Gly Leu Phe Gly Asp Pro His Leu Arg Thr Phe Thr
                165                 170                 175

Asp His Phe Gln Thr Cys Lys Val Gln Gly Ala Trp Pro Leu Ile Asp
                180                 185                 190

Asn Asn Tyr Leu Asn Val Gln Val Thr Asn Thr Pro Val Leu Pro Gly
```

```
                195                 200                 205
Ser Ala Ala Thr Ala Thr Ser Lys Leu Thr Ile Ile Phe Lys Asn Phe
210                 215                 220

Gln Glu Cys Val Asp Gln Lys Val Tyr Gln Ala Glu Met Asp Glu Leu
225                 230                 235                 240

Pro Ser Ala Phe Ala Asp Gly Ser Lys Asn Gly Gly Asp Lys His Gly
                245                 250                 255

Ala Asn Ser Leu Lys Ile Thr Glu Lys Val Ser Gly Gln His Val Glu
            260                 265                 270

Ile Gln Ala Lys Tyr Ile Gly Thr Thr Ile Val Val Arg Gln Val Gly
        275                 280                 285

Arg Tyr Leu Thr Phe Ala Val Arg Met Pro Glu Glu Val Val Asn Ala
    290                 295                 300

Val Glu Asp Arg Asp Ser Gln Gly Leu Tyr Leu Cys Leu Arg Gly Cys
305                 310                 315                 320

Pro Leu Asn Gln Gln Ile Asp Phe Gln Ala Phe Arg Ala Asn Ala Glu
                325                 330                 335

Ser Pro Arg Arg Pro Ala Ala Ala Ser Pro Ser Pro Val Val Pro Glu
            340                 345                 350

Thr Phe Pro Tyr Glu Thr Ala Val Ala Lys Cys Lys Glu Lys Leu Pro
        355                 360                 365

Val Glu Asp Leu Tyr Tyr Gln Ala Cys Val Phe Asp Leu Leu Thr Thr
    370                 375                 380

Gly Asp Val Asn Phe Thr Leu Ala Ala Tyr Tyr Ala Leu Glu Asp Gly
385                 390                 395                 400

Lys Met Leu His Ser Asn Lys Asp Lys Leu His Leu Phe Glu Arg Thr
                405                 410                 415

Arg Glu Leu Pro Gly Ala Val Ala Ala Ala Phe Pro Leu Ala Pro
            420                 425                 430

Glu Met Leu Pro Gly Thr Val Thr Leu Leu Val Leu Leu Pro Leu Phe
        435                 440                 445

Trp

<210> SEQ ID NO 4
<211> LENGTH: 234
<212> TYPE: PRT
<213> ORGANISM: Mus musculus

<400> SEQUENCE: 4

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Ser Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Leu Asn
            100                 105                 110

Thr Leu Pro Trp Thr Phe Gly Gly Gly Thr Lys Leu Glu Ile Lys Arg
```

```
            115                 120                 125
Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 5
<211> LENGTH: 471
<212> TYPE: PRT
<213> ORGANISM: Mus musculus

<400> SEQUENCE: 5

```
Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
50                  55                  60

Glu Trp Val Ala Glu Ile Arg Ser Lys Ala Asn Asn His Ala Thr Tyr
65                  70                  75                  80

Tyr Ala Glu Ser Val Lys Gly Arg Phe Thr Ile Ser Arg Asp Asp Ser
                85                  90                  95

Lys Arg Ser Val Tyr Leu Gln Met Asn Asn Leu Arg Ala Glu Asp Thr
            100                 105                 110

Gly Ile Tyr Tyr Cys Thr Arg Arg Asp Gly Ala Tyr Trp Gly Gln Gly
        115                 120                 125

Thr Leu Val Thr Val Ser Ala Ala Lys Thr Thr Pro Pro Ser Val Tyr
130                 135                 140

Pro Leu Ala Pro Gly Cys Gly Asp Thr Thr Gly Ser Ser Val Thr Leu
145                 150                 155                 160

Gly Cys Leu Val Lys Gly Tyr Phe Pro Glu Ser Val Thr Val Thr Trp
                165                 170                 175

Asn Ser Gly Ser Leu Ser Ser Ser Val His Thr Phe Pro Ala Leu Leu
            180                 185                 190

Gln Ser Gly Leu Tyr Thr Met Ser Ser Ser Val Thr Val Pro Ser Ser
        195                 200                 205

Thr Trp Pro Ser Gln Thr Val Thr Cys Ser Val Ala His Pro Ala Ser
210                 215                 220

Ser Thr Thr Val Asp Lys Lys Leu Glu Pro Ser Gly Pro Ile Ser Thr
225                 230                 235                 240

Ile Asn Pro Cys Pro Pro Cys Lys Glu Cys His Lys Cys Pro Ala Pro
                245                 250                 255
```

```
Asn Leu Glu Gly Gly Pro Ser Val Phe Ile Phe Pro Asn Ile Lys
            260                 265                 270

Asp Val Leu Met Ile Ser Leu Thr Pro Lys Val Thr Cys Val Val
            275                 280                 285

Asp Val Ser Glu Asp Pro Asp Val Gln Ile Ser Trp Phe Val Asn
            290                 295                 300

Asn Val Glu Val His Thr Ala Gln Thr Gln Thr His Arg Glu Asp Tyr
305                 310                 315                 320

Asn Ser Thr Ile Arg Val Val Ser Thr Leu Pro Ile Gln His Gln Asp
                325                 330                 335

Trp Met Ser Gly Lys Glu Phe Lys Cys Lys Val Asn Asn Lys Asp Leu
                340                 345                 350

Pro Ser Pro Ile Glu Arg Thr Ile Ser Lys Ile Lys Gly Leu Val Arg
                355                 360                 365

Ala Pro Gln Val Tyr Ile Leu Pro Pro Ala Glu Gln Leu Ser Arg
            370                 375                 380

Lys Asp Val Ser Leu Thr Cys Leu Val Val Gly Phe Asn Pro Gly Asp
385                 390                 395                 400

Ile Ser Val Glu Trp Thr Ser Asn Gly His Thr Glu Glu Asn Tyr Lys
                405                 410                 415

Asp Thr Ala Pro Val Leu Asp Ser Asp Gly Ser Tyr Phe Ile Tyr Ser
            420                 425                 430

Lys Leu Asn Met Lys Thr Ser Lys Trp Glu Lys Thr Asp Ser Phe Ser
                435                 440                 445

Cys Asn Val Arg His Glu Gly Leu Lys Asn Tyr Tyr Leu Lys Lys Thr
450                 455                 460

Ile Ser Arg Ser Pro Gly Lys
465                 470

<210> SEQ ID NO 6
<211> LENGTH: 238
<212> TYPE: PRT
<213> ORGANISM: Mus musculus

<400> SEQUENCE: 6

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Arg Pro
50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Leu Tyr Phe Cys
            100                 105                 110

Ser Gln Ser Thr His Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160
```

Asn Asn Phe Tyr Pro Lys Asp Ile Asn Val Lys Trp Lys Ile Asp Gly
              165                 170                 175

Ser Glu Arg Gln Asn Gly Val Leu Asn Ser Trp Thr Asp Gln Asp Ser
        180                 185                 190

Lys Asp Ser Thr Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Asn Glu Cys
225                 230                 235

<210> SEQ ID NO 7
<211> LENGTH: 466
<212> TYPE: PRT
<213> ORGANISM: Mus musculus

<400> SEQUENCE: 7

Met Lys Val Leu Ser Leu Leu Tyr Leu Leu Thr Ala Ile Pro Gly Ile
1               5                   10                  15

Met Ser Asp Val Lys Leu Gln Glu Ser Gly Pro Gly Leu Val Lys Pro
            20                  25                  30

Ser Gln Ser Leu Ser Leu Thr Cys Ser Val Thr Gly Tyr Ser Ile Thr
        35                  40                  45

Thr Ser Tyr Tyr Trp Asn Trp Ile Arg Gln Phe Pro Gly Asn Lys Leu
    50                  55                  60

Glu Trp Met Gly Tyr Ile Ser Tyr Asp Gly Thr Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Arg Leu Asn Ser Val Thr Thr Glu Asp Thr Ala Thr Tyr
            100                 105                 110

Tyr Cys Ala Gly Ser Phe Gly Tyr Ser Gln Gly Thr Leu Val Thr Val
        115                 120                 125

Ser Ala Ala Lys Thr Thr Pro Pro Ser Val Tyr Pro Leu Ala Pro Gly
    130                 135                 140

Cys Gly Asp Thr Thr Gly Ser Ser Val Thr Leu Gly Cys Leu Val Lys
145                 150                 155                 160

Gly Tyr Phe Pro Glu Ser Val Thr Val Thr Trp Asn Ser Gly Ser Leu
                165                 170                 175

Ser Ser Ser Val His Thr Phe Pro Ala Leu Leu Gln Ser Gly Leu Tyr
            180                 185                 190

Thr Met Ser Ser Ser Val Thr Val Pro Ser Ser Thr Trp Pro Ser Gln
        195                 200                 205

Thr Val Thr Cys Ser Val Ala His Pro Ala Ser Ser Thr Thr Val Asp
    210                 215                 220

Lys Lys Leu Glu Pro Ser Gly Pro Ile Ser Thr Ile Asn Pro Cys Pro
225                 230                 235                 240

Pro Cys Lys Glu Cys His Lys Cys Pro Ala Pro Asn Leu Glu Gly Gly
                245                 250                 255

Pro Ser Val Phe Ile Phe Pro Asn Ile Lys Asp Val Leu Met Ile
            260                 265                 270

Ser Leu Thr Pro Lys Val Thr Cys Val Val Val Asp Val Ser Glu Asp
        275                 280                 285

Asp Pro Asp Val Gln Ile Ser Trp Phe Val Asn Asn Val Glu Val His

```
                    290                 295                 300
Thr Ala Gln Thr Gln Thr His Arg Glu Asp Tyr Asn Ser Thr Ile Arg
305                 310                 315                 320

Val Val Ser Thr Leu Pro Ile Gln His Gln Asp Trp Met Ser Gly Lys
                325                 330                 335

Glu Phe Lys Cys Lys Val Asn Asn Lys Asp Leu Pro Ser Pro Ile Glu
            340                 345                 350

Arg Thr Ile Ser Lys Ile Lys Gly Leu Val Arg Ala Pro Gln Val Tyr
        355                 360                 365

Ile Leu Pro Pro Pro Ala Glu Gln Leu Ser Arg Lys Asp Val Ser Leu
    370                 375                 380

Thr Cys Leu Val Val Gly Phe Asn Pro Gly Asp Ile Ser Val Glu Trp
385                 390                 395                 400

Thr Ser Asn Gly His Thr Glu Glu Asn Tyr Lys Asp Thr Ala Pro Val
                405                 410                 415

Leu Asp Ser Asp Gly Ser Tyr Phe Ile Tyr Ser Lys Leu Asn Met Lys
            420                 425                 430

Thr Ser Lys Trp Glu Lys Thr Asp Ser Phe Ser Cys Asn Val Arg His
        435                 440                 445

Glu Gly Leu Lys Asn Tyr Tyr Leu Lys Lys Thr Ile Ser Arg Ser Pro
    450                 455                 460

Gly Lys
465

<210> SEQ ID NO 8
<211> LENGTH: 214
<212> TYPE: PRT
<213> ORGANISM: Artificial Sequence
<220> FEATURE:
<223> OTHER INFORMATION: Synthetic Schimeric antibody light chain

<400> SEQUENCE: 8

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Ser Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Leu Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
            180                 185                 190
Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 446
<212> TYPE: PRT
<213> ORGANISM: Artificial Sequence
<220> FEATURE:
<223> OTHER INFORMATION: Synthetic chimeric antibody heavy chain

<400> SEQUENCE: 9

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Arg Ser
65                  70                  75                  80

Val Tyr Leu Gln Met Asn Asn Leu Arg Ala Glu Asp Thr Gly Ile Tyr
                85                  90                  95

Tyr Cys Thr Arg Arg Asp Gly Ala Tyr Trp Gly Gln Gly Thr Leu Val
            100                 105                 110

Thr Val Ser Ala Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

```
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
            405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445

<210> SEQ ID NO 10
<211> LENGTH: 1461
<212> TYPE: PRT
<213> ORGANISM: Homo sapiens

<400> SEQUENCE: 10

Met Ala Ala Glu Arg Gly Ala Arg Arg Leu Leu Ser Thr Pro Ser Phe
1               5                   10                  15
Trp Leu Tyr Cys Leu Leu Leu Gly Arg Arg Ala Pro Gly Ala Ala
            20                  25                  30
Ala Ala Arg Ser Gly Ser Ala Pro Gln Ser Pro Gly Ala Ser Ile Arg
            35                  40                  45
Thr Phe Thr Pro Phe Tyr Phe Leu Val Glu Pro Val Asp Thr Leu Ser
        50                  55                  60
Val Arg Gly Ser Ser Val Ile Leu Asn Cys Ser Ala Tyr Ser Glu Pro
65                  70                  75                  80
Ser Pro Lys Ile Glu Trp Lys Lys Asp Gly Thr Phe Leu Asn Leu Val
                85                  90                  95
Ser Asp Asp Arg Arg Gln Leu Leu Pro Asp Gly Ser Leu Phe Ile Ser
            100                 105                 110
Asn Val Val His Ser Lys His Asn Lys Pro Asp Glu Gly Tyr Tyr Gln
            115                 120                 125
Cys Val Ala Thr Val Glu Ser Leu Gly Thr Ile Ile Ser Arg Thr Ala
        130                 135                 140
Lys Leu Ile Val Ala Gly Leu Pro Arg Phe Thr Ser Gln Pro Glu Pro
145                 150                 155                 160
Ser Ser Val Tyr Ala Gly Asn Asn Ala Ile Leu Asn Cys Glu Val Asn
                165                 170                 175
Ala Asp Leu Val Pro Phe Val Arg Trp Glu Gln Asn Arg Gln Pro Leu
            180                 185                 190
Leu Leu Asp Asp Arg Val Ile Lys Leu Pro Ser Gly Met Leu Val Ile
            195                 200                 205
Ser Asn Ala Thr Glu Gly Asp Gly Gly Leu Tyr Arg Cys Val Val Glu
        210                 215                 220
Ser Gly Gly Pro Pro Lys Tyr Ser Asp Glu Val Glu Leu Lys Val Leu
225                 230                 235                 240
Pro Asp Pro Glu Val Ile Ser Asp Leu Val Phe Leu Lys Gln Pro Ser
                245                 250                 255
```

```
Pro Leu Val Arg Val Ile Gly Gln Asp Val Val Leu Pro Cys Val Ala
            260                 265                 270

Ser Gly Leu Pro Thr Pro Thr Ile Lys Trp Met Lys Asn Glu Glu Ala
        275                 280                 285

Leu Asp Thr Glu Ser Ser Glu Arg Leu Val Leu Leu Ala Gly Gly Ser
    290                 295                 300

Leu Glu Ile Ser Asp Val Thr Glu Asp Asp Ala Gly Thr Tyr Phe Cys
305                 310                 315                 320

Ile Ala Asp Asn Gly Asn Glu Thr Ile Glu Ala Gln Ala Glu Leu Thr
                325                 330                 335

Val Gln Ala Gln Pro Glu Phe Leu Lys Gln Pro Thr Asn Ile Tyr Ala
            340                 345                 350

His Glu Ser Met Asp Ile Val Phe Glu Cys Glu Val Thr Gly Lys Pro
        355                 360                 365

Thr Pro Thr Val Lys Trp Val Lys Asn Gly Asp Met Val Ile Pro Ser
    370                 375                 380

Asp Tyr Phe Lys Ile Val Lys Glu His Asn Leu Gln Val Leu Gly Leu
385                 390                 395                 400

Val Lys Ser Asp Glu Gly Phe Tyr Gln Cys Ile Ala Glu Asn Asp Val
                405                 410                 415

Gly Asn Ala Gln Ala Gly Ala Gln Leu Ile Ile Leu Glu His Ala Pro
            420                 425                 430

Ala Thr Thr Gly Pro Leu Pro Ser Ala Pro Arg Asp Val Val Ala Ser
        435                 440                 445

Leu Val Ser Thr Arg Phe Ile Lys Leu Thr Trp Arg Thr Pro Ala Ser
    450                 455                 460

Asp Pro His Gly Asp Asn Leu Thr Tyr Ser Val Phe Tyr Thr Lys Glu
465                 470                 475                 480

Gly Ile Ala Arg Glu Arg Val Glu Asn Thr Ser His Pro Gly Glu Met
                485                 490                 495

Gln Val Thr Ile Gln Asn Leu Met Pro Ala Thr Val Tyr Ile Phe Arg
            500                 505                 510

Val Met Ala Gln Asn Lys His Gly Ser Gly Glu Ser Ser Ala Pro Leu
        515                 520                 525

Arg Val Glu Thr Gln Pro Glu Val Gln Leu Pro Gly Pro Ala Pro Asn
    530                 535                 540

Leu Arg Ala Tyr Ala Ala Ser Pro Thr Ser Ile Thr Val Thr Trp Glu
545                 550                 555                 560

Thr Pro Val Ser Gly Asn Gly Glu Ile Gln Asn Tyr Lys Leu Tyr Tyr
                565                 570                 575

Met Glu Lys Gly Thr Asp Lys Glu Gln Asp Val Asp Val Ser Ser His
            580                 585                 590

Ser Tyr Thr Ile Asn Gly Leu Lys Lys Tyr Thr Glu Tyr Ser Phe Arg
        595                 600                 605

Val Val Ala Tyr Asn Lys His Gly Pro Gly Val Ser Thr Pro Asp Val
    610                 615                 620

Ala Val Arg Thr Leu Ser Asp Val Pro Ser Ala Ala Pro Gln Asn Leu
625                 630                 635                 640

Ser Leu Glu Val Arg Asn Ser Lys Ser Ile Met Ile His Trp Gln Pro
                645                 650                 655

Pro Ala Pro Ala Thr Gln Asn Gly Gln Ile Thr Gly Tyr Lys Ile Arg
            660                 665                 670

Tyr Arg Lys Ala Ser Arg Lys Ser Asp Val Thr Glu Thr Leu Val Ser
```

```
                675                 680                 685
Gly Thr Gln Leu Ser Gln Leu Ile Glu Gly Leu Asp Arg Gly Thr Glu
    690                 695                 700

Tyr Asn Phe Arg Val Ala Ala Leu Thr Ile Asn Gly Thr Gly Pro Ala
705                 710                 715                 720

Thr Asp Trp Leu Ser Ala Glu Thr Phe Glu Ser Asp Leu Asp Glu Thr
                725                 730                 735

Arg Val Pro Glu Val Pro Ser Ser Leu His Val Arg Pro Leu Val Thr
            740                 745                 750

Ser Ile Val Val Ser Trp Thr Pro Pro Glu Asn Gln Asn Ile Val Val
        755                 760                 765

Arg Gly Tyr Ala Ile Gly Tyr Gly Ile Gly Ser Pro His Ala Gln Thr
    770                 775                 780

Ile Lys Val Asp Tyr Lys Gln Arg Tyr Tyr Thr Ile Glu Asn Leu Asp
785                 790                 795                 800

Pro Ser Ser His Tyr Val Ile Thr Leu Lys Ala Phe Asn Asn Val Gly
                805                 810                 815

Glu Gly Ile Pro Leu Tyr Glu Ser Ala Val Thr Arg Pro His Thr Asp
            820                 825                 830

Thr Ser Glu Val Asp Leu Phe Val Ile Asn Ala Pro Tyr Thr Pro Val
        835                 840                 845

Pro Asp Pro Thr Pro Met Met Pro Pro Val Gly Val Gln Ala Ser Ile
    850                 855                 860

Leu Ser His Asp Thr Ile Arg Ile Thr Trp Ala Asp Asn Ser Leu Pro
865                 870                 875                 880

Lys His Gln Lys Ile Thr Asp Ser Arg Tyr Tyr Thr Val Arg Trp Lys
                885                 890                 895

Thr Asn Ile Pro Ala Asn Thr Lys Tyr Lys Asn Ala Asn Ala Thr Thr
            900                 905                 910

Leu Ser Tyr Leu Val Thr Gly Leu Lys Pro Asn Thr Leu Tyr Glu Phe
        915                 920                 925

Ser Val Met Val Thr Lys Gly Arg Arg Ser Ser Thr Trp Ser Met Thr
    930                 935                 940

Ala His Gly Thr Thr Phe Glu Leu Val Pro Thr Ser Pro Pro Lys Asp
945                 950                 955                 960

Val Thr Val Val Ser Lys Glu Gly Lys Pro Lys Thr Ile Ile Val Asn
                965                 970                 975

Trp Gln Pro Pro Ser Glu Ala Asn Gly Lys Ile Thr Gly Tyr Ile Ile
            980                 985                 990

Tyr Tyr Ser Thr Asp Val Asn Ala Glu Ile His Asp Trp Val Ile Glu
        995                 1000                1005

Pro Val Val Gly Asn Arg Leu Thr His Gln Ile Gln Glu Leu Thr
    1010                1015                1020

Leu Asp Thr Pro Tyr Tyr Phe Lys Ile Gln Ala Arg Asn Ser Lys
    1025                1030                1035

Gly Met Gly Pro Met Ser Glu Ala Val Gln Phe Arg Thr Pro Lys
    1040                1045                1050

Ala Asp Ser Ser Asp Lys Met Pro Asn Asp Gln Ala Ser Gly Ser
    1055                1060                1065

Gly Gly Lys Gly Ser Arg Leu Pro Asp Leu Gly Ser Asp Tyr Lys
    1070                1075                1080

Pro Pro Met Ser Gly Ser Asn Ser Pro His Gly Ser Pro Thr Ser
    1085                1090                1095
```

```
Pro Leu Asp Ser Asn Met Leu Leu Val Ile Ile Val Ser Val Gly
    1100            1105                1110
Val Ile Thr Ile Val Val Val Ile Ile Ala Val Phe Cys Thr
    1115            1120                1125
Arg Arg Thr Thr Ser His Gln Lys Lys Lys Arg Ala Ala Cys Lys
    1130            1135                1140
Ser Val Asn Gly Ser His Lys Tyr Lys Gly Asn Ser Lys Asp Val
    1145            1150                1155
Lys Pro Pro Asp Leu Trp Ile His His Glu Arg Leu Glu Leu Lys
    1160            1165                1170
Pro Ile Asp Lys Ser Pro Asp Pro Asn Pro Ile Met Thr Asp Thr
    1175            1180                1185
Pro Ile Pro Arg Asn Ser Gln Asp Ile Thr Pro Val Asp Asn Ser
    1190            1195                1200
Met Asp Ser Asn Ile His Gln Arg Arg Asn Ser Tyr Arg Gly His
    1205            1210                1215
Glu Ser Glu Asp Ser Met Ser Thr Leu Ala Gly Arg Arg Gly Met
    1220            1225                1230
Arg Pro Lys Met Met Met Pro Phe Asp Ser Gln Pro Pro Gln Pro
    1235            1240                1245
Val Ile Ser Ala His Pro Ile His Ser Leu Asp Asn Pro His His
    1250            1255                1260
His Phe His Ser Ser Ser Leu Ala Ser Pro Ala Arg Ser His Leu
    1265            1270                1275
Tyr His Pro Gly Ser Pro Trp Pro Ile Gly Thr Ser Met Ser Leu
    1280            1285                1290
Ser Asp Arg Ala Asn Ser Thr Glu Ser Val Arg Asn Thr Pro Ser
    1295            1300                1305
Thr Asp Thr Met Pro Ala Ser Ser Ser Gln Thr Cys Cys Thr Asp
    1310            1315                1320
His Gln Asp Pro Glu Gly Ala Thr Ser Ser Tyr Leu Ala Ser
    1325            1330                1335
Ser Gln Glu Glu Asp Ser Gly Gln Ser Leu Pro Thr Ala His Val
    1340            1345                1350
Arg Pro Ser His Pro Leu Lys Ser Phe Ala Val Pro Ala Ile Pro
    1355            1360                1365
Pro Pro Gly Pro Pro Thr Tyr Asp Pro Ala Leu Pro Ser Thr Pro
    1370            1375                1380
Leu Leu Ser Gln Gln Ala Leu Asn His His Ile His Ser Val Lys
    1385            1390                1395
Thr Ala Ser Ile Gly Thr Leu Gly Arg Ser Arg Pro Pro Met Pro
    1400            1405                1410
Val Val Val Pro Ser Ala Pro Glu Val Gln Glu Thr Thr Arg Met
    1415            1420                1425
Leu Glu Asp Ser Glu Ser Ser Tyr Glu Pro Asp Glu Leu Thr Lys
    1430            1435                1440
Glu Met Ala His Leu Glu Gly Leu Met Lys Asp Leu Asn Ala Ile
    1445            1450                1455
Thr Thr Ala
    1460

<210> SEQ ID NO 11
<211> LENGTH: 446
```

<212> TYPE: PRT
<213> ORGANISM: Artificial Sequence
<220> FEATURE:
<223> OTHER INFORMATION: Synthetic humanized antibody heavy chain HA

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp Ala
            20                  25                  30

Trp Met Asp Trp Phe Arg Gln Ala Pro Gly Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Leu Tyr
                85                  90                  95

Tyr Cys Thr Arg Arg Asp Gly Ala Tyr Trp Gly Lys Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
            435                 440                 445

<210> SEQ ID NO 12
<211> LENGTH: 446
<212> TYPE: PRT
<213> ORGANISM: Artificial Sequence
<220> FEATURE:
<223> OTHER INFORMATION: Synthetic humanized antibody heavy chain HB

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp Ala
            20                  25                  30

Trp Met Asp Trp Phe Arg Gln Ala Pro Gly Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Arg Thr Glu Asp Thr Ala Leu Tyr
                85                  90                  95

Tyr Cys Thr Arg Arg Asp Gly Ala Tyr Trp Gly Lys Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 13
<211> LENGTH: 446
<212> TYPE: PRT
<213> ORGANISM: Artificial Sequence
<220> FEATURE:
<223> OTHER INFORMATION: Synthetic humanized antibody heavy chain HC

<400> SEQUENCE: 13

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp Ala
            20                  25                  30

Trp Met Asp Trp Phe Arg Gln Ala Pro Gly Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Leu Tyr
                85                  90                  95

Tyr Cys Thr Arg Arg Asp Gly Ala Tyr Trp Gly Lys Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

```
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 14
<211> LENGTH: 446
<212> TYPE: PRT
<213> ORGANISM: Artificial Sequence
<220> FEATURE:
<223> OTHER INFORMATION: Synthetic humanized antibody heavy chain HD

<400> SEQUENCE: 14

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp Ala
            20                  25                  30

Trp Met Asp Trp Phe Arg Gln Ala Pro Gly Lys Gly Leu Glu Trp Val
        35                  40                  45

Ala Glu Ile Arg Ser Lys Ala Asn Asn His Ala Thr Tyr Tyr Ala Glu
50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Arg Thr Glu Asp Thr Ala Leu Tyr
            85                  90                  95

Tyr Cys Thr Arg Arg Asp Gly Ala Tyr Trp Gly Lys Gly Thr Thr Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140
```

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 15
<211> LENGTH: 446
<212> TYPE: PRT
<213> ORGANISM: Artificial Sequence
<220> FEATURE:
<223> OTHER INFORMATION: Synthetic humanized antibody heavy chain HE

<400> SEQUENCE: 15

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Asn Asn His Ala Thr Tyr Tyr Ala Glu
    50                  55                  60

```
Ser Val Lys Gly Arg Phe Thr Ile Ser Arg Asp Asp Ser Lys Ser Ile
 65                  70                  75                  80

Val Tyr Leu Gln Met Asn Ser Leu Arg Thr Glu Asp Thr Ala Leu Tyr
                 85                  90                  95

Tyr Cys Thr Arg Arg Asp Gly Ala Tyr Trp Gly Lys Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 16
<211> LENGTH: 446
<212> TYPE: PRT
<213> ORGANISM: Artificial Sequence
<220> FEATURE:
<223> OTHER INFORMATION: Synthetic humanized antibody heavy chain HF
```

```
<400> SEQUENCE: 16

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp Ala
            20                  25                  30

Trp Met Asp Trp Phe Arg Gln Ala Pro Gly Lys Gly Leu Glu Trp Val
        35                  40                  45

Ala Glu Ile Arg Ser Lys Ala Asn Asn His Ala Thr Tyr Tyr Ala Glu
50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Arg Asp Gly Ala Tyr Trp Gly Lys Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
```

```
                    405                 410                 415
Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 17
<211> LENGTH: 446
<212> TYPE: PRT
<213> ORGANISM: Artificial Sequence
<220> FEATURE:
<223> OTHER INFORMATION: Synthetic humanized antibody heavy chain HG

<400> SEQUENCE: 17

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Leu Tyr
                85                  90                  95

Tyr Cys Thr Arg Arg Asp Gly Ala Tyr Trp Gly Lys Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

```
                        325                 330                 335
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 18
<211> LENGTH: 446
<212> TYPE: PRT
<213> ORGANISM: Artificial Sequence
<220> FEATURE:
<223> OTHER INFORMATION: Synthetic humanized antibody heavy chain HH

<400> SEQUENCE: 18

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp Ala
            20                  25                  30

Trp Met Asp Trp Val Arg Gln Ala Pro Gly Lys Gly Leu Glu Trp Val
            35                  40                  45

Ala Glu Ile Arg Ser Lys Ala Asn Asn His Ala Thr Tyr Tyr Ala Glu
            50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Arg Asp Gly Ala Tyr Trp Gly Lys Gly Thr Thr Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
```

Glu Val Thr Cys Val Val Val Asp Val Ser His Glu Asp Pro Glu Val
            245                 250                 255

Lys Phe Asn Trp Tyr Val Asp Gly Val Glu Val His Asn Ala Lys Thr
        260                 265                 270

Lys Pro Arg Glu Gln Tyr Asn Ser Thr Tyr Arg Val Val Ser Val
    275                 280                 285

Leu Thr Val Leu His Gln Asp Trp Leu Asn Gly Lys Glu Tyr Lys Cys
290                 295                 300

Lys Val Ser Asn Lys Ala Leu Pro Ala Pro Ile Glu Lys Thr Ile Ser
305                 310                 315                 320

Lys Ala Lys Gly Gln Pro Arg Glu Pro Gln Val Tyr Thr Leu Pro Pro
            325                 330                 335

Ser Arg Asp Glu Leu Thr Lys Asn Gln Val Ser Leu Thr Cys Leu Val
        340                 345                 350

Lys Gly Phe Tyr Pro Ser Asp Ile Ala Val Glu Trp Glu Ser Asn Gly
    355                 360                 365

Gln Pro Glu Asn Asn Tyr Lys Thr Thr Pro Pro Val Leu Asp Ser Asp
370                 375                 380

Gly Ser Phe Phe Leu Tyr Ser Lys Leu Thr Val Asp Lys Ser Arg Trp
385                 390                 395                 400

Gln Gln Gly Asn Val Phe Ser Cys Ser Val Met His Glu Ala Leu His
            405                 410                 415

Asn His Tyr Thr Gln Lys Ser Leu Ser Leu Ser Pro Gly Lys
        420                 425                 430

435                 440                 445

<210> SEQ ID NO 19
<211> LENGTH: 214
<212> TYPE: PRT
<213> ORGANISM: Artificial Sequence
<220> FEATURE:
<223> OTHER INFORMATION: Synthetic humanized antibody light chain KA

<400> SEQUENCE: 19

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Phe Cys Gln Gln Leu Asn Thr Leu Pro Trp
                85                  90                  95

Thr Phe Gly Gly Gly Thr Lys Val Glu Met Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser 165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 214
<212> TYPE: PRT
<213> ORGANISM: Artificial Sequence
<220> FEATURE:
<223> OTHER INFORMATION: Synthetic humanized antibody light chain KB

<400> SEQUENCE: 20

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Ser Tyr Phe Cys Gln Gln Leu Asn Thr Leu Pro Trp
                85                  90                  95

Thr Phe Gly Gly Gly Thr Lys Val Glu Met Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 214
<212> TYPE: PRT
<213> ORGANISM: Artificial Sequence
<220> FEATURE:
<223> OTHER INFORMATION: Synthetic humanized antibody light chain KC

<400> SEQUENCE: 21

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Tyr
            20                  25                  30

```
Leu Asn Trp Tyr Gln Gln Lys Pro Gly Lys Ala Val Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Ser Tyr Phe Cys Gln Gln Leu Asn Thr Leu Pro Trp
                 85                  90                  95

Thr Phe Gly Gly Gly Thr Lys Val Glu Met Glu Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 22
<211> LENGTH: 214
<212> TYPE: PRT
<213> ORGANISM: Artificial Sequence
<220> FEATURE:
<223> OTHER INFORMATION: Synthetic humanized antibody light chain KD

<400> SEQUENCE: 22

Asp Ile Gln Met Thr Gln Ser Pro Ser Ser Val Ser Ala Ser Val Gly
1                5                  10                  15

Asp Arg Val Thr Ile Thr Cys Arg Ala Ser Gln Asp Ile Ser Ser Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Leu Asn Thr Leu Pro Trp
                 85                  90                  95

Thr Phe Gly Gly Gly Thr Lys Val Glu Met Glu Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 214
<212> TYPE: PRT
<213> ORGANISM: Artificial Sequence
<220> FEATURE:
<223> OTHER INFORMATION: Synthetic humanized antibody light chain KE

<400> SEQUENCE: 23

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Ser Tyr Phe Cys Gln Gln Leu Asn Thr Leu Pro Trp
                85                  90                  95

Thr Phe Gly Gly Gly Thr Lys Val Glu Met Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 214
<212> TYPE: PRT
<213> ORGANISM: Artificial Sequence
<220> FEATURE:
<223> OTHER INFORMATION: Synthetic humanized antibody light chain KF

<400> SEQUENCE: 24

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Val Lys Leu Leu Ile
        35                  40                  45
```

Tyr Tyr Thr Ser Arg Leu His Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Leu Asn Thr Leu Pro Trp
                 85                  90                  95

Thr Phe Gly Gly Gly Thr Lys Val Glu Met Glu Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 25
<211> LENGTH: 214
<212> TYPE: PRT
<213> ORGANISM: Artificial Sequence
<220> FEATURE:
<223> OTHER INFORMATION: Synthetic humanized antibody light chain KG

<400> SEQUENCE: 25

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Ser Ser Tyr
             20                  25                  30

Leu Asn Trp Tyr Gln Gln Lys Pro Gly Lys Ala Val Lys Leu Leu Ile
         35                  40                  45

Tyr Tyr Thr Ser Arg Leu His Ser Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Phe Cys Gln Gln Leu Asn Thr Leu Pro Trp
                 85                  90                  95

Thr Phe Gly Gly Gly Thr Lys Val Glu Met Glu Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 26
<211> LENGTH: 14
<212> TYPE: PRT
<213> ORGANISM: Mus musculus

<400> SEQUENCE: 26

Glu Glu Val Val Asn Ala Val Glu Asp Trp Asp Ser Gln Gly
1               5                   10

<210> SEQ ID NO 27
<211> LENGTH: 14
<212> TYPE: PRT
<213> ORGANISM: Mus musculus

<400> SEQUENCE: 27

Asn Gln Gln Ile Asp Phe Gln Ala Phe His Thr Asn Ala Glu
1               5                   10

<210> SEQ ID NO 28
<211> LENGTH: 11
<212> TYPE: PRT
<213> ORGANISM: Mus musculus

<400> SEQUENCE: 28

Pro Thr Ala Pro Glu Thr Phe Pro Tyr Glu Thr
1               5                   10

<210> SEQ ID NO 29
<211> LENGTH: 11
<212> TYPE: PRT
<213> ORGANISM: Mus musculus

<400> SEQUENCE: 29

Lys Leu Pro Val Glu Asp Leu Tyr Tyr Gln Ala
1               5                   10

<210> SEQ ID NO 30
<211> LENGTH: 11
<212> TYPE: PRT
<213> ORGANISM: Mus musculus

<400> SEQUENCE: 30

Arg Ala Ser Gln Asp Ile Ser Ser Tyr Leu Asn
1               5                   10

<210> SEQ ID NO 31
<211> LENGTH: 7
<212> TYPE: PRT
<213> ORGANISM: Mus musculus

<400> SEQUENCE: 31

Tyr Thr Ser Arg Leu His Ser
1               5

<210> SEQ ID NO 32
<211> LENGTH: 7
<212> TYPE: PRT
<213> ORGANISM: Mus musculus

```
<400> SEQUENCE: 32

Gln Gln Leu Asn Thr Leu Pro
1               5

<210> SEQ ID NO 33
<211> LENGTH: 5
<212> TYPE: PRT
<213> ORGANISM: Mus musculus

<400> SEQUENCE: 33

Asp Ala Trp Met Asp
1               5

<210> SEQ ID NO 34
<211> LENGTH: 19
<212> TYPE: PRT
<213> ORGANISM: Mus musculus

<400> SEQUENCE: 34

Glu Ile Arg Ser Lys Ala Asn Asn His Ala Thr Tyr Tyr Ala Glu Ser
1               5                   10                  15

Val Lys Gly

<210> SEQ ID NO 35
<211> LENGTH: 5
<212> TYPE: PRT
<213> ORGANISM: Mus musculus

<400> SEQUENCE: 35

Arg Asp Gly Ala Tyr
1               5

<210> SEQ ID NO 36
<211> LENGTH: 16
<212> TYPE: PRT
<213> ORGANISM: Mus musculus

<400> SEQUENCE: 36

Arg Ser Ser Gln Ser Leu Val His Ser Asn Gly Asn Thr Tyr Leu His
1               5                   10                  15

<210> SEQ ID NO 37
<211> LENGTH: 7
<212> TYPE: PRT
<213> ORGANISM: Mus musculus

<400> SEQUENCE: 37

Lys Val Ser Asn Arg Phe Ser
1               5

<210> SEQ ID NO 38
<211> LENGTH: 7
<212> TYPE: PRT
<213> ORGANISM: Mus musculus

<400> SEQUENCE: 38

Ser Gln Ser Thr His Val Pro
1               5

<210> SEQ ID NO 39
<211> LENGTH: 6
<212> TYPE: PRT
<213> ORGANISM: Mus musculus
```

```
<400> SEQUENCE: 39

Thr Ser Tyr Tyr Trp Asn
1               5

<210> SEQ ID NO 40
<211> LENGTH: 16
<212> TYPE: PRT
<213> ORGANISM: Mus musculus

<400> SEQUENCE: 40

Tyr Ile Ser Tyr Asp Gly Thr Asn Asn Tyr Asn Pro Ser Leu Lys Asn
1               5                   10                  15

<210> SEQ ID NO 41
<211> LENGTH: 116
<212> TYPE: PRT
<213> ORGANISM: Artificial Sequence
<220> FEATURE:
<223> OTHER INFORMATION: Synthetic humanized antibody heavy chain

<400> SEQUENCE: 41

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Arg Thr Glu Asp Thr Ala Leu Tyr
                85                  90                  95

Tyr Cys Thr Arg Arg Asp Gly Ala Tyr Trp Gly Lys Gly Thr Thr Val
            100                 105                 110

Thr Val Ser Ser
        115

<210> SEQ ID NO 42
<211> LENGTH: 107
<212> TYPE: PRT
<213> ORGANISM: Artificial Sequence
<220> FEATURE:
<223> OTHER INFORMATION: Synthetic humanized antibody light chain

<400> SEQUENCE: 42

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gly Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Phe Cys Gln Gln Leu Asn Thr Leu Pro Trp
                85                  90                  95

Thr Phe Gly Gly Gly Thr Lys Val Glu Met Glu
```

<210> SEQ ID NO 43
<211> LENGTH: 348
<212> TYPE: DNA
<213> ORGANISM: Artificial Sequence
<220> FEATURE:
<223> OTHER INFORMATION: Synthetic a gene encoding humanized antibody heavy chain

<400> SEQUENCE: 43

```
gaagtgcagc tggtggaatc tggcggcgga ctggtgcagc ctggcagatc cctgagactg      60
tcctgtaccg cctccggctt caccttctcc gacgcctgga tggattgggt gcgacaggct     120
cctggcaagg gcctggaatg ggtggccgag atccggtcca aggccaacaa ccacgccacc     180
tactacgccg agtctgtgaa gggccggttc accatctccc gggacgactc caagtccatc     240
gtgtacctgc agatgaactc cctgcggacc gaggacaccg ccctgtacta ctgcaccaga     300
agggacggcg cctactgggg caagggcacc acagtgacag tgtcctcc                 348
```

<210> SEQ ID NO 44
<211> LENGTH: 321
<212> TYPE: DNA
<213> ORGANISM: Artificial Sequence
<220> FEATURE:
<223> OTHER INFORMATION: Synthetic a gene encoding humanized antibody light chain

<400> SEQUENCE: 44

```
gacatccaga tgacccagtc cccctcctcc gtgtctgctt ccgtgggcga cagagtgacc      60
atcacctgtc gggcctccca ggacatctcc tcctacctga ctggtatca gcagaagccc     120
ggcaaggccc ccaagctgct gatctactac acctccggc tgcactccgg cgtgccctct     180
agattttccg gctctggctc cggcaccgac tttaccctga ccatctccag cctgcagccc     240
gaggacttcg cctcctactt ctgtcagcag ctgaacaccc tgccctggac ctttggcgga     300
ggcaccaagg tggaaatgga a                                              321
```

<210> SEQ ID NO 45
<211> LENGTH: 13
<212> TYPE: PRT
<213> ORGANISM: Artificial Sequence
<220> FEATURE:
<223> OTHER INFORMATION: Synthetic Sequence PLP139-151

<400> SEQUENCE: 45

His Ser Leu Gly Lys Trp Leu Gly His Pro Asp Lys Phe
1               5                   10

<210> SEQ ID NO 46
<211> LENGTH: 4
<212> TYPE: PRT
<213> ORGANISM: Artificial Sequence
<220> FEATURE:
<223> OTHER INFORMATION: Synthetic spacer

<400> SEQUENCE: 46

Ser Gly Ser Gly
1